(12) United States Patent
Kelly et al.

(10) Patent No.: US 9,797,002 B2
(45) Date of Patent: Oct. 24, 2017

(54) METHODS AND KITS FOR GENOME-WIDE METHYLATION OF GPC SITES AND GENOME-WIDE DETERMINATION OF CHROMATIN STRUCTURE

(75) Inventors: Theresa K. Kelly, Los Angeles, CA (US); Gangning Liang, Rowland Heights, CA (US); Peter A. Jones, La Canada, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 472 days.

(21) Appl. No.: 13/169,815

(22) Filed: Jun. 27, 2011

(65) Prior Publication Data

US 2012/0028817 A1 Feb. 2, 2012

Related U.S. Application Data

(60) Provisional application No. 61/358,767, filed on Jun. 25, 2010.

(51) Int. Cl.
*C12Q 1/68* (2006.01)
(52) U.S. Cl.
CPC .................................. *C12Q 1/6813* (2013.01)

(58) Field of Classification Search
None
See application file for complete search history.

(56) References Cited

U.S. PATENT DOCUMENTS 5,851,766 A * 12/1998 Ryals ................. C12N 15/8238
435/6.16

OTHER PUBLICATIONS

Kilgore et al., Single-molecule and population probing of chromatin structure using DNA methyltransferases; Methods vol. 41, pp. 320-332, 2007.*
Fatemi et al., Footprinting of mammalian promoters: use of a CpG DNA methyltransferase revealing nucleosome positions at a single molecule level; NAR, vol. 33, No. 20, e176 pp. 1-9, 2005.*

* cited by examiner

*Primary Examiner* — Addison D Ault
(74) *Attorney, Agent, or Firm* — DLA Piper LLP (US)

(57) ABSTRACT

Disclosed are methods and kits for genome-wide methylation of GpC sites and for genome-wide chromatin structural determination. Specifically, the methods and kits of the present invention make possible the simultaneous determination of endogenous DNA methylation state and chromatin architecture across the entire genome.

8 Claims, 63 Drawing Sheets

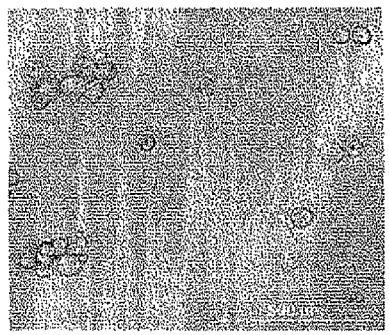 Fig. 3A Before Lysing
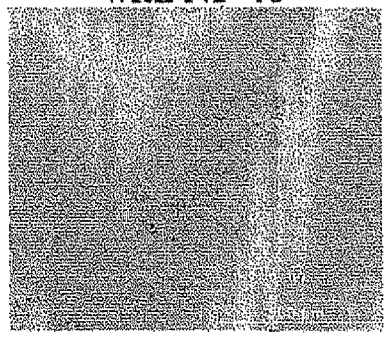 Fig. 3B After Lysing with NP-40

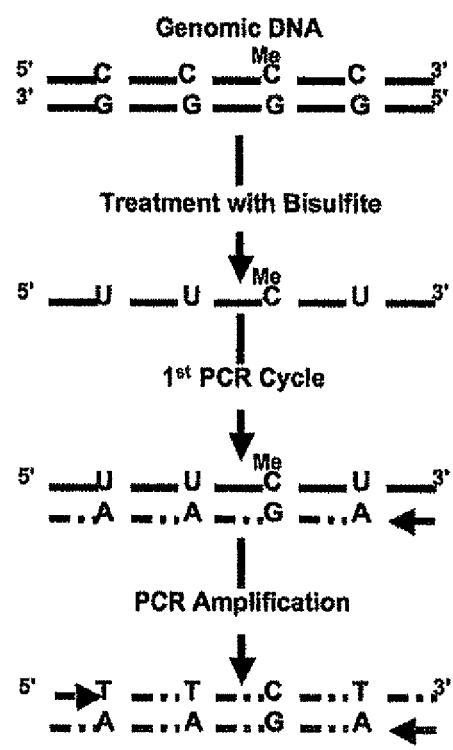

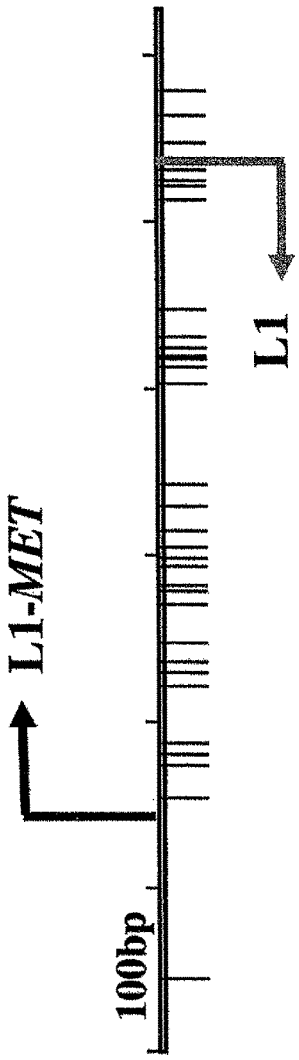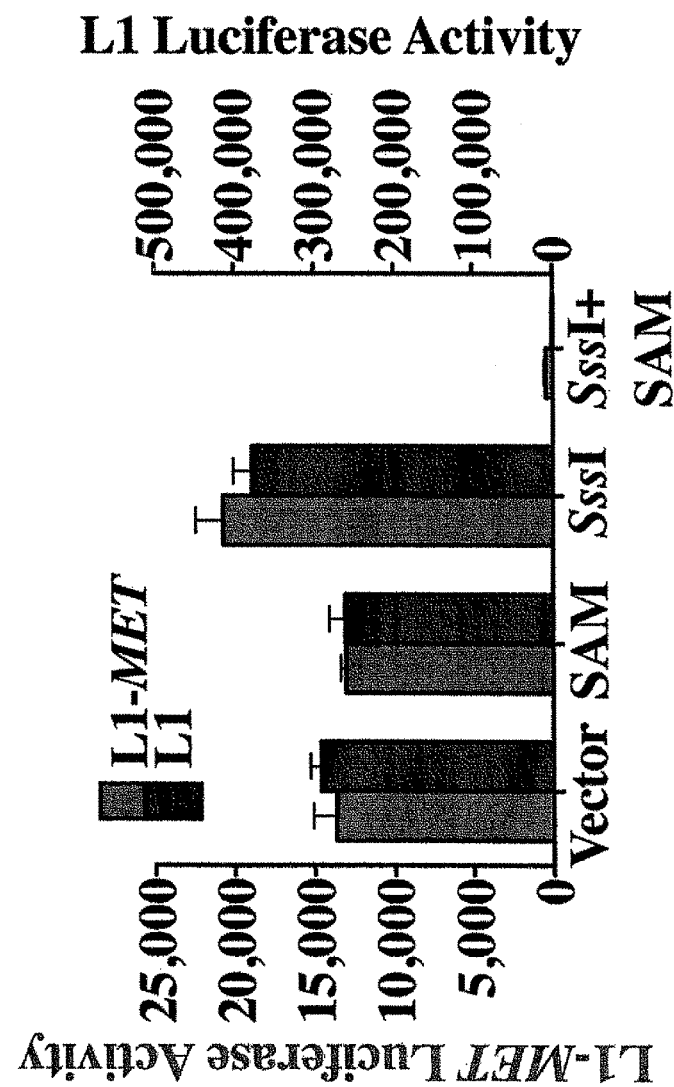
Fig. 8A
Fig. 8B

- Corresponding Normal (> 5cm)
- Corresponding Normal (0.5-2.5cm)
- Tumor

Specific L1s with Alternate Transcripts
Located in Intron of Genes

| Host gene | Alternate transcripts (#) | Location |
|---|---|---|
| MET | DA758395 (5) | chr7:116150248-2910 |
| ACVR1C | BE787024 (2) | chr2:158131300-800 |
| RAB3IP | BC015548 (8) | chr12:68459000-500 |
| BCAS3 | DA385484 (40) | chr17:56319000-500 |
| SMYD3 | BM809976 (3) | chr1:244046500-7000 |
| C12orf56 | BC042855 (8) | chr12:62973200-500 |
| CDH6 | DA493714 (4)/CX165494 (2) | chr16:60509700-10200 |
| DPY19L2P1 | DA748563 (2) | chr7:35099200-600 |
| GPR98 | DA438186 (2) | chr5:90153600-4000 |
| WDR72 | AK310211 (12) | chr15:51620100-600 |
| CHFM3 | AF279779 (5) | chr1:237859000-500 |
| CD96 | AV691164 (5) | chr3:112763500-4000 |
| FLJ16237 | DA737504 (4)/BE568663 (2) | chr7:15553300-4000 |
| MED12L | DA446764 | chr3:152442500-3000 |
| SCRN3 | CN259922 (20) | chr2:174983000-500 |
| NY-REN-7 | AK128539 (3) | chr5:177131000-700 |

Fig. 15C

5-RACE (L1 underlined):
<u>CAGACTGCTG TGCTAGCAAT CAGCGGGACT CCGTGGGCGT AGGACCCTCC GAGCCAGCAA GGGAAGCTTT TGGAAGCCAC CCGGTAGAGC TGGAAGAGAA TTTCGAAATC AATTCGCTCA ACC</u>

SEQ ID NO:6

Fig. 18C
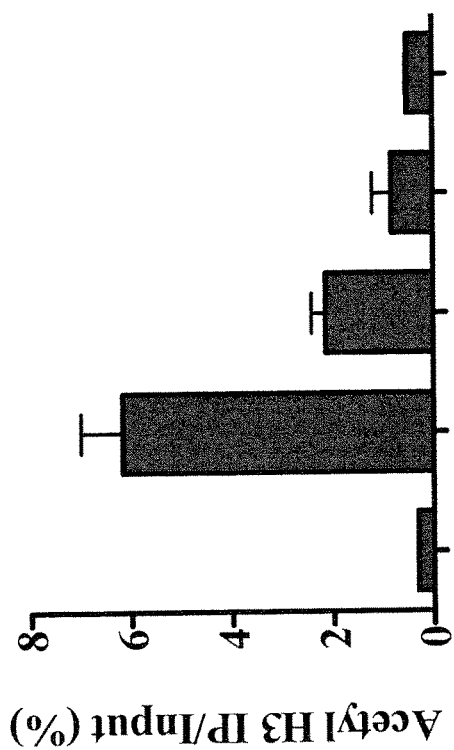
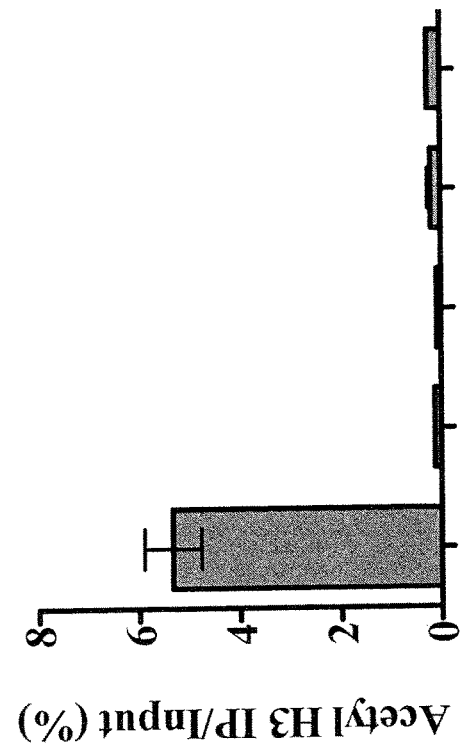

Fig. 18D
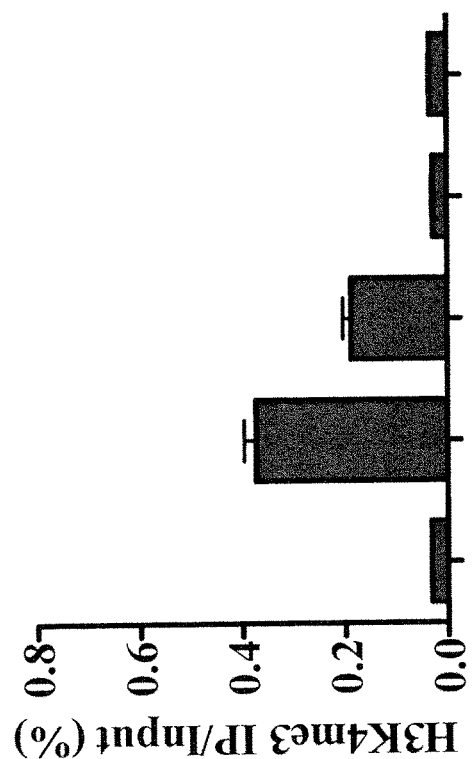
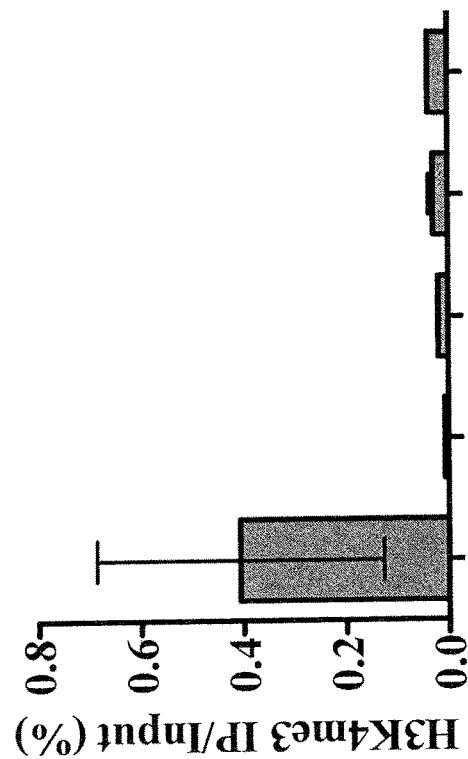

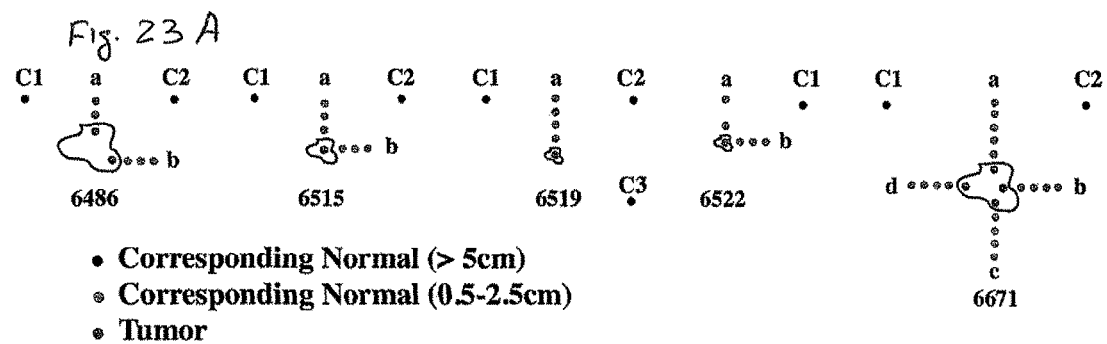
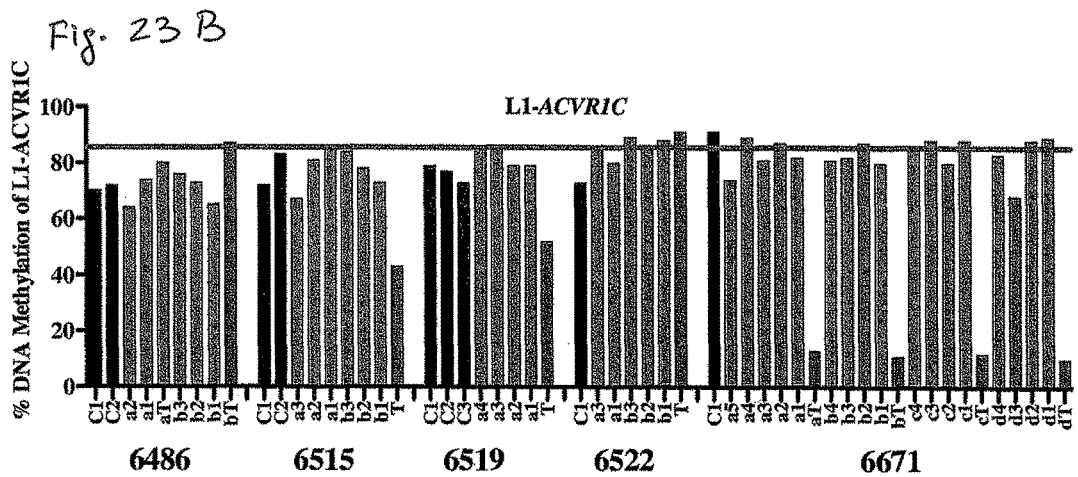
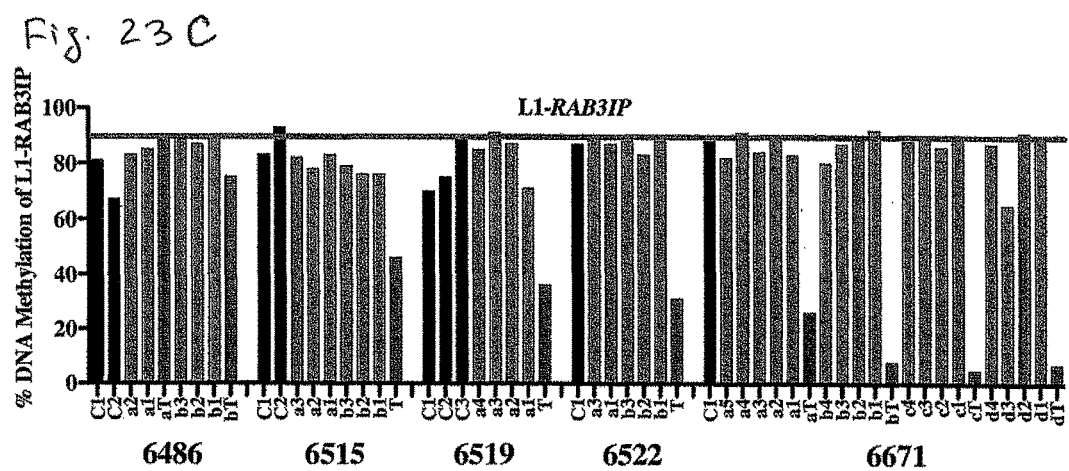

METHODS AND KITS FOR GENOME-WIDE METHYLATION OF GPC SITES AND GENOME-WIDE DETERMINATION OF CHROMATIN STRUCTURE

CROSS-REFERENCE TO RELATED APPLICATIONS

This application claims the benefit of U.S. Provisional Application No. 61/358,767, filed Jun. 25, 2010, the entire contents of which are incorporated herein by reference in its entirety.

STATEMENT REGARDING FEDERALLY SPONSORED RESEARCH OR DEVELOPMENT

This invention was made with government support under Contract Nos. CA82422, R01CA 124518 and R01CA 83867 awarded by the National Institutes of Health. The government has certain rights in the invention.

FIELD OF THE INVENTION

The present invention relates in general to methods and kits for genome-wide methylation of GpC sites and for genome-wide chromatin structural determination. Specifically, the methods and kits of the present invention make possible the simultaneous determination of endogenous DNA methylation state and chromatin architecture across the entire genome.

BACKGROUND OF THE INVENTION

Gene expression is regulated by genetic and epigenetic mechanisms. There are a variety of epigenetic mechanisms including DNA methylation (at CpG dinucleotides) and nucleosome positioning, which work together to generate chromatin states. Specific chromatin states facilitate, inhibit or allow for the potential of gene activation. Genome wide studies of chromatin states have focused on either DNA methylation or nucleosome positioning, and as a result a comprehensive integrated genome-wide view of DNA methylation and nucleosome positioning has not been done.

Methylation dependent single molecule footprinting techniques (M-SPA) rely on CpG methylation. Since CpG methylation occurs endogenously, analysis is limited to regions that are unmethylated. In addition, CpG sites are predisposed to mutation and thus have become under-represented in the genome overall and asymmetrically distributed into CpG rich and CpG poor regions. Thus M-SPA is limited to regions that are CpG rich. GpC dinucleotides do not have the same propensity for mutation and are more broadly distributed throughout in the genome.

As such, there is a continuing need for improved methods for determining endogenous methylation and nucleosome positioning simultaneously.

Recently, a GpC methyltransferase enzyme M.CviPI has become commercially available. M.CviPI methylates all cytosine residues ($C^5$) within the double-stranded dinucleotide recognition sequence 5' . . . GC . . . 3'. M.CviPI is isolated from a strain of E. coli which contains the methyltransferase gene from Chlorella virus. This construct is fused to the maltose binding protein (MBP).

SUMMARY OF THE INVENTION

One aspect of the present invention is the discovery that the GpC methyltransferase enzyme, M. CviPI, only methylates DNA on a genome wide basis under very certain conditions. As such, one aspect of the present invention is the genome-wide methylation of GpC sites, preferably using M. CviPI. Another aspect of the present invention is a kit for the genome-wide methylation of GpC sites, also preferably using M. CviPI.

Another aspect of the present invention is a method for genome-wide methylation-sensitive chromatin structure determination comprising providing eukaryotic cells with nuclei comprised of chromatin, wherein the chromatin is comprised of nucleosomes having DNA associated with histones and also optionally associated with one or more tight-binding factors, extracting the nuclei of the cells, methylating substantially all of the GpC sites of the chromatin not associated with nucleosomes or tight-binding factors, purifying the DNA, bisulfite converting the DNA, and sequencing the DNA; wherein the sequencing provides the endogenous methylation state of the DNA and the GpC sites associated with the nucleosomes or tight-binding factors. Preferably, the step of extracting the nuclei preferably comprises a step of lysing the cells to lyse the cytoplasmic membrane of the cell. Preferably, the step of methylating substantially all of the GpC sites comprises contacting the cells with a GpC methylating reagent comprising a methyl transfer agent, lysis prevention agent and an effective amount of a GpC methyltransferase.

The GpC methylating reagent preferably also comprises a buffer. In a further preferred embodiment, the methyl transfer agent is SAM, the lysing prevention agent is sucrose, and the GpC methyltransferase is M. CviPI.

Another aspect of the present invention is directed to a kit for genome-wide methylation sensitive chromatin structure determination comprising a cytoplasmic membrane lysing reagent, a GpC methylating reagent, a DNA purifying reagent; and instructions for using the reagents to prepare chromatin DNA for sequencing, wherein, when used as instructed, the endogenous methylation state of the DNA is preserved. The kit may also include a bisulfit conversion reagent. Preferably, when used as instructed, the GpC sites associated with the nucleosomes or tight-binding factors are preserved. The GpC methylating reagent comprises a methyl transfer agent, lysis prevention agent and an effective amount of a GpC methyltransferase, and preferably, a buffer.

Another aspect of the present invention is directed to a method of genome-wide methylation of substantially all DNA GpC sites not associated with nucleosomes or other tight-binding factors comprising providing eukaryotic cells with nuclei comprised of chromatin, wherein the chromatin is comprised of nucleosomes having DNA associated with histones and also optionally associated with tight-binding factors, extracting the nuclei of the cells, contacting the nuclei with a GpC methylating reagent comprised of a methyl transfer agent, a lysis prevention agent (preferably sucrose) and an effective amount of GpC methyltransferase; and incubating the combination of the nuclei and GpC methylating reagent such that substantially all of the GpC cites of the nuclei's chromatin not associated with nucleosomes and, optionally, tight-binding factors are methylated, wherein one or more of endogenous DNA CpG methylation status, a native chromatin structure and the protein binding is preserved. Preferably, the DNA CpG methylation status, the native chromatin structure and the protein binding are preserved. The step of extracting the nuclei comprises a step of lysing the cells to lyse the cytoplasmic membrane of the cell.

Another aspect of the present invention is directed to a kit for genome-wide methylation of substantially all GpC not associated with nucleosomes or other tight-binding factors comprising a cytoplasmic membrane lysing reagent, a GpC methylating reagent comprised of a methyl transfer agent, lysis prevention agent and an effective amount of M. CviPI, and instructions for using the reagents to methylate substantially all of the GpC cites of the nuclei's chromatin not associated with nucleosomes or tight-binding factors, wherein one or more of endogenous DNA CpG methylation status, native chromatin structure and protein binding is preserved.

Another aspect of the present invention is the use of, amongst other techniques, GpC methylation and bisulfite conversion, to determine chromatin structure. Using the methods and kits of the present invention enables the examination of both nucleosome positioning and endogenous CpG methylation within the same DNA molecule. Using, for instance, massively parallel sequencing combined with the GpC footprinting methodology, an integrated view of DNA methylation and chromatin architecture across the entire genome will be generated. In a preferred embodiment, cells will be treated with a GpC methyltransferase enzyme, which will generate a nucleosome footprint by methylating all GpC dinucleotides that are not bound by nucleosomes or tight binding proteins. After this enzymatic treatment, DNA is extracted and bisulfite converted. The resulting bisulfite converted DNA is used to generate a library that will subsequently be used for Solexa sequencing on the Illumina Genome Analyzer. Nucleosome occupancy will be indicated by patches GpC sites, which were protected and thus not methylated by the GpC methyltransferase. Endogenous DNA methylation status will be obtained from the same regions by examining methylation at CpG sites. Combining this data will give the first genome wide-correlation of DNA methylation and nucleosome positioning. Each region of the genome should be examined approximately 4-5× times to give sufficient coverage and ensure reliable and meaningful conclusions.

The approach described herein is significantly better than currently available methods that analyze DNA methylation and protein binding together. Importantly, in the approach described here, the nucleosome and binding protein assay is done in living cells thus providing an accurate, detailed picture in living cells. This is compared to previous methods that determine nucleosome positioning using sonication or micrococcal nuclease digestion that rely on DNA breakage, which can be confounded by cleavage sensitivity of different genomic regions. Thus, commonly used approaches are potentially limited to regions of the genome that are sensitive to sonication or micrococcal nuclease digestion and as a result do not provide a true genome-wide approach.

As a result footprinting based on GpC methylation can be used to interrogate both CpG rich and CpG poor regions. Imprinted regions and X-linked genes are methylated on one allele, thus the positioning of nucleosomes and other binding proteins cannot be examined using the M-SPA method. In the technique described here, endogenous methylation is obtained from the same DNA strand that is used for footprinting of nucleosome and binding proteins thus making it possible to correlate mono-allelic gene expression with specific chromatin structures. The use of the GpC methyltransferase method overcomes the limitations of M-SPA and can be used to generate an integrated view of methylated and unmethylated regions, CpG rich and CpG poor regions, imprinted and X-linked genes at the single molecule level, which has not been possible up until this point.

The epigenetic landscape generated by the combined DNA methylation analysis and nucleosome and binding protein footprint will have several important implications for biology. The findings will provide valuable insight into epigenetic changes that occur during a variety of diseases, including cancer. This technique makes it possible to identify specific chromatin structures that are correlated with particular disease states and progression. Furthermore, this combined analysis can lead to the identification of new drug targets and footprints can be generated as a way to monitor a patient's response to treatment. The use of single molecule sequencing is specifically important for disease related changes. It allows the analysis single nucleotide polymorphisms (SNPs), which often predispose an individual to a disease. The presence of specific SNPs can be correlated with a particular chromatin structure or methylation level or pattern and the susceptibility to specific diseases.

BRIEF DESCRIPTION OF THE FIGURES

FIG. 3 shows images of cells before and after lysis of the cell membrane. (A) Microscopic image of cells prior to lysis of the cell membrane. (B) Microscopic image of cells after lysis of the cell membrane by incubation with NP-40.

FIG. 4 is a schematic for the bisulfite conversion of DNA. During bisulfite treatment of DNA all unmethylated cytosines (C) are converted into uracils (U). All methylated cytosines remain unchanged. After the first PCR amplification cycle the U's are complemented with A's (adenine) in the antisense strand and the methylated C's are complemented with G's (guanine). Then after subsequent rounds of PCR the U's in the sense strand become T's (thymidine) and the methylated C's in the sense strand remain C's. Therefore, during the whole process unmethylated C's become T's and methylated C's remain C's.

FIG. 8 shows that DNA methylation silences the L1-MET promoter. A. Map of the CpG sites (represented by the lower tick marks) within the L1-MET anti-sense promoter (ch7: 116364010-116364564), which was ligated into a CpG-less luciferase vector (pCpGL) in both orientations, allowing for the measurement of either L1-MET activity (red bars) or L1 activity (black bars). B. The relative luciferase activity (firefly luciferase light units/Renilla luciferase light units) is represented as the mean+/−SD and was high in the untreated vector, the methyl donor S-adenosyl-methionine (SAM) alone, and the CpG methyltransferase (SssI) alone. When the methyltransferase enzyme and the methyl donor (SssI+ SAM) were added to the luciferase vectors together then promoter activity was silenced in both directions. The values are the average of three biological replicates. Error bars represent the standard deviation.

FIG. 23 shows the methylation of specific L1s across the bladder. (A) Tissue samples were taken from five patients with their tumors (red, T) and at increasing distances from the tumor (0.5 to 2 cm) in the surrounding normal-appearing tissue in multiple directions (light blue, a to d). Additionally, distant normal-appearing samples were taken at least 5 cm from the tumor (dark blue, C). (B) Methylation at L1-ACVRIC and (C) L1-RAB3IP was measured by pyrosequencing. The green line represents the mean methylation of 12 normal samples from cancer-free patients. While there are no error bars for the clinical sample analysis due to the extremely limited amount of sample DNA. the results show a consistent trend. Found at: doi:10.1371/journal.pgen. 1000917.s010 (1.62 MB TIF)

Figure 1:
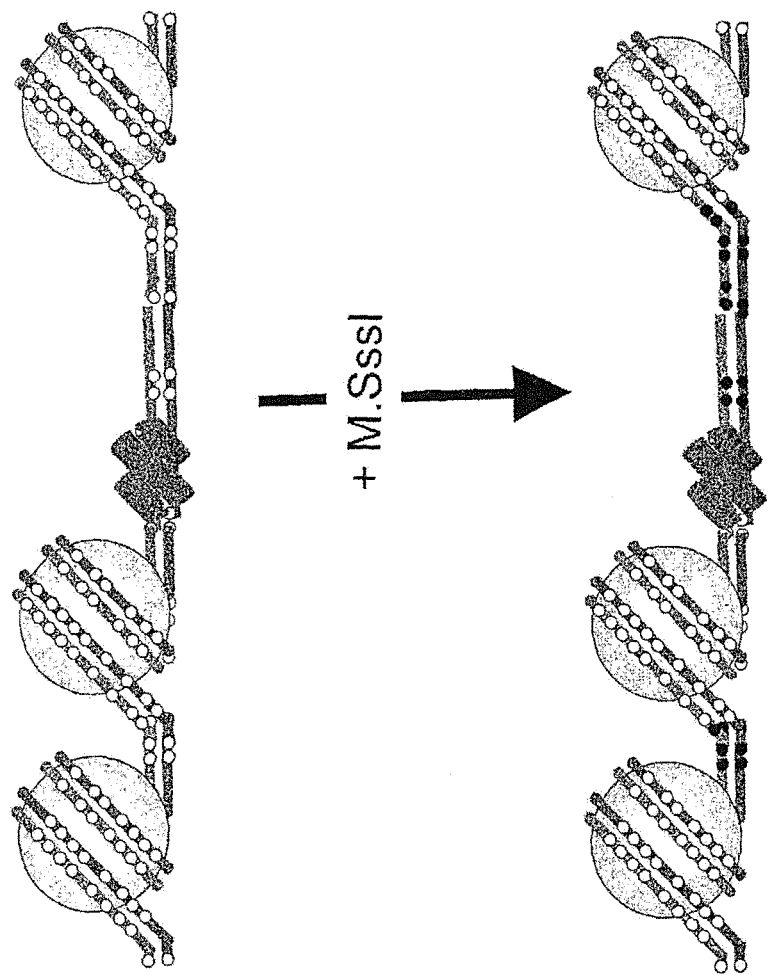
FIG. 1 shows the schematic of M.SssI footprinting. First chromatin is treated with M.SssI. This enzyme methylates all CpG sites in purified DNA, but it cannot methylate the same sites when they are assembled into nucleosomes or are associated with tight binding factors. Next the DNA is purified, the sequences are bisulfite converted and individual molecules are cloned. Patches which are inaccessible to M.SssI are revealed. Red circles indicate CpG sites that are methylated and white circles indicate sites that are unmethylated.
Figure 1:
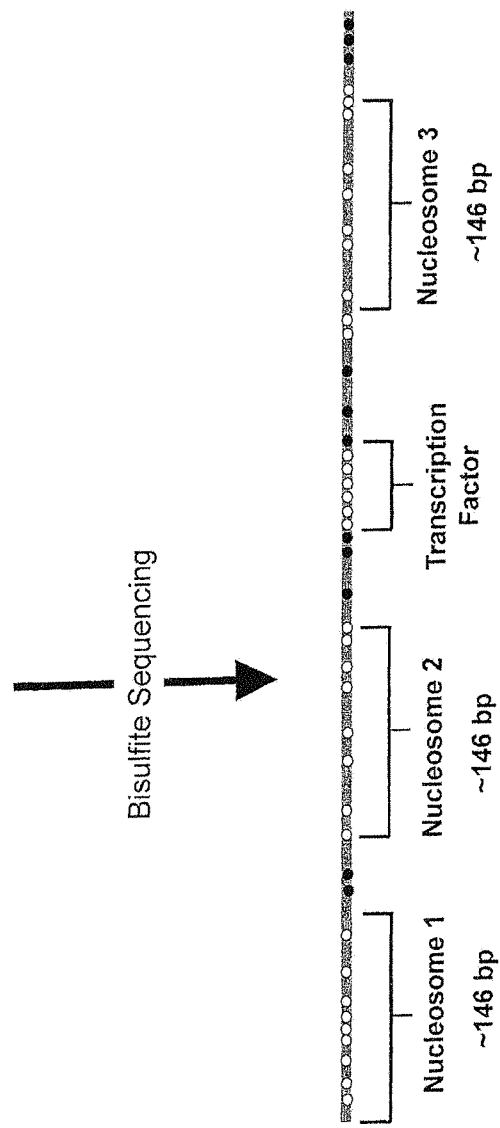

We found variable chromatin configurations surrounding specific transcription factor binding sites. (A) At AP-1 binding sites there is low levels of DNA methylation and nucleosome depletion, while at (B) NF1 binding sites there is also a dip in DNA methylation levels but the sites are nucleosome occupied. (B) At E2F binding sites there is a peak in methylation that corresponds to nucleosome occupancy. Interestingly, at CREB binding sites there is a peak in DNA methylation that corresponds to a dip in nucleosome occupancy.

DETAILED DESCRIPTION OF THE INVENTION

Unless otherwise indicated, all terms used herein have the meanings that the terms would have to those skilled in the art of the present invention. Practitioners are particularly directed to Alberts et al., (2008) Molecular Biology of the Cell (Fifth Edition (Reference Edition)) Garland Science, Taylor & Francis Group, LLC, for definitions and terms of the art. It is to be understood that this invention is not limited to the particular methodology, protocols, and reagents described, as these may vary.

The term "CpG site" refers to a region of DNA where a cytosine nucleotide occurs next to a guanine nucleotide in the linear sequence of bases along its length, 5' . . . CG . . . 3'. "CpG" is shorthand for "-C-phosphate-G-", that is, cytosine and guanine separated by a phosphate, which links the two nucleosides together in DNA. The "CpG" notation is used to distinguish this linear sequence from the CG base paring of cytosine and guanine.

A "GpC site" refers to a region of DNA where a guanine nucleotide occurs next to a cytosine nucleotide in the linear sequence of bases along its length, 5' ... GC ... 3' "GpC" is shorthand for "-G-phosphate-C-", that is, cytosine and guanine separated by a phosphate, which links the two nucleosides together in DNA. The "GpC" notation is used to distinguish this linear sequence from the CG base paring of cytosine and guanine.

The method for genome-wide methylation-sensitive chromatin structure determination of the present invention includes a step of providing eukaryotic cells with nuclei comprised of chromatin, wherein the chromatin is comprised of nucleosomes having DNA associated with histones and also optionally associated with one or more tight-binding factors. The type of eukaryotic cells is not particularly limited. The eukaryotic cells may be mammalian or non-mammalian eukaryotic cells. In a preferred embodiment, the cells are mammalian cells, and, more preferably, human cells. The cells may be a cell type or population associated with a disease state or they may be so-called "normal cells," i.e. cells not typically associated with a disease state. Preferably, the eukaryotic cells having a GpC frequency and distribution substantially the same as human cells. Preferably, the GpC sites of the cells are not endogenously methylated.

Preferably, the methods and kits of the present invention are directed to genome-wide methylation-sensitive chromatin structure determination. However, the methods and kits of the present invention may also be used for methylation-sensitive chromatin structure determination of a subset of the genome. Specifically, the structure of certain subsets of the genome may be enriched by known methods, and the structure of these enriched genomic subsets may be analyzed as described herein. For instance, the genomic DNA may be treated with a restriction enzyme according to known methods and the restriction fragments may be analyzed separately. Further, treatment with antibodies according to known methods may be used to enrich the antibody binding region of the genome. For instance, an antibody to methylated DNA may be used to generate a footprint of the subset of the genome that is methylated.

Nuclei Extraction

The method for genome-wide methylation-sensitive chromatin structure determination of the present invention includes a step extracting the nuclei of the cells provided.

Preferably, the cells containing the chromatin structure to be analyzed are first trypsinized. Trypsinization is the process of using trypsin, a proteolytic enzyme which breaks down proteins, to dissociate adherent cells from the vessel in which they are being cultured. In general, when added to a cell culture, trypsin breaks down the proteins which enable the cells to adhere to a vessel, flask or container in which the cells have been cultivated in containers that take the form of plastic flasks or plates. Trypsin "digests" the proteins that facilitate adhesion to the container and between cells. For instance, in connection with the present invention, the actively growing cells are trypsinized and washed once with cold phosphate buffer saline (PBS). In a preferred embodiment, 250,000 cells per reaction are used and done in duplicate. An untreated control is preferably also run. It should be noted that other methods known to those of ordinary skill that dissociate adherent cells from the vessel used to cultivate the cell may be used, so long as the nuclei of the cells are not significantly altered in the process.

Preferably, the step of extracting the nuclei includes a step of separating the nuclei of the cells from the other cytoplasmic contents of the cell. In general, any method for separating the cellular nuclei from the cytoplasmic content may be used so long as the chromatin remains substantially unaltered. In a preferred embodiments, the cells are lysed with cytoplasmic membrane lysing agent, which a lysing agent that is not powerful enough to break the nuclear membrane, but can break the cytoplasmic membrane. As such, cytoplasmic membrane lysing agent can be used to separate the cytoplasmic contents of the cells from the nuclei. In a preferred embodiment, the cytoplasmic cell lysing agent is NP-40, is a commercially available detergent, Tergitol-type NP-40 (nonyl phenoxypolyethoxylethanol).

The nuclei may then be separated by known techniques, for instance, by centrifugation. Preferably, the nuclei are then washed first in a wash buffer, as described herein. The sells may also be washed, depending on the application in either a RSB Buffer+Sucrose wash or a RSB Buffer+Sucrose+0.4M NaCl wash (salt wash to eliminate tight binding transcription factors). In a typical procedure, 250,000 cells per 100 ul are used.

Methylating Substantially all the GPC Sites

The method for genome-wide methylation-sensitive chromatin structure determination of the present invention includes a step of (and the associated method for) methylating substantially all of the GpC sites not associated with the nucleosomes and also, in a preferred embodiment, GpC sites not associated with tight-binding factors. The step of methylating substantially all of the GpC sits preferably includes contacting the cellular nuclei with a GpC methylating reagent. The GpC methylating reagent preferably comprises a methyl transfer agent, lysing prevention agent and an effective amount of a GpC methyltransferase. In a preferred embodiment, the GpC methylating reagent further comprises a buffer.

A suitable GpC methyltransferase is one that is capable of methylating all cytosine residues ($C^5$) within the double-stranded dinucleotide recognition sequence 5' ... GC ... 3' that are not associated with a nucleosome or a tight binding factor. The methylation site of the GpC methyltransferase according to the present invention is:

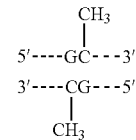

One suitable GpC methyltransferase useable in connection with the present invention is M.CviPI. M.CviPI, is isolated from a strain of *E. coli* which contains the methyltransferase gene from *Chlorella* virus. This construct is fused to the maltose binding protein (MBP). M.CviPI is commerically available from New England Biolabs.

The use of a GpC methyltransferase is especially advantageous since GpC sites are not methylated in humans except in the context of the sequence 5' ... GpCpG ... 3'. As such, so called "GpCpG sites" should generally be excluded from analysis since it is not possible to distinguish between endogenous CpG methylation and enzyme-induced GpC methylation at such loci. The limited number and location of endogenous CpG sites limits the resolution of prior methods based on CpG methyltransferase. Therefore, the GpC methyltransferase based reagents allowed an increased resolution over prior CpG methyltransferase based reagents.

The DNA in the nuclei used in connection with the present invention may be associated with nucleosomes or tight-binding factors. A "GpC accessible site" is a GpC site that is capable of being methylated by the GpC methyltransferase. A "GpC inaccessible site" is a site that is not capable of being methylated by the GpC methyltransferase because the GpC site is protected by (or associated with) either a nucleosome, or alternatively, a tight binding factor. In connection with the present invention, the GpC inaccessible sites thus provide a "footprint" of the position of the nucleosome and/or the tight binding factors in the chromatin.

In one embodiment of the invention, the methods and kits of the present invention may be used to identify only the footprints of nucleosomes and not tight binding factors. Specifically, tight binding factors may be removed by use of a salt wash, for instance a wash that contains 0.4M NaCl. It should be noted that nucleosomes can be made of different types of histones. The stability of the nucleosomes depends on which types of histones are in the nucleosome. Under certain conditions, the salt wash may eliminate both the transcription factors and less stable nucleosomes. The resulting footprint would include the more stable nucleosomes. However, by comparing the size of the GpC inaccessible region before and after salt treatment, one of ordinary skill can determine whether the salt treatment washed out a transcription factor or an unstable nucleosome.

The methods and kits of the present invention require that the GpC methylating reagent comprise an effective amount of the GpC methyltransferase and methyl donating agent. An "effective amount" necessary is an amount necessary to methylate substantially all the GpC accessible sites under the reaction (alternatively referred to as "incubation") conditions. For purposes of the invention, an effective amount of the GpC methylating reagent is an amount required to methylate at least 80%, more preferably 90% and most preferably 99% of the GpC accessible sites.

It is important incubation conditions and the amount of GpC methyltransferase used be sufficient to methylate substantially all the GpC accessible sites, but also sufficiently low to avoid substantial methylation of the GpC inaccessible sites (for example, less than 20% of the GpC inaccessible sites). Methylating substantially all the GpC accessible sites means to methylate at least 80%, more preferably 90% and most preferably 99% of the GpC accessible sites. Avoiding substantial methylation of the GpC inaccessible sites means methylating less than at least 20%, more preferably 10% and most preferably 1% of the GpC inaccessible sites. The amount of the GpC methylating and methyl donating agent and the incubation conditions may vary according to cell type. Validation that substantially all the GpC sites are methylated but not the GpC inaccessible sites may be done in accordance with the examples (including the protocols) described herein.

Preferably, the amount of the GpC methyltransferase is between about 50 and 500 U (U=Units, and one unit is defined as the amount of enzyme required to protect 1 µg of lambda DNA in a total reaction volume of 20 µl in 1 hour at 37° C. against cleavage by HaeIII restriction endonuclease). More preferably, the amount of the GpC methyltransferase is about 100 U.

It is possible that the total amount of GpC methyltransferase may be added in more than one aliquot. For instance, human fibroblasts treated with different amounts of M.CviPI. Both GRP78 and MLH1 are expressed (and thus should have a nucleosome after the TSS and a nucleosome depleted region (NDR) before the transcription start site (TSS). Accurate footprinting of MLH1 was obtained using 100 U of M.CviPI, however accurate footprinting of the NDR of GRP78 required the 200 U+100 U M.CviPI condition. The 200 U+100 U condition also accurately footprinted the MLH1 promoter. MYOD1 and LAMB5 are not expressed in human fibroblasts and are occupied by nucleosomes. The 200+100 condition did not result in aberrant accessibility at these promoters. Combining these results shows that 200+100 Units of enzyme can accurately footprint accessible promoters without leading to aberrant GpC methylation of inaccessible promoters. A footprint derived from the CpG methyltransferase enzyme, M.SssI, can be used as a positive control for GRP78, MLH1 and MYOD1 and endogenous methylation is shown for LAMB5.

The GpC methylating reagent preferably includes at least one methyl transfer agent. Generally, any methyl transfer agent that is reactive under the GpC methylation conditions and results in the donation of a methyl group ($CH_3$) a to the GpC cite of the acceptor DNA may be used. In an especially preferred embodiment, the methyl transfer agent is s-adenosyl methionine (SAM, (2S)-2-Amino-4-[[(2S,3S,4R,5R)-5-(6-aminopurin-9-yl)-3,4-dihydroxyoxolan-2-yl]methyl-methylsulfonio]butanoate). Validation of a methyl transfer agent for use in connection with the methods and kits of the present invention may be accomplished by comparison of results using SAM with results using a candidate methyl transfer agent under analogous conditions as would be understood by a person of ordinary skill in the art.

The GpC methylating reagent also preferably includes a lysis prevention agent that prevents lysis of the nuclear membrane of the nuclei under the enzyme conditions necessary for optimal methyl transfer. Without being limited to theory, it is believed that the lysis prevention agent adjusts the viscosity of the reaction media that permits the use of concentrations GpC methyltransferase necessary for efficient methyl transfer to the GpC sites but substantially reduces the lysis of the nuclear membranes. In a preferred embodiment, the lysis prevention agent is sucrose. Validation of a lysis prevention agent for use in connection with the methods and kits of the present invention may be accomplished by comparison of results using sucrose with results using a candidate methyl transfer agent under analogous conditions as would be understood by a person of ordinary skill in the art.

Following the step of contacting the nuclei with the GpC methylating reagent, methods of the present invention preferably include a step of isolating the DNA of the nuclei from the other components of the nuclei. Any known method of isolating the DNA may be used so long as it does not substantially affect the methylation state or sequence of the DNA. In a preferred embodiment, the cells are treated with proteinase K, and the DNA is purified by phenol/chloroform extraction and ethanol precipitation.

Bilsulfite Conversion

The method for genome-wide methylation-sensitive chromatin structure determination of the present invention includes a step of bisulfate conversion of the DNA that has been subject to the methylating step. The bisulfite conversion reaction was first described in 1980 as a method for distinguishing between cytosine and 5-methylcytosine (5mC) in DNA (Wang et al., 1980; FIG. 4). In this reaction, denatured DNA is first treated with sodium bisulfite to convert cytosine residues to uracil, under conditions such that 5mC remains essentially non-reactive. The DNA sequence of interest is then amplified by PCR with primers specific for bisulfite modified DNA. This leads to the replacement of the converted uracil residues to thymidine residues. Therefore, during sequencing of the bisulfite converted DNA, the unmethylated cytosines appear as thymidine residues. Before bisulfite conversion the genomic DNA should be digested with restriction enzymes, which cut outside the sequence to be cloned. (Note: Bisulfite conversion can be done without cleavage of the DNA, but this may lead to insufficient conversion of some sequences).

Bisulfite Conversion in according to the present invention can be done using methods known to those of ordinary skill in the art. Preferably, the methylated GpC sites are subjected to bisulfite conversion using standard methods or commercially available kits, such as the EZ DNA Methylation Kit, Cat. Nos. D5001 and D5002, available from Zymo Research.

The method for genome-wide methylation-sensitive chromatin structure determination of the present invention includes a step sequencing the DNA.

The step of sequencing the DNA preferably includes a step of shearing the DNA. The DNA may be sheared according to methods known to those of ordinary skill in the art. These include Mnase Digestion, Sonication, Nebulization and Restriction Digestion. The sheared DNA results in a library of DNA fragments that may be sequenced, after the library has been suitably prepared.

Once sheared, the DNA library may be prepared for sequencing according to known methods. One method of preparing the DNA library for use in massively parallel sequencing includes steps of End-repair, addition of an 'A' Base to the 3' end of the DNA fragments, ligation of adapters to the ends the DNA fragments, gel purification of the products from the ligation reaction, and enrichment of the adapter-modified DNA fragments by PCR as known to those of ordinary skill in the art.

Sequencing and Analysis

The prepared DNA library may then be sequenced by known sequencing techniques, including massively parallel sequencing of the fragment library, preferably Solexa sequencing on the Illumina Genome Analyzer. Other suitable sequencing platforms include 454 sequencing, SOLiD; however these require a different library preparation protocol, which protocols are well-known to those of skill in the art.

In another embodiment, paired end libraries were prepared from 5 ug of DNA as previously described {Lister, 2009; Kelly, 2010} to generate 76 bp reads. Briefly, M.CviPI treated DNA is END repaired (Epicenter), methylated adaptors ligated (Illumina), bisulfite converted (Zymo EZ DNA methylation) and subject to 6 cycles of PCR and size selection by gel purification. Clusters were generated following Illumina protocols and the resulting library was sequenced on Illumina Hi-seq.

Using the GpC methyltransferase enzyme in accordance with the methods and kits of the present invention enables the examination of both nucleosome positioning and endogenous CpG methylation within the same DNA molecule. In addition to being able to generate an integrated map of DNA methylation and positioning of nucleosomes and other binding proteins, the use of the GpC methyltransferase overcomes the limitations of CpG methyltransferase based footprinting, as there is no endogenous GpC methylation, and GpC are comparably more abundant in the genome than CpG sites.

Using next-generation sequencing combined with the GpC footprinting methodology as described herein, an integrated view of DNA methylation and chromatin architecture across the entire genome can be generated. Endogenous DNA methylation status will be obtained from the same regions by examining methylation at CpG sites. Combining this data provides the first genome wide-correlation of DNA methylation and nucleosome positioning. Each region of the genome should be examined approximately 2-10× times to give sufficient coverage and ensure reliable and meaningful conclusions.

The approach described herein is significantly better than currently available methods that analyze DNA methylation and protein binding together. Importantly, in the approach described herein, the nucleosome and binding protein assay is done concurrently in living cells thus providing an accurate, detailed picture simultaneously of the methylation state and the nucleosome binding in living cells.

In the technique disclosed herein, endogenous methylation is obtained from the same DNA strand that is used for footprinting of nucleosome and binding proteins thus making it possible to correlate mono-allelic gene expression with specific chromatin structures. The epigenetic landscape generated by the combined DNA methylation analysis and nucleosome and binding protein footprint has several important implications for biology. The findings may provide valuable insight into epigenetic changes that occur during a variety of diseases, including cancer. This technique makes it possible to identify specific chromatin structures that are correlated with particular disease states and progression. Furthermore, this combined analysis can lead to the identification of new drug targets and footprints can be generated as a way to monitor a patient's response to treatment. The use of single molecule sequencing is specifically important for disease related changes. It allows the analysis single nucleotide polymorphisms (SNPs), which often predispose an individual to a disease. The presence of specific SNPs can be correlated with a particular chromatin structure or methylation level or pattern and the susceptibility to specific diseases.

Another aspect of the present invention is directed to a kit for genome-wide methylation sensitive chromatin structure determination comprising a cytoplasmic membrane lysing reagent, a GpC methylating reagent, a DNA purifying reagent; and instructions for using the reagents to prepare chromatin DNA for sequencing, wherein, when used as instructed, the endogenous methylation state of the DNA is preserved. The kit may also include one or more of trypsin, a bisulfate conversion reagent. Preferably, when used as instructed, the GpC sites associated with the nucleosomes or tight-binding factors are preserved. The GpC methylating reagent comprises a methyl transfer agent, lysis prevention agent and an effective amount of a GpC methyltransferase, and preferably, a buffer. The kit may also comprise a salt wash together with appropriate instructions, for removing, for instance, tight binding factors.

The instructions included with the kit preferably include instructions on how to use the kit to effectual a method for genome-wide methylation-sensitive chromatin structure determination. The instructions preferably include, for instance, a description of the eukaryotic cells useable in connection with extracting the kit, methods for extracting the nuclei of the cells, and more preferably instruction and protocols for methylating substantially all of the GpC sites of the chromatin not associated with nucleosomes or tight-binding factors. Preferably, the kit also includes instructions and protocols for one or more of purifying the DNA, bisulfite converting the DNA; and sequencing the DNA; wherein the sequencing provides the endogenous methylation state of the DNA and the GpC sites associated with the nucleosomes or tight-binding factors.

Another aspect of the present invention is directed to a kit for genome-wide methylation of substantially all GpC not associated with nucleosomes or other tight-binding factors comprising a cytoplasmic membrane lysing reagent, a GpC methylating reagent comprised of a methyl transfer agent, lysis prevention agent and an effective amount of M. CviPI, and instructions for using the reagents to methylate substantially all of the GpC sites of the nuclei's chromatin not associated with nucleosomes or tight-binding factors, wherein one or more of endogenous DNA CpG methylation status, native chromatin structure and protein binding is preserved.

The following Examples are provided in order to demonstrate and further illustrate certain embodiments and aspects of the present invention and are not to be construed as limiting the scope thereof.

Example I

Genome Wide GpC Methylation and Preparation for Sequencing

A. Genome-Wide Methylation of GpC Sites
Nuclei Extraction
1. Actively growing cells are trypsinized and washed once with cold phosphate buffer saline (PBS). Use 250,000 cells per reaction, done in duplicate. Don't forget untreated control!
2. Resuspend cells in 1 ml per 1 million cells of ice cold Lysis Buffer with NP-40 and keep on ice for 10 min. (Separate into different tubes per condition)

| Lysis Buffer Recipe: | 100 ml: |
|---|---|
| 10 mM Tris (pH 7.4) | 1 ml 1M Tris |
| 10 mM NaCl | 1 ml 1M NaCl |
| 3 mM MgCl2 | 300 ul 1M MgCl2 |
| 0.1 mM EDTA | 20 ul 0.5M EDTA |
| 0.5% NP-40 | 5 ml 10% NP-40 (2 ml in 18 ml H2O) |
| | 92.68 ml H2O |

The following steps are all done at 4° C.:
3. Centrifuge for 5 min at 3000 rpm at 4° C. The supernatant is discarded.
4. Nuclei are then resuspended in 1 ml per 1 million cells of Wash Buffer. Samples are then centrifuged for 5 min at 3000 rpm at 4° C. The supernatant is discarded.

| Wash Buffer Recipe: | 100 ml: |
|---|---|
| 10 mM Tris (pH 7.4) | 1 ml 1M Tris |
| 10 mM NaCl | 1 ml 1M NaCl |
| 3 mM MgCl2 | 300 ul 1M MgCl2 |
| 0.1 mM EDTA | 20 ul 0.5M EDTA |
| | 97.68 ml H2O |

(Optional) 5. Nuclei are then washed again w/ either RSB Buffer+Sucrose or RSB Buffer+Sucrose+0.4M NaCl (salt wash to eliminate tight binding transcription factors). Use 100 ul per 250,000 cells. Incubate on ice 2 minutes. Dilute out salt before spinning by adding RSB Buffer+Sucrose up to 1 ml. Centrifuge for 5 min at 3000 rpm at 4° C. Discard supernatant.

| RSB Buffer + Sucrose: | 100 ml: | RSB Buffer + Sucrose + NaCl: | 100 ml: |
|---|---|---|---|
| 10 mM Tris pH 7.4 | 1 ml 1M | 10 mM Tris pH 7.4 | 1 ml 1M |
| 10 mM NaCl | 1 ml 1M | 0.4M NaCl | 40 ml 1M |
| 3 mM MgCl2 | 300 ul 1M | 3 mM MgCl2 | 300 ul 1M |
| 0.3M Sucrose | 30 ml 1M | 0.3M Sucrose | 30 ml 1M |
| | 67.7 ml H2O | | 28 ml H2O |

Centrifuge at 3,000×g for 5 min.
6. The nuclei are then resuspended in 1×M.SssI buffer or M.GpC buffer (comes as 10× so dilute 1:10) so that there are 250,000 nuclei per 76.75 μl for SssI, or 64.25 ul for GpC.
Methyltransferase Treatment (for CpG Sites)
M.SssI treatments of nuclei are done immediately after nuclei are prepared.
1. For M.SssI treatment of 250,000 nuclei add the following to an eppendorf tube:

| 10X M.SssI buffer | 15 μl |
|---|---|
| 32 mM SAM | 0.75 μl |
| 1M Sucrose | 45 μl |
| Nuclei (6 μg DNA) | 76.75 μl |
| M.SssI (NEB) | 12.5 μl (50 U) |
| | 150 ul |

Incubate at 37° C. for 15 mins
For GpC Methyltransferase treatment of 250,000 nuclei add the following to an eppendorf tube:

| 10X M.GpC buffer | 20.5 μl |
|---|---|
| 32 mM SAM | 2.5 μl |
| 1M Sucrose | 150 μl |
| Nuclei (6 μg DNA) | 250 μl |
| M.GpC (NEB) | 50 μl (200 U) |
| | 500 ul |

Incubate at 37° C. for 7.5 mins
Add:

| 32 mM SAM | 2.5μ |
|---|---|
| M.GpC (NEB) | 25 μl (100 U) |

Incubate at 37° C. for 7.5 mins
2. Add an equal volume of stop solution (500 μl). Prewarmed at 37° C. to eliminate precipitates.

| Stop Solution (2X Lysis Buffer) | 100 ml: |
|---|---|
| 20 mM Tris-HCl, pH 7.9 | 2 ml 1M Tris |
| 600 mM NaCl | 60 ml 1M NaCl |
| 1% SDS | 10 ml 10% SDS |
| 10 mM EDTA | 2 ml 0.5M EDTA |
| | 26 ml H2O |

3. Incubate with 200 μg/ml proteinase K at 55° C. for 16 h. (3 ul 20 mg/ml)
4. DNA is purified by phenol/chloroform extraction and ethanol precipitation. Do not use phase lock tubes as sucrose interferes.
Proceed with bisulfite Conversion for Genome Wide Sequencing.

B. Bilsulfite Conversion

Bisulfite Conversion can be done using different methods Preferably, the methylated GpC sites are subjected to bisulfite conversion using the EZ DNA Methylation Kit, Cat. Nos. D5001 and D5002, available from Zymo Research.

C. Shearing DNA

The DNA may be sheared according to methods known to those of ordinary skill in the art. These include Mnase Digestion, Sonication, Nebulization and Restriction Digestion. The sheared DNA results in a library of DNA fragments that may be sequenced, after the library has been suitably prepared.

D. Prepare Library for Sequencing

Once sheared, the DNA library may be prepared for sequencing according to known methods. One method of preparing the DNA library for use in massively parallel sequencing is as follows:

ChIP-Solexa Library Preparation

1. End-Repair

Reagent: End-It DNA End-Repair Kit (Epicenter Cat. No. ER0720)

Quantify ChIP DNA and WCE by Picogreen. Use 3-20 ng as starting materials in 34 μl of water (RNase-free, DNase-free) or 10 mM Tris (EB). DNA ends are repaired to blunt ends by T4 DNA polymerase and phosphorylated at 5' ends by T4 Polynucleotide Kinase.

|  | ml |
| --- | --- |
| DNA | 34 |
| 10X End-repair Buffer | 5 |
| 2.5 mM dNTPs | 5 |
| 10 mM ATP | 5 |
| END-IT enzyme mix | 1 |
| Total vol. | 50 |

Incubate for 45 min at room temperature.
Minelute purification (Qiagen). Elute in 20 μl of EB, elute again with 12 μl.

2. Addition of an 'A' Base to the 3' End of the DNA Fragments (Step 4 of Illumina Genomic DNA Prep Kit Protocol)

|  | ml |
| --- | --- |
| DNA from section 1 | 32 |
| 10X Klenow Buffer | 5 |
| 1 mM dATP | 10 |
| Klenow (3'-5' exo-) (5U/ul) | 3 |
| Total vol. | 50 |

Incubate for 30 min. at 37 C.
Minelute purification. Elute in 10 μl of EB twice. Speedvac to 4 μl.

3. Ligation of Adapters to the Ends of the DNA Fragments

| 15 ng-50 ng starting DNA scale | ml |
| --- | --- |
| DNA from section 2 | 4 |
| 2X Ligase Buffer | 5 |
| Adapter Oligo mix (1:10 in H2O) | 0.5 |
| DNA Ligase (1 U/ml) | 0.5 |
| Total vol. | 10 |

Incubate for 15 min. at room temperature.
**** Minelute purification to eliminate unligated adapters. Elute in 10 μl of EB twice.

4. Gel Purification of the Products From the Ligation Reaction

** To remove remaining unligated adapters, adapters that may have ligated to each other, and select a size-range of templates to go on the sequencing platform. Purify up to 2-3 samples on a single gel to prevent cross-contamination. Often materials will not be enough to be visualized under UV, load ladder on both sides of the sample to estimate the size of desired fragments to be isolated.

Prepare 2% agarose (Biorad cat#161-3106) gel in a final volume of 100 ml 1×TAE buffer (Biorad cat#161-0743). Add the ethidium bromide (Sigma cat#E1510) to achieve 400 ng/ml final concentration.

Add 3 μl of loading buffer (50 mM Tris pH8.0, 40 mM EDTA, 40% (w/v) sucrose) to 8 μl of the ladder (NEB cat#N3233L) and load all to the gel. Add 12 μl of loading buffer to the DNA from section 3 (40 μl). Load all DNA and leave one empty lane between ladder and sample.

Run gel at 120V for 60 min.
Excise bands from 275 bp to 700 bp with a clean scalpel.
Purify DNA from agarose gel using Gel Extraction kit (Qiagen). Elute in 23 μl of EB twice. Use 23 μl for the PCR reaction.

5. Enrichment of Adapter-Modified DNA Fragments by PCR

|  | ml |
| --- | --- |
| DNA from section 4 | 23 |
| 2X Phusion DNA polymerase (Finnzymes) | 25 |
| PCR primer 1.1 | 1 |
| PCR primer 2.1 | 1 |
| Total vol. | 50 |

Amplify using the following PCR protocol
30 sec at 98 C
[10 sec at 98 C, 30 sec at 65 C, 30 sec at 72 0] 18 cycles
5 min at 72 C
Hold at 4 C Clean up with QIAquick PCR purification Kit (Qiagen). Elute in 30 μl twice.

Quantify with Picogreen. Run at least 80 ng of library on agarose gel to check the size of the library.

Sequencing and Analysis

The prepared DNA library may then be sequenced by known sequencing techniques, including massively parallel sequencing of the fragment library, preferably Solexa sequencing on the Illumina Genome Analyzer. Other suitable sequencing platforms include 454 sequencing, SOLiD; however these require a different library preparation protocol, which protocols are well-known to those of skill in the art.

Using the GpC methyltransferase enzyme in accordance with the methods and kits of the present invention enables the examination of both nucleosome positioning and endogenous CpG methylation within the same DNA molecule. In addition to being able to generate an integrated map of DNA methylation and positioning of nucleosomes and other binding proteins, the use of the GpC methyltransferase overcomes these limitations as there is no endogenous GpC methylation, and GpC are comparably more abundant in the genome than CpG sites.

Using next-generation sequencing combined with the GpC footprinting methodology as described herein, an integrated view of DNA methylation and chromatin architecture across the entire genome will be generated. Endogenous DNA methylation status will be obtained from the same regions by examining methylation at CpG sites. Combining this data will give the first genome wide-correlation of DNA methylation and nucleosome positioning. Each region of the genome should be examined approximately 4-5× times to give sufficient coverage and ensure reliable and meaningful conclusions.

The approach described herein is significantly better than currently available methods that analyze DNA methylation and protein binding together. Importantly, in the approach described here, the nucleosome and binding protein assay is done in living cells thus providing an accurate, detailed picture in living cells.

In the technique disclosed herein, endogenous methylation is obtained from the same DNA strand that is used for footprinting of nucleosome and binding proteins thus making it possible to correlate mono-allelic gene expression with specific chromatin structures. The epigenetic landscape generated by the combined DNA methylation analysis and nucleosome and binding protein footprint will have several important implications for biology. The findings will provide valuable insight into epigenetic changes that occur during a variety of diseases, including cancer. This technique makes it possible to identify specific chromatin structures that are correlated with particular disease states and progression. Furthermore, this combined analysis can lead to the identification of new drug targets and footprints can be generated as a way to monitor a patient's response to treatment. The use of single molecule sequencing is specifically important for disease related changes. It allows the analysis single nucleotide polymorphisms (SNPs), which often predispose an individual to a disease. The presence of specific SNPs can be correlated with a particular chromatin structure or methylation level or pattern and the susceptibility to specific diseases.

Example II

Figure 2:
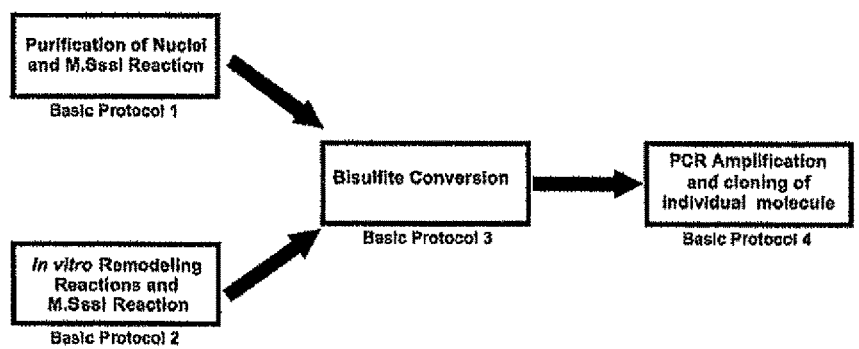
FIG. 2 is a schematic of the protocols according to one embodiment of the present invention. The procedure can start with basic protocol 1, which describes nuclei purification and treatment of nuclei with M.SssI, or with basic protocol 2, which discusses in vitro remodeling and treatment of the remodeled products with M.SssI. These two protocols are then followed by bisulfite conversion (basic protocol 3) and PCR amplification and cloning of individual molecules (basic protocol 4).

Methylation-sensitive Single-molecule Analysis of Chromatin Structure and Associated Protocols Disclosed are four different basic protocols (FIG. 2) used in connection with methods for the study of chromatin structure in purified nuclei and remodeled reconstituted nucleosomes. Either purified nuclei or remodeled mononucleosomes are treated with the CpG-specific DNA methyltransferase SssI (M.SssI). They are presented herein, at least in part, as guidance for those of ordinary skill in the art in adapting the methods of the present invention to the use of various cells and methyltransferase reagents, including GPC methyl transferase, useable in connection with the present invention. Although certain of the protocols describe protocols specific to M.SssI DNA methyltransferase, a CpG methyltransferase, the protocols herein provide general procedures and guidance for extending the protocols to other systems.

The first two basic protocols represent two different preparations of starting material. If the goal is to study chromatin structure in vivo then basic protocol 1 should be referred to. This protocol describes the purification of nuclei followed by the treatment of the nuclei with the M.SssI DNA methyltransferase to obtain a high resolution footprint. If the objective is to study how a specific chromatin modifier affects chromatin structure in vitro, then basic protocol 2 should be used. This section describes how to perform the remodeling reaction followed by treatment of the remodeled products with M.SssI. Basic protocol 3 presents two conventional bisulfite conversion methods and lists some commercially available kits. Basic protocol 4 presents strategies for primer design and PCR amplification, followed by recommended sequence analysis programs.

Although these protocols are meant to work together to determine nucleosomal DNA accessibility at, for instance, unmethylated CpG islands or on reconstituted nucleosomes, the last two sections can also function together as independent methods. Bisulfite conversion is a popular technique used in the studying of CpG methylation. PCR amplification of the converted DNA is widely used after bisulfite conversion and can be followed by sequencing, Ms-SNuPE (Gonzalgo and Jones, 1997; Gonzalgo and Liang, 2007), and pyrosequencing (Tost et al., 2003) for the analysis of endogenous DNA methylation.

Also described herein in Part II are methods for the study of chromatin structure in purified nuclei and remodeled reconstituted nucleosomes. Either purified nuclei or remodeled mononucleosomes are treated with the CpG-specific DNA methyltransferase SssI (M.SssI), followed by bisulfite sequencing of individual progeny DNA molecules (FIG. 1; Fatemi et al., 2005, Gal-Yam et al., 2006, Lin et al., 2007, Bouazoune et al, 2009). The basis for this method comes from the observation that CpG sites within DNA are protected from methylation when these sequences are wrapped around histones or tightly bound by transcription factors. This method provides single molecule resolution over a gene promoter or reconstituted nucleosomes under conditions in which the physical linkage between nucleosomes and/or the tight binding of transcription factors are maintained.

Introductory Comments

Nucleosome positioning plays a pivotal role in the regulation of transcriptional initiation (torch et al., 1987; Studitsky et al., 1995; Workman and Kingston, 1998). Transcriptional co-activator complexes are recruited to promoters to induce chromatin rearrangements. Transcriptional initiation often requires re-positioning or disassembling nucleosomes near the transcription start site (Tsukiyama et al., 1994, Lomvardas and Thanos 2001; Lusser and Kadonaga, 2003; Boeger et al., 2003; Studitsky et al., 2004; Saeger et al., 2004).

To date, most of the studies investigating nucleosome rearrangements rely on DNA-cleaving reagents such as nucleases (Rando, D. J. and Chang, H. Y. 2009). While very valuable, these approaches are limited to analyzing average DNA accessibility. However, promoters are molecular 'modules', which are controlled as individual entities. When analyzed by conventional methodologies this modularity is destroyed. Therefore we have modified a previously described footprinting strategy (Kladde and Simpson, 1996; Kladde et al., 1996) such that it allows studying the chromatin structure of individual molecules. This method can be used to analyze unmethylated CpG islands in vivo by treatment of cell nuclei with the M.SssI DNA methyltransferase followed by bisulfite sequencing of individual progeny DNA molecules (Fatemi et al., 2005; Gal-Yam et al., 2006; Lin et al., 2007). This single-molecule resolution over the promoter allows for the physical linkage between binding sites on individual promoter molecules to be maintained. Similarly, in vitro-reconstituted nucleosomes, can be probed for changes in nucleosomal DNA accessibility after remodeling using M.SssI to circumvent the limitations of conventional methods, which monitor the remodeled products in bulk.

The in vivo method has been used successfully in mammalian cells to compare nucleosome positioning at the p16 promoter in two cell lines expressing the p16 gene at different levels (Fatemi et al., 2005), to identify transcription factor binding sites and their combinatorial organization during endoplasmic reticulum stress (Gal-Yam et al., 2006), to study changes in nucleosome occupancy that are involved in the silencing of three transcription start sites of the bidirectional MLH1 promoter in cancer cells (Lin et al., 2007), to study how methylation of a 3' promoter-proximal region affects nucleosome positioning at the TATA box (Appanah et al., 2007), and to correlate de novo methylation patterns with nucleosome footprint at the p16 promoter (Hinshelwood et al., 2009). Lastly, the in vitro approach has been used to reveal the heterogeneity of the products created by hSWI/SNF compared to human ISWI-family remodeling factors (Bouazoune et al., 2009).

Summary

Methylation-sensitive single-molecule analysis of chromatin structure is a high-resolution method developed for studying nucleosome positioning. As described, this method allows for the analysis of chromatin structure of unmethylated CpG islands or in vitro-remodeled nucleosomes by treatment with the CpG-specific DNA methyltransferase SssI (M.SssI), followed by bisulfate sequencing of individual progeny DNA molecules. Unlike nuclease-based approaches, this method allows for each molecule to be viewed as an individual entity instead of an average population.

Basic Protocol 1. Treatment of Nuclei with M.SssI

This section first describes a method for purifying nuclei from mammalian cells. Once the nuclei are isolated M.SssI is added to methylate the DNA at CpG sites that are not protected by nucleosomes or tightly bound transcription factors. Proteins are then degraded and genomic DNA is purified.

Materials $10^6$-$10^7$ mammalian cells
PBS (phosphate buffer saline)
RSB Buffer (receive signaling buffer; see recipe)
Nonidet P-40 (NP-40)
1×SssI Buffer (see recipe)
M.SssI+S-Adenosylmethionine (SAM; New England Biolabs)
1 M Sucrose
Stop Solution (2× lysis buffer; see recipe)

Nuclei Extraction

1. Trypsinize (APPENDIX 3F) exponentially growing cells and wash cells once with cold phosphate buffer saline (PBS).

It is recommended to start with at least $10^7$ cells, however, this procedure has been done successfully with $2\times10^5$ cells.

2. Resuspend cells in 1 mL of ice cold RSB buffer and incubate on ice for 10 min.

The following steps are all done at 4° C.

3. Following the 10 min incubation, add 0.1 mL of 10% Nonidet P-40 (NP-40) detergent to the cells and homogenize with 15 strokes of the tight pestle of a Dounce Homogenizer. If less than $10^7$ cells are used then cells can be lysed with NP-40 by pipetting up and down 15 times with a pipette instead of using the dounce homogenizer. Transfer homogenized cells to a 1.5 mL eppendorf tube and spin for 5 min at 800×g at 4° C. Discard supernatant.

4. Resuspend nuclei in 1 mL of RSB buffer. At this time a small aliquot can be checked for intact nuclei and complete lysis of the cellular membrane under a microscope (FIG. 3). (note: Trypan blue can also be used to visualize cell lysis under the microscope.) Centrifuge samples for 5 min at 800×g at 4° C. Discard supernatant.

To remove tight binding transcription factors that may be interfering with the nucleosome footprint, nuclei can be treated with RSB buffer containing 400 mM NaCl for 2 min after the above Step 4. Nuclei are then spun down at 800×g for 5 min and washed once with the standard RSB buffer.

5. Wash nuclei again with either RSB buffer or with 1×M.SssI buffer. (It should be noted that epithelial nuclei tend to lyse during centrifugation if washed with 1×M.SssI buffer, however fibroblast nuclei stay intact with the 1×M.SssI buffer wash. Nuclei lysis is a problem since the structure of the chromatin may not be maintained). Then spin samples for 5 min at 800×g at 4° C. Discard supernatant.

6. Resuspend the nuclei in 1×M.SssI buffer so that there are $10^6$ nuclei per 74.25 µL.

M.SssI Treatments

M.SssI treatments of nuclei are done immediately after nuclei preparation.

(Note: It is recommended that fresh M.SssI is used every time the assay is performed. At a minimum fresh SAM should be used.)

7. For M.SssI treatment of $10^6$ nuclei add the following to an eppendorf tube

| | |
|---|---|
| 10x M.SssI buffer | 15 µL |
| 32 mM SAM | 0.75 µL |
| 1M Sucrose | 45 µL |
| Nuclei $10^6$ (6 µg DNA) | 74.25 µL |
| 60 U M.SssI | 15 µL | plus H$_2$O to get to a 150 µl total volume
Incubate at 37° C. for 15 min.
A no-M.SssI control should also be included to measure endogenous methylation patterns.
Adding 15 µL of 10× buffer results in a final concentration>1×, however, the initial protocol was developed using 15 µL of buffer and works well.
When the procedure is done with a small number of cells the amount of M.SssI used to treat the nuclei is adjusted proportionally, while the reaction volume is kept at 150 µL.

8. Stop reactions by the adding an equal volume of stop solution (150 µL).

9. Incubate samples with 200 µg/mL proteinase K at 55° C. for 16 h.

10. Purify DNA by phenol/chloroform extraction and ethanol precipitation (UNIT 2.1A).

Purified DNA can now be stored at −20° C. for at least 1 year.

Basic Protocol 2. Single Molecule Methylation-Based Analysis of Nucleosomal DNA Accessibility Alterations Catalyzed by Chromatin Remodeling Proteins, In Vitro.

This section describes a method to monitor DNA accessibility on in vitro-reconstituted nucleosomes before and after reactions with nucleosome remodeling factors. This approach allows dissection of the effect of a given (set of) purified protein (s) on nucleosomal DNA accessibility on single molecules and can, in principle, be extended to analyzing any factor acting on chromatin. In this section, the optimal M.SssI concentration necessary to efficiently methylate a chosen nucleosomal template is determined in conditions analogous to a nucleosome remodeling reaction. Next, the nucleosome remodeling conditions are optimized. Then remodeling of the nucleosomal template is performed and the remodeled templates are methylated using the optimized conditions. Finally, the remodeled products are gel-purified and subjected to a bisulfite conversion procedure in order to map the sites of methylation and infer changes in DNA accessibility.

Materials

NRB (Nucleosome remodeling buffer; see recipe)
Reconstituted nucleosomes (dialyzed against NRB; UNIT 21.6)
Nucleosome remodeling factor (s)/chromatin-interacting protein(s) (see Methods Enzymol. 2004; 377)
Low-retention tubes (ISC Bioexpress)
BC 100 buffer (see recipe)
20 mM $MgCl_2$ (in NRB buffer)
20 mM ATP/30 mM $MgCl_2$ (in NRB)
200 mM ADP (in NRB buffer)
32 mM S-adenosylmethionine (SAM; New England Biolabs)
M.SssI (New England Biolabs)
4.5% PAA 0.5×TBE gel (optional step)
UV table (long wavelength; optional step)
TE buffer (see recipe)

M.SssI Treatment of In Vitro-Reconstituted Nucleosomes

The optimization of methylation of in vitro-reconstituted nucleosomes is performed using conditions analogous to the nucleosome remodeling reactions (see below).

1. Dilute approximately 500 ng of nucleosomes in 9 µL of NRB, in 4 low-retention tubes.

Nucleosomes are quantified here based on their DNA. Lower amounts of nucleosomes may also be used if the whole reaction is analyzed without an electrophoretic purification step (as long as about 50 ng of DNA are retrieved after the DNA precipitation step, see below). To avoid non-specific binding of proteins to the tubes, it is recommended to use low-retention tubes.

2. Add 9 µL of BC 100 buffer to each tube to match future reaction conditions after including nucleosome remodeling factor.

This will allow for the titration of up to 9 µL of studied enzyme. If your enzyme is in a different buffer, add 9 µL of that buffer. The final salt concentration should ideally be around 50 mM-75 mM of monovalent salt, as higher salt will affect the methylation reaction.

3. Add 2 µL of 20 mM $MgCl_2$ (in NRB buffer) to each tube.

4. Add 1.1 µL of 200 mM ADP to each tube.

This step is to mimic the remodeling reaction conditions. Omit it if you are planning on analyzing chromatin-binding proteins that are not ATP-dependent remodeling factors.

5. Add 4 µL of a mix containing 0.125 µL of SAM (160 µM final) and increasing amounts of M.SssI (e.g. add 0.125 µL (2.5 U) to one tube; 0.25 µL (5 U) to another tube; 0.5 µL (10 U) to the remaining tube) in NRB. A no-M.SssI control should be included consisting of just 4 µL of NRB in the tube.

Note that the density of CpG dinucleotides varies between DNA templates. For this reason, the optimal M.SssI concentration has to be determined empirically for each template.

6. Incubate at 37° C. for 15 min.

Samples may be optionally subjected to electrophoresis after step 6 and processed beginning step 16 in the section below.

7. Stop the reaction by adding an equal volume of phenol/chloroform to perform a DNA extraction followed by ethanol precipitation (UNIT 2.1A).

TE buffer and phenol/chloroform may be added to render the aqueous and organic phase volumes more amenable to manipulations. For example, the volume of the reaction can be adjusted to 100 µl with TE and 100 µl phenol/chloroform added accordingly to perform the DNA extraction.

8. Subject the DNA to bisulfite conversion (See Basic Protocol 3).

ATP-dependent remodeling of in vitro-reconstituted nucleosomes: DNA Methyltransferase-accessibility assay 9. Dilute about 500 ng of nucleosomes in 9 µL of NRB, in low-retention tubes.

Again, lower amounts of nucleosomes may be used if the whole reaction is analyzed without an electrophoretic purification step.

10. Add increasing amounts of remodeling factor (or chromatin binding protein) to the nucleosomes and adjust to 9 µL with BC 100 buffer or just add 9 µL of BC 100 buffer for the nucleosome input control.

Titrations may first be performed over a very broad range (e.g. between 50 ng and 2 µg of studied enzyme) and refined to obtain a titration producing little to complete change in nucleosome electrophoretic mobility. Note that the latter case does not necessarily mean that the end point of the reaction has been reached and it may just represent a steady state.

11. Add 2 µL of 10 mM ATP/30 mM $MgCl_2$ or just 2 µL of 20 mM $MgCl_2$ (in NRB buffer) for the minus ATP control.

Note that an additional 10 mM of $MgCl_2$ is added in the presence of ATP as it chelates $Mg^{2+}$. The minus ATP control may be carried out for only the highest concentration of remodeler once this concentration has been determined.

12. Incubate at 30° C. for 1 h.

13. Add 1.1 µL of 200 mM ADP to inhibit the reaction and incubate on ice for 10 min.

The appropriate ADP:ATP ratio to stop the remodeler has to be determined empirically for each remodeler.

14. Add 4 µL of M.SssI mix containing 0.125 µL of SAM and x µL (x U) M.SssI in NRB.

Use the optimal M.SssI concentration determined above in "M.SssI treatment of in vitro-reconstituted nucleosomes"

15. Incubate the reaction at 37° C. for 15 min.

Stop the reaction by adding phenol/chloroform and purify the DNA (UNIT 2.1A) if analysis of the whole reaction is to be performed. Otherwise proceed to step 8 to resolve nucleosome subpopulations.

16. Add about 2-3 µg (in about 1-3 µl) of competitor plasmid DNA (to compete the remodeler off of the nucleosomes) and incubate on ice for 10 min.

Use a plasmid or a large DNA fragment that will not enter the gel such that it will not interfere with the bands to be excised. Some chromatin-binding proteins may require adding more competitor DNA.

Sample Resolution

17. Load the samples onto a 4.5% PAA gel (UNIT 21.6, Support Protocol 6) and run at 9-10 V/cm for about 2.5 hours.

Use a gel with large wells (e.g., 11-13 mm) as the reactions contain a lot of DNA. The reactions also contain enough glycerol to be loaded directly onto the gel. Pre-run the gel for 1 h and rinse wells before loading samples.

Include a lane with loading dyes such as orange G and bromophenol blue in one well to monitor the migration. 100-bp DNA Ladder (NEB) may be included.

18. Disassemble the gel plates when the Orange G dye reaches the bottom of the gel and carefully transfer the gel into a box containing 100 mL of de-ionized water. Add 0.5 µg/mL ethidium bromide and incubate for 10 min.

The low percentage PAA gel can be more easily handled as a 'roll' by folding the sides of the gel twice towards the center.

19. Briefly rinse the gel in a beaker containing de-ionized water and lay the gel on top of a UV table covered with thin plastic wrap, and visualize the bands to be excised using the 365 nm (lower energy) wavelength lamp.

20. Excise the bands of interest with a scalpel and transfer the gel slices to individual tubes.

21. Add 400 µL of TE per tube to elute the nucleosomes from the gel overnight at 55° C.

22. Purify the DNA by phenol/chloroform extraction and ethanol precipitation (UNIT 2.1A).

23. Subject the DNA to bisulfite conversion (See Basic Protocol 3).

Basic Protocol 3. Bisulfite Conversion of Unmethylated Cytosine Residues to Thymidine Bisulfite Conversion can be done using different methods, two of which are described below. The conventional method is described first, while a more rapid method is detailed in the alternative protocol.

These following kits can be used in place of Basic Protocol 3. Most of the bisulfite conversion methods are interchangeable, however some genomic regions will only be converted using a particular method. It is unknown why some methods are better than others for some genomic regions, so if one particular method does not work, the others should be tried. The kits include: 1. Epitect Bisulfite Conversion from Qiagen; 2. EZ Methylation Kit from Zymo Reasearch; 3. methylSEQr bisulfite conversion kit from Applied Biosystems; 4. MethylCode Bisulfite Conversion Kit from Invitrogen Conventional Method
Materials
DNA (2-4 µg in nuclease free water)
Restriction enzymes
3M NaOH
3.6M Sodium Bisulfite Solution, pH 5.0 (Important, needs to be made fresh)
0.1M Hydroquinone (Sigma; Important, needs to be made fresh)
Wizard miniprep kit (Promega)
5M Sodium Acetate (NaOAc)
Ethanol
Glycogen 1. Digest 2-4 µg of DNA with restriction enzymes in a total volume of 20 µL.

Commonly used restrictions enzymes are HindIII, BamHI and EcoRI. Make sure to choose an enzyme which does not cleave the sequence you want to amplify by PCR.

2. Denature DNA at 90° C. for 20 min.

3. Add 5 µL of 3M NaOH to the denatured DNA and incubate at 45° C. for 20 min.

The 3M NaOH is made fresh. NaOH will react with the air over time resulting in the formation of $NaCO_3$, lowering the pH of the solution.

4. Make a 0.1M hydroquinone solution by adding 0.11 g of hydroquinone to water with a final volume of 10 mL.

5. Make a 3.6 M sodium bisulfite solution by adding 3.76 g of sodium bisulfite to 8.5 mL of water. Then pH solution with 3M NaOH to a final pH of 5.0 (note: it takes approximately 1 mL of 3M NaOH to make the pH 5.0). Bring the final volume to 10 mL with water.

6. To each sample add 12 µL of 0.1 M hydroquinone and 208 µl of 3.6 M Sodium Bisulfite, pH 5.0.

7. Incubate samples for 16 h at 55° C.

8. Separate DNA from the bisulfite solution using the Promega Wizard kit (Note: DNA is eluted from the columns using 50 µL of 80° C. de-ionized water.)

9. Desulfonate samples by adding 5 µL of 3M NaOH to the eluted DNA and incubate at 40° C. for 15 min.

DNA Purification

8. Precipitate DNA by adding 50 µL 5M NaOAc (sodium acetate), 300 µl ethanol and 1 µL glycogen to the desulfonated DNA and incubate the solution at −80° C. for 1 h or −20° C. overnight.

9. Spin samples in a microcentrifuge at 14,000×g for 20 min at 4° C.

10. Discard supernatant and wash the pellet once with 70% ethanol.

11. Allow pellet to dry and then resuspend the pellet in 40 µL of water.

Bisulfite converted DNA can now be stored at −20° C. for at least 1 year.

Alternate Protocol-Rapid Bisulfite Conversion

Basic protocol 2 works best if used with this bisulfite conversion method. Since protocol 2 uses a uniform population of DNA molecules they tend to easily anneal together after denaturation. This prevents efficient conversion. By performing the bisulfite conversion at 90° C. the DNA stays denatured during the reaction. This method was first described by Shiraishi M. et al (Shiraishi and Hayatsu, 2004).

Materials
Genomic DNA
Restriction enzymes
3M NaOH
$NaHSO_3$ (Wako)
$(NH_4)_2SO_3 \cdot H_2O$ (Wako)
50% $(NH_4)HSO_3$ (Wako)
10M sodium bisulfite solution (Important, needs to be made fresh)
Wizard miniprep kit (Promega)
Ethanol
Glycogen (20 mg/ml)
5M Sodium Acetate (NaOAc)

1. If being used with genomic DNA, digest 100 ng-2 mg of DNA with a restriction enzyme in a total volume of 20 µL. If starting with DNA from basic protocol 2 then dilute 10 ng-50 ng of DNA in a final volume of 20 µL.

Commonly used restrictions enzymes are HindIII, BamHI and EcoRI. Make sure to choose an enzyme which does not cleave the sequence you want to amplify by PCR.

2. Denature DNA at 90° C. for 20 min.

3. Add 5 µL of 3M NaOH to the denatured DNA and incubate at 45° C. for 20 min. (The NaOH will help to further denature the DNA).

The 3M NaOH is made fresh. NaOH will react with the air over time resulting in the formation of $NaCO_3$, lowering the pH of the solution.

4. Meanwhile mix 2.08 g $NaHSO_3$, 0.67 g $(NH_4)_2SO_3 \cdot H_2O$ and 5.0 mL of 50% $(NH_4)HSO_3$. Then heat mixture at 90° C. to obtain a solution of pH 5.2-5.3 (This is the pH of the solution when it has cooled down to room temperature. However, the solution should be added to sample when it is at 90° C.).

This solution should be made fresh.

5. Add 282 µL of the 10 M bisulfite solution (from step 4) to the alkali-denatured DNA. Incubate the mixture at 90° C. for 10 min.

6. Separate DNA from the bisulfate solution using the Promega Wizard kit (Note: DNA is eluted from the columns using 50 µL of 80° C. de-ionized water.)

7. Desulfonate samples by adding 5 µL of 3M NaOH to the eluted DNA and incubate at 40° C. for 15 min.

DNA Purification

8. Add 50 µL 5M NaOAc (sodium acetate), 300 µL ethanol and 1 µL glycogen to the desulfonated DNA and incubate the solution at −80° C. for 1 h or −20° C. overnight.

9. Spin samples in a microcentrifuge at 14,000×g for 20 min at 4° C.

10. Discard supernatant and wash the pellet once with 70% ethanol.

11. Allow pellet to dry and then resuspend the pellet in 40 µL of water.

Bisulfite converted DNA can now be stored at −20° C. for at least 1 year.

Basic Protocol 4. PCR and Cloning to Obtain Single Molecule Resolution of Promoter Architecture PCR reactions are performed using bisulfite-specific primers. These specific primers are designed so that they contain converted C's within their sequence. These primers must not contain CpG sites in their sequence as these sites will variably convert depending on their methylation state.

Figure 5:
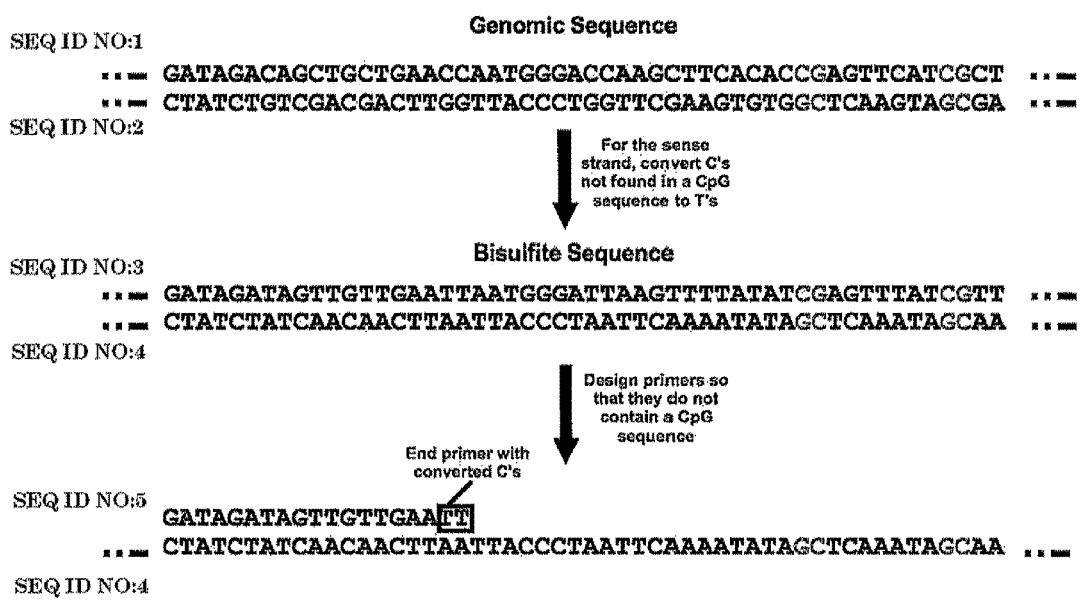
FIG. 5 shows the primer design for amplification of bisulfite converted DNA. First take the genomic sequence and convert all C's that are not part of a CpG site to T's. Then design a forward primer that is complementary to the antisense strand. This primer should not contain any CpG's in it and should end in a converted C (if possible). The primer should be 18-30-bp and have a melting temperature above 50° C. Do the same for the reverse primer, but have it complement the sense strand. CpG sites are marked in red and primer is marked in blue.

1. Design primers that are specific to bisulfite-converted DNA (See FIG. 5) and encompass the region of interest.

The sequence for the forward primer should have all C's replaced by T's (if made from the sense stand) and the reverse primer should have all the G's replaced by A's (if made from the antisense strand). Neither primer sequence should contain CpG sites. Primer set is more specific if one of the primers ends in at least one converted C. Amplicons longer than 1 kb are inefficiently amplified by PCR, likely due to breakage that occurs during the bisulfite conversion. Optimal amplicons are approximately 600-bp.

2. 1-2 µL of bisulfite converted DNA is usually used per PCR reaction and each PCR is performed for 40 cycles when starting with protocol 1 or 20 cycles when using basic protocol 2 (UNIT 15.1)

A Taq polymerase which adds 3'-A overhangs to the PCR product should be used. This is necessary for cloning in the TOPO TA vector (see step 3). In addition, PCR conditions will need to be optimized for each primer set. For amplicons up to 700-bp, a 1 min extension time is usually sufficient.

3. PCR products are then cloned using Invitrogen's TOPO TA cloning kit following manufacturer's instructions.

It is recommended that cloning is done immediately following PCR amplification. Storage of PCR products prior to cloning results in the loss of the A overhangs thereby decreasing cloning efficiency.

4. Plasmid DNA can be amplified and/or purified by either minipreps or templiphi (GE Healthcare) following the manufacturer's instructions.

5. Sequence individual clones.

Analysis of Sequences

Many programs can be used to analyze sequences from bisulfite converted DNA. Two are listed below.

1. BiQ Analyzer (Bock et al., 2005
2. CpG PatternFinder (Xu et al., 2007)
    http://www.biotechniques.com/BiotechniquesJournal/2007/September/C pG-PatternFinder-a-Windows-based-utility-program-for-easy-and-rapid-identification-of-the-CpG-methylation-status-of-DNA/biotechniques-43114.html Reagents and Solutions Use deionized, distilled water in all recipes and protocol steps 10× Stock RSB Buffer
100 mM Tris-HCl, pH 7.4
100 mM NaCl,
30 mM $MgCl_2$
can be stored for at least 1 year at 4° C.
1×SssI Buffer
10 mM Tris-HCl, pH 7.9
50 mM NaCl
10 mM $MgCl_2$
1 mM dithiothreitol
0.3 M sucrose
can be stored for at least 1 year at 4° C.
(Can also be made from NEB Buffer 2 (10×) plus sucrose)
Stop Solution (2× Lysis Buffer)
20 mM Tris-HCl, pH 7.9
600 mM NaCl
1% SDS
10 mM EDTA
(must be pre-warmed at 37° C. prior to use for SDS to go into solution)
can be stored at least 1 year at room temperature
Nucleosome Remodeling Buffer (NRB)
10 mM HEPES, pH 7.9
50 mM NaCl
3 mM $MgCl_2$
3% Glycerol
1 mM Dithiothreitol
Filtered with Steriflip (Millipore) can be stored for at least 1 year at 4° C.
In Vitro-Reconstituted Nucleosomes (See UNIT 21.6).
dialyzed against NRB
Nucleosome Remodeling Enzyme (See Methods Enzymol. 2004; 377).
in BC 100 buffer
BC buffer
10% Glycerol
20 mM HEPES, pH 7.9
0.4 mM EDTA
(BC 100 is supplemented with 100 mM NaCl)
can be stored for at least 1 year at 4° C.
TE (TRIS-EDTA)
10 mM TRIS pH 8.0
1 mM EDTA
can be stored indefinitely 1 year at room temperature Critical Parameters and Troubleshooting:

a. Nuclei Purification

Some nuclei are more fragile than others and may lyse especially during the high salt treatment (this can be checked by looking at a small aliquot under the microscope). However, lysis may be overcome by incubating the nuclei in the high salt buffer for a couple of minutes and then diluting the sample 10-20 fold with RSB buffer before centrifuging. Nuclei can also be spun at a lower speed for a longer (amount of time). In addition nuclei can be resuspended in RSB buffer containing 200 mM NaCl and then an equal volume of RSB buffer containing 600 mM NaCl can be carefully added.

b. M.SssI Treatment

If the M.SssI concentration used is too low, methylation will be sporadic and protections larger than 170-bp will be observed while high concentrations of M.SssI will cause methylation within the nucleosome-protected DNA (mainly at the entry/exit points of the nucleosomes). Although both varying M.SssI concentration and time of incubation may be used to obtain ideal nucleosome footprints, using a higher M.SssI concentration for a relatively short time (i.e. 15-20 min) appears to be better than using little enzyme for longer time. Be aware of incubating too long with M.SssI as chromatin structure may change over time.

c. DNA Templates for In Vitro Remodeling Assay

It is recommended to use DNA sequences containing a high density of CpG dinucleotides in order to obtain a high-resolution DNA accessibility mapping. Since working with a homogeneous starting substrate facilitates subsequent data analysis, it is also recommended to use DNA templates containing nucleosome-positioning sequences (see commentary UNIT 21.6)

d. Conditions for Nucleosome Remodeling or Binding

Remodeling reactions need to be optimized. Partial remodeling may result from both using insufficient amounts as well as a vast excess of remodeler. Hence, the amount of protein that will produce a maximal change in nucleosome electrophoretic mobility has to be determined empirically. It will depend on many parameters such as the specific activity of the tested protein (complex), the quality of the protein preparation and the assay conditions (e.g. salt concentration, time and temperature of incubation). The assay conditions may be changed, however this may impact on methylation efficiency as the NRB was designed to be similar to the 1×M.SssI buffer (NEB 2). Therefore optimization of the methylation reaction would have to be repeated with the new remodeling (or binding) conditions. Note that in this assay the $MgCl_2$ concentration was reduced compared to 1×NEB 2 buffer to avoid nucleosome precipitation. Lastly, if you intend to analyze DNA circles or plasmids assembled onto nucleosomes, it is noteworthy that M.SssI has been reported to exhibit topoisomerase activity at $MgCl_2$ concentrations above 3 mM (Renbaum et al., 1990).

e. Primer Design

In addition to conventional rules that apply to designing PCR primers (see UNIT 15.1), it is important to make sure that primers are designed to the converted sequence and do not contain CpG sites within them. Make sure that at least one primer ends in a converted C. This will make the primer more specific for the converted DNA. Primers should be tested on unconverted DNA in order to make sure there is no amplification.

f. PCR Amplification (see UNIT 15.1)

Even when careful consideration is taken to properly design primers; PCR amplification might fail. It is important that every PCR is optimized for annealing temperature. In addition, magnesium concentrations can be varied and/or DMSO can be added to the reaction. Different Taq Polymerases can also be tried. If all else fails, design new primers. Some primer pairs just don't work well.

g. TA Cloning

Sometimes many false positives may be obtained after TA cloning. This can be due to primer dimers or other non-specific PCR products formed during PCR amplification. If this is the case, the PCR product can be gel-purified before cloning. (UNIT 2.6 or Qiagen Gel Extraction kit).

h. DNA Sequencing Reveals Unconverted Sequences

Poorly converted amplicons will automatically be determined by BiQ analyzer program. Proper conversion is defined by having at least 90% of the Cs found in the amplicon which are not part of CpG sites converted to Ts. If unconverted or partially converted DNA sequences are retrieved then try a different bisulfite conversion method, as some methods are not efficient at converting certain sequences. Alternatively, primers may need to be redesigned.

i. DNA Sequences Appear to all have the Same Methylation Pattern

Caution should be taken to make sure that the results are not due to the PCR amplification or sequencing of only a few strands of DNA. If bisulfite-converted DNA is of poor quality or if low amounts of DNA are being used as a template, then the PCR amplification will result in amplification of only a few strands. This may be reflected by a weak PCR product. In this case, the sequences obtained may all have the same methylation pattern. The BiQ Analyzer allows for determining potential duplicate sequences.

Anticipated Results

Figure 6:
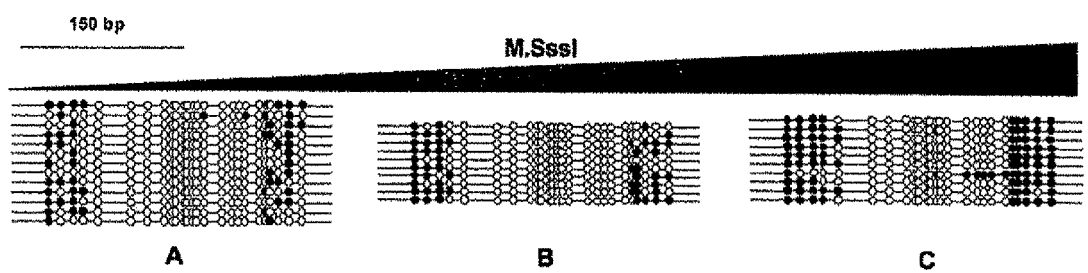
FIG. 6 shows the methylation of mononucleosomes with increasing amounts of M.SssI. Open circles represent CpG sites that were inaccessible to M.SssI and closed circles indicate CpG sites that were methylated by M.SssI. If too little M.SssI is used or if incubation times are too short intermittent methylation patterns will be seen, as well as protection patterns which are >150-bp per nucleosome (Panels A and B). If experiment works correctly then a nice protection pattern of 150-bp per nucleosome will be observed as patches of open CpG sites (Panel C).

If using purified nuclei as a starting material, the number of positive colonies obtained after TA cloning will vary relative to PCR amplification efficiency (before cloning). This will vary from sequence to sequence. After analysis of the sequencing data, protection patterns of about 150-bp per nucleosome should be observed (FIG. 6). If intermittent patterns are observed then experiment did not work correctly and may need to be re-optimized for amount of M.SssI used and incubation time. Smaller protection patterns may be observed for tightly bound transcription factors.

For the M.SssI treatment of in vitro-reconstituted nucleosomes 20-100 ng of DNA should be recovered from the gel slices (as measured by NanoDrop). After the TA cloning 50-100 positive colonies should be obtained. After sequencing, about 90% of the DNA molecules should show a nucleosomal protection between 146 and 170-bp (FIG. 6).

Time Consideration

If starting with basic protocol 1, the whole procedure up to the sequencing of clones should take 4 days. On day 1 nuclei isolation and M.SssI treatment should be completed with the proteinase K digestion allowed to proceed overnight. On the second day the DNA can be purified and the bisulfite conversion completed (if the conventional bisulfite conversion method is used then this reaction can be allowed to proceed overnight). PCR amplification and TA cloning can be completed on day 3 with the transformed colonies being allowed to grow overnight on LB plates containing the correct selective antibiotic. On the fourth day colonies can be screened and submitted for sequencing.

If starting with protocol 2, the whole procedure should take about 5 days (not including sequencing time). Since polymerization of the 4.5% PAA gel takes about 1 h, it is better to pour the gel early during the day or the day before doing the experiment (and keep the gel damp at 4° C.). Since the pre-run of the gel takes about 1 h, it can be started before setting, up the remodeling reactions. Depending on the number of samples and the number of bands to be excised, the whole remodeling procedure may take about 5 h to 6 h. Together with the overnight nucleosome gel-elution and the DNA extraction and precipitation, count 2 days of work before subjecting the DNAs to the bisulfite conversion, PCR and cloning.

REFERENCES CITED IN PART II

The following references are incorporated herein in their entirety:

Appanah, R., Dickerson, D. R., Goyal, P., Groudine, M. and Lorincz, M. C. 2007. An unmethylated 3' promoter-proximal region is required for efficient transcription initiation. *PLoS Genet.* 3: e27.

Bock, C., Reither, S., Mikeska, T., Paulsen, M., Walter, J. and Lengauer, T. 2005. BiQ Analyzer: visualization and quality control for DNA methylation data from bisulfate sequencing. *Bioinformatics* 21: 4067-8.

Boeger, H., Griesenbeck, J., Strattan, J. S. and Kornberg, R. D. 2003. Nucleosomes unfold completely at a transcriptionally active promoter. *Mol Cell* 11: 1587-98.

Boeger, H., Griesenbeck, J., Strattan, J. S. and Kornberg, R. D. 2004. Removal of promoter nucleosomes by disassembly rather than sliding in vivo. *Mol Cell* 14: 667-73.

Bouazoune, K., Miranda, T. B., Jones, P. A., and Kingston, R. E. 2009. Analysis of individual remodeled nucleosomes reveals decreased histone-DNA contacts created by hSWI/SNF. *Nucleic Acids Res (in press)*

Fatemi, M., Pao, M. M., Jeong, S., Gal-Yam, E. N., Egger, G., Weisenberger, D. J. and Jones, P. A. 2005. Footprinting of mammalian promoters: use of a CpG DNA methyltransferase revealing nucleosome positions at a single molecule level. *Nucleic Acids Res* 33: e176.

Gal-Yam, E. N., Jeong, S., Tanay, A., Egger, G., Lee, A. S. and Jones, P. A. 2006. Constitutive nucleosome depletion and ordered factor assembly at the GRP78 promoter revealed by single molecule footprinting. *PLoS Genet.* 2: e160.

Gonzalgo, M. L. and Jones, P. A. 1997. Rapid quantitation of methylation differences at specific sites using methylation-sensitive single nucleotide primer extension (Ms-SNuPE). *Nucleic Acids Res* 25: 2529-31.

Gonzalgo, M. L. and Liang, G. 2007. Methylation-sensitive single-nucleotide primer extension (Ms-SNuPE) for quantitative measurement of DNA methylation. *Nat Protoc* 2: 1931-6.

Hamiche A., Sandaltzopoulos R., Gdula D. A., Wu C. 1999. ATP-dependent histone octamer sliding mediated by the chromatin remodeling complex NURF. *Cell* 97:833-42.

Hinshelwood R. A., Melki J. R., Huschtscha L. I., Paul C., Song J. Z., Stirzaker C., Reddel R. R., Clark S. J. 2009. *Aberrant de novo methylation of the p16INK4A CpG island is initiated post gene silencing in association with chromatin remodeling and mimics nucleosome positioning. Hum Mol Genet* in press.

Kladde, M. P. and Simpson, R. T. 1994. Positioned nucleosomes inhibit Dam methylation in vivo. *Proc Natl Acad Sci USA* 91: 1361-5.

Kladde, M. P. and Simpson, R. T. 1996. Chromatin structure mapping in vivo using methyltransferases. *Methods Enzymol* 274: 214-33.

Kladde, M. P., Xu, M. and Simpson, R. T. 1996. Direct study of DNA-protein interactions in repressed and active chromatin in living cells. *Embo J* 15: 6290-300.

Längst G, Bonte E J, Corona D F, Becker P B. 1999. Nucleosome movement by CHRAC and ISWI without disruption or trans-displacement of the histone octamer. *Cell* 97:843-52.

Lin, J. C., Jeong, S., Liang, G., Takai, D., Fatemi, M., Tsai, Y. C., Egger, G., Gal-Yam, E. N. and Jones, P. A. 2007. Role of nucleosomal occupancy in the epigenetic silencing of the MLH1 CpG island. *Cancer Cell* 12: 432-44.

Lomvardas, S. and Thanos, D. 2001. Nucleosome sliding via TBP DNA binding in vivo, *Cell* 106: 685-696.

Lorch, Y., LaPointe, J. W. and Kornberg, R. D. 1987. Nucleosomes inhibit the initiation of transcription but allow chain elongation with the displacement of histones. *Cell* 49: 203-10.

Lusser, A. and Kadonaga, J. T. 2003. Chromatin remodeling by ATP-dependent molecular machines. *Bioessays* 25: 1192-200.

Rando, O. J. and Chang, H. Y. 2009. Genome-Wide Views of Chromatin Structure. *Annu Rev Biochem.* 78:245-71

Renbaum P, Abrahamove D, Fainsod A, Wilson G G, Rottem S, Razin A. 1990. Cloning, characterization, and expression in *Escherichia coli* of the gene coding for the CpG DNA methylase from *Spiroplasma* sp. strain MQ1 (M.SssI). *Nucleic Acids Res.* 18:1145-52.

Shiraishi, M. and Hayatsu, H. 2004. High-speed conversion of cytosine to uracil in bisulfite genomic sequencing analysis of DNA methylation. *DNA Res* 11: 409-15.

Studitsky, V. M., Clark, D. J. and Felsenfeld, G. 1995. Overcoming a nucleosomal barrier to transcription. *Cell* 83: 19-27.

Studitsky, V. M., Walter, W., Kireeva, M., Kashlev, M. and Felsenfeld, G. 2004. Chromatin remodeling by RNA polymerases. *Trends Biochem Sci* 29: 127-35.

Tost, J., Dunker, J. and Gut, I. G. 2003. Analysis and quantification of multiple methylation variable positions in CpG islands by Pyrosequencing. *Biotechniques* 35: 152-6.

Tsukiyama, T., Becker, P. B. and Wu, C. 1994. ATP-dependent nucleosome disruption at a heat-shock promoter mediated by binding of GAGA transcription factor. *Nature* 367: 525-32.

Wang, R. Y., Gehrke, C. W. and Ehrlich, M. 1980. Comparison of bisulfite modification of 5-methyldeoxycytidine and deoxycytidine residues. *Nucleic Acids Res* 8: 4777-90.

Workman, J. L. and Kingston, R. E. 1998. Alteration of nucleosome structure as a mechanism of transcriptional regulation. *Annu Rev Biochem* 67: 545-79.

Xu, Y. H., Manoharan, H. T. and Pitot, H. C. 2007. CpG PatternFinder: a Windows-based utility program for easy and rapid identification of the CpG methylation status of DNA. *Biotechniques* 43: 334, 336-40, 342. Methods in ENZYMOLOGY, 2004, Volume 377; Chromatin and Chromatin Remodeling Enzymes, Part C Example III Hypomethylation of a Line-1 Promoter Activates an Alternate Transcript of the MET Oncogene in Bladders with Cancer Introductory Remarks Aberrant DNA methylation is involved in the initiation and progression of carcinogenesis and includes both hypermethylation of CpG islands at gene promoters and global hypomethylation. While a small portion of hypomethylation occurs at gene promoters, resulting in overexpression of certain oncogenes [1,2], the majority occurs at repetitive elements, such as long interspersed nuclear elements (LINE-1s or L1s) [3]. Since most of the 500,000 copies of L1 have become nonfunctional over the course of human evolution [4] and can no longer transpose, genome-wide hypomethylation at L1s during tumorigenesis is thought to contribute mainly to chromosomal instability [5]. In mice hypomethylation of transposable elements can lead to disruption of normal gene function [6]. Viable yellow agouti ($A^{vy}$) mice have a retrotransposon inserted into one allele of the agouti locus and when this retrotransposon is hypomethylated, which can occur in utero by limiting the maternal intake of methyl donors, it acts as an alternate promoter for agouti. Ectopic induction of the agouti gene results in altered coat color, obesity, and an increased incidence of tumors [6]. While it is well known that repetitive elements are hypomethylated in cancer, it has never been directly demonstrated that hypomethylation of a retrotransposon leads to ectopic gene expression in humans.

A recent study has revealed that more than 30% of transcription start sites in the human genome are located within repetitive elements, with just over 7% in L1s [7]. A full length L1 sequence (6 Kb) has a sense promoter driving transcription of its two open reading frames and an antisense promoter driving transcription in the opposite direction that can act as an alternate promoter for surrounding genes [8-10]. Almost 500 of these retrotransposons can induce ectopic gene expression in embryonic and cancerous tissues, revealing their potential role during both development and tumorigenesis [7]. However this study did not address the potential mechanism of how repetitive elements become transcriptionally active. Since the L1 promoter is a CpG island and methylated in normal somatic tissues it seems likely that epigenetic mechanisms are involved in its transcriptional silencing. There are many layers of epigenetic regulation responsible for regulating expression of single copy genes, including DNA methylation, histone modifications, and nucleosome occupancy [11]. While it is known that unmethylated retrotransposons in *Arabidopsis* [12] acquire the active histone variant H2A.Z, the chromatin structure in humans of repetitive elements, particularly active ones, has been largely ignored.

Until recently it has not been possible to study the promoters of individual. Ms since the sequences are too similar to design primers for one particular locus [13-15]. Therefore a direct correlation between the epigenetic status of a specific L1 and expression of its associated transcript has not been possible. For the first time to our knowledge, we have elucidated the role of epigenetics in the transcriptional activity of L1s by utilizing novel assays capable of examining the methylation status and chromatin structure of specific Ms and expression of alternate transcripts originating from the L1 promoters. In addition to L1s being hypomethylated and transcriptionally active in bladder tumors we also found that a specific L1 located within the MET oncogene is active across entire bladders with cancer. The clinical implication of our finding is that surgical excision of the tumor would leave behind large areas of the bladder that remain epigenetically altered and express a potential oncogene. We also provide evidence that an active acquires H2A.Z and nucleosome free regions upstream of TSSs, which has only been described previously at single copy genes, and undergoes chromatin remodeling from an inactive tetranucleosomal structure to an active dinucleosomal structure.

Discussion of Certain Results

Figure 13:
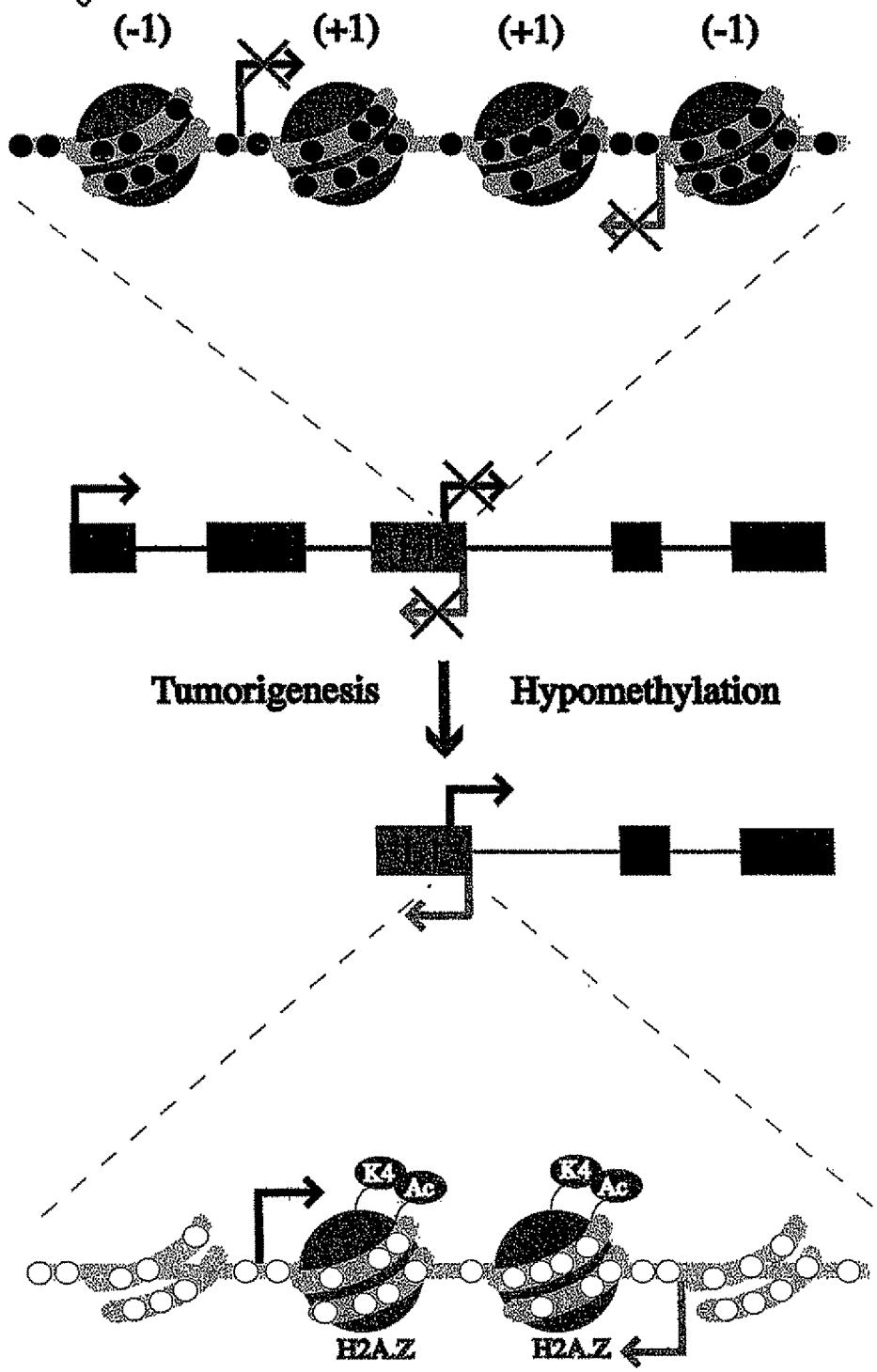
FIG. 13 is a model of the epigenetic alterations that occur between inactive L1s and active Ms during tumorigenesis. An L1 promoter is usually silenced by DNA methylation and has a compact chromatin structure with four nucleosomes occupying the promoter. Upon hypomethylation during tumorigenesis the L1 promoter becomes transcriptionally active. The active promoter loses a nucleosome upstream of each of the transcription start sites, resulting in a dinucleosome structure. The remaining nucleosomes have acetylated H3, H3K4me3, and H2A.Z. (−1) represents the nucleosome directly upstream of the transcription start site, while (+1) represents directly downstream nucleosome of transcriptional start site.

The consequences of global hypomethylation at repetitive elements in cancer has long been the subject of speculation regarding the generation of genomic instability and potential activation of oncogenes. While hypomethylation during tumorigenesis occurs quite frequently, a direct demonstration of the impact of hypomethylation of repetitive elements on gene expression has not been conducted. Using several specific L1s we have demonstrated the mechanism of transcriptional activation and, taken together with the results of Faulkner et al. [7], our results highlight the previously underappreciated impact of hypomethylation on ectopic gene expression, possibly contributing to tumorigenesis in a synergistic or cooperative manner (see model in FIG. 13).

To elucidate the mechanism of transcriptional activation of repetitive elements, we compare the epigenetic alterations, including methylation status, histone modifications, and nucleosome positioning, that occur at a single copy of an L1 between a transcriptionally inactive and active state. Since current methods did not exist for such a study we employ several novel assays, including using primers able to amplify specific L1s, enabling methylation and ChIP assays to be performed on single copies, and a modification of the method for determining nucleosome positioning at a single molecule resolution, which allowed for the determination of nucleosome positioning in a methylated region. We were able to show that transcription from the L1 promoter is silenced by DNA methylation, providing direct evidence that one function of DNA methylation is to protect the human genome from retrotransposons.

Transcriptional activation of L1 promoters by hypomethylation results in a chromatin structure similar to that of active single copy genes such as p16, revealing that the features of active promoters, such as acquisition of active histone marks, H2A.Z, and nucleosome free regions upstream of TSSs, are not restricted to canonical gene promoters. In addition, we found that the unique structure of the L1 promoter results in two very stable nucleosome occupancy states, the inactive tetranucleosome structure and the active dinucleosome structure, and that hypomethylation could result in a switch between the two. It has been demonstrated that tetranucleosomes form a compact chromatin fiber [37]. Therefore, the widespread chromatin remodeling due to global hypomethylation of L1 promoters could contribute to chromosomal instability through the loss of many stabilizing tetranucleosome structures.

Figure 22:
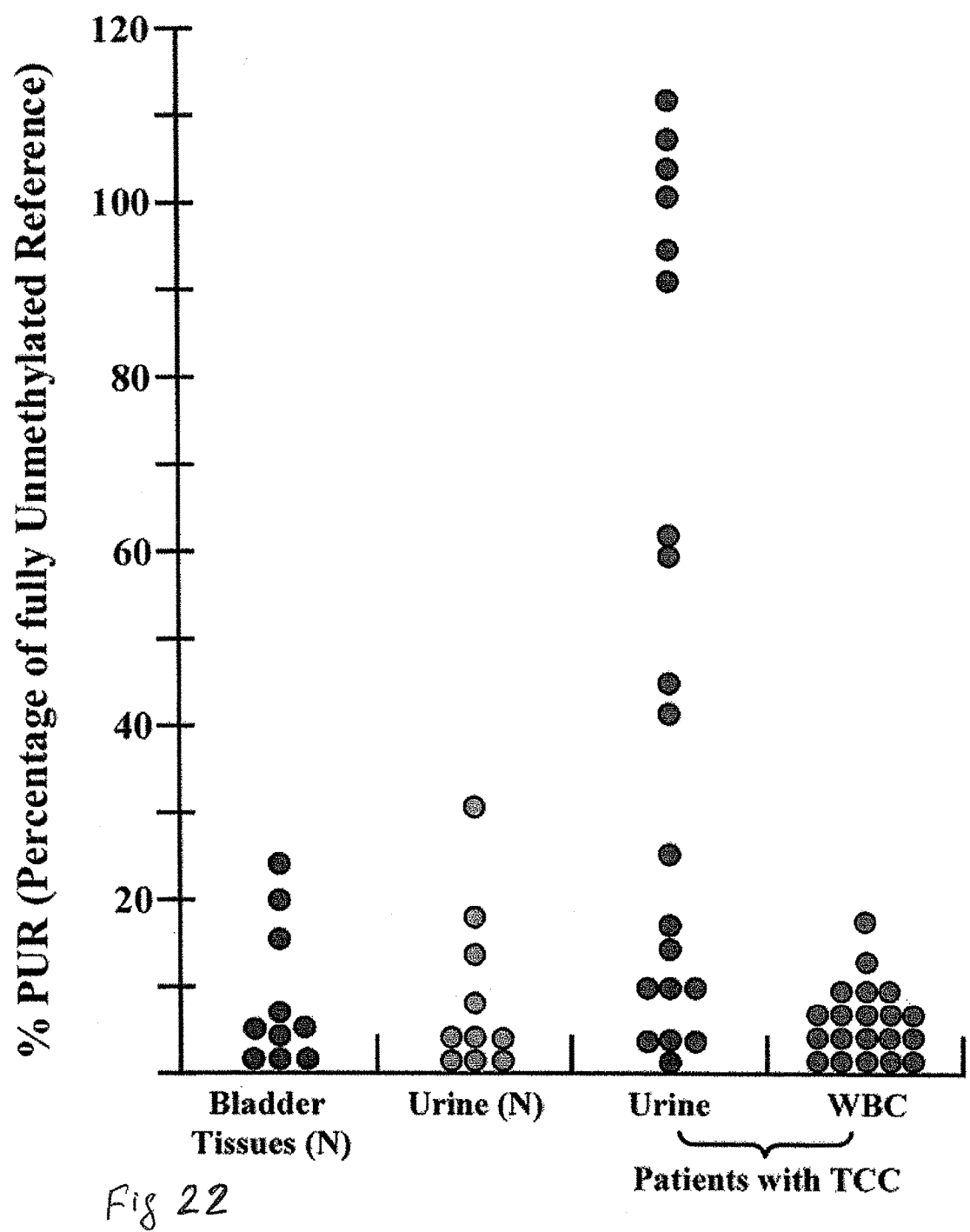
FIG. 22 shows the detection of L1-MET hypomethylation in urine sediments of patients with bladder cancer. Bisulfite-specific primers and a probe were designed for the MethyLight assay that amplified only completely unmethylated strands of L1-MET. Bladder tissues (N) from age-matched patients without bladder cancer (n=10) and urine (N) from age-matched healthy volunteers (n=10) showed low levels of L1-MET hypomethylation. However, urine (n=20) from patients with TCC showed high levels of L1-METhypomethylation, which was specific to the bladder since it was not detected in their white blood cells (WBC) (n=20). Unmethylated levels (Y axis) indicate the Percent of fully Unmethylated Reference (PUR) values. Found at: doi:10.1371/journal.pgen.1000917.s009 (0.30 MB TIF)

To our knowledge we have provided the first direct evidence that transcriptional activation of repetitive elements is caused by hypomethylation and chromatin remodeling at their promoters, occurs in a human diseased state, and may play a role in disease predisposition. Specifically, hypomethylation of a L1 promoter induces an alternate transcript of the MET oncogene in bladder tumors and across the entire urothelium of tumor-bearing bladders. The presence of L1-MET hypomethylation across the entire urothelium of tumor-bearing bladders has several possible explanations. Epigenetic alterations such as hypermethylation of tumor suppressor genes and hypomethylation of L1s have been found in normal epithelia adjacent to several types of tumors, including breast [38], esophageal [39], and colon [40,41], indicating the presence of a "field defect". Our data supports the presence of an epigenetic field defect in bladders with cancer, either due to independent events across the urothelium or clonal expansion [42]. However, another possible explanation is that the loss of L1-MET methylation occurred during early development before the bladder was fully formed. While some evidence for such abnormal epigenetic programming exists, as a recent study revealed that people who develop bladder cancer have slightly lower levels of global DNA methylation in their blood than healthy control cases [43], we did not find any evidence of a loss of methylation at global L1s or specific L1s in our patient WBC samples (FIG. 22). Another possibility, which cannot be ruled out by this data, is that the presence of a tumor causes epigenetic changes across the bladder.

Whatever the underlying mechanism, the modulation of gene expression by hypomethylation of a retrotransposon such as what occurs at the agouti locus in mice is also found in humans. This leads to the activation of surrounding genes, which may contribute to tumorigenesis in a synergistic or cooperative manner. Transurethral resection of bladder tumors would leave behind large areas of epigenetically altered urothelium, possibly contributing to the high level of recurrence of bladder cancer. Fortunately, hypomethylation at specific L1s seems to provide a valuable biomarker that has the potential to significantly impact the diagnosis and treatment of bladder cancer.

Figure 14:
FIG. 14 shows the specific L1s with alternate transcripts located in intron of genes. Black boxes represent exons of the host gene while red boxes represent a specific L1. The black arrow represents the transcriptional start site of the host gene while the red arrow represents the alternate transcriptional start site within the potentially active L1 promoter. GenBank accession numbers for representative alternate transcripts are followed by the number in parentheses of similar transcripts transcribed from the individual L1. All L1s are antisense to their host genes, yielding alternate transcripts that are sense with their host genes. Found at: doi: 10.1371/journal.pgen. 1000917.s001 (0.56 MB TIF)
Figure 15A:
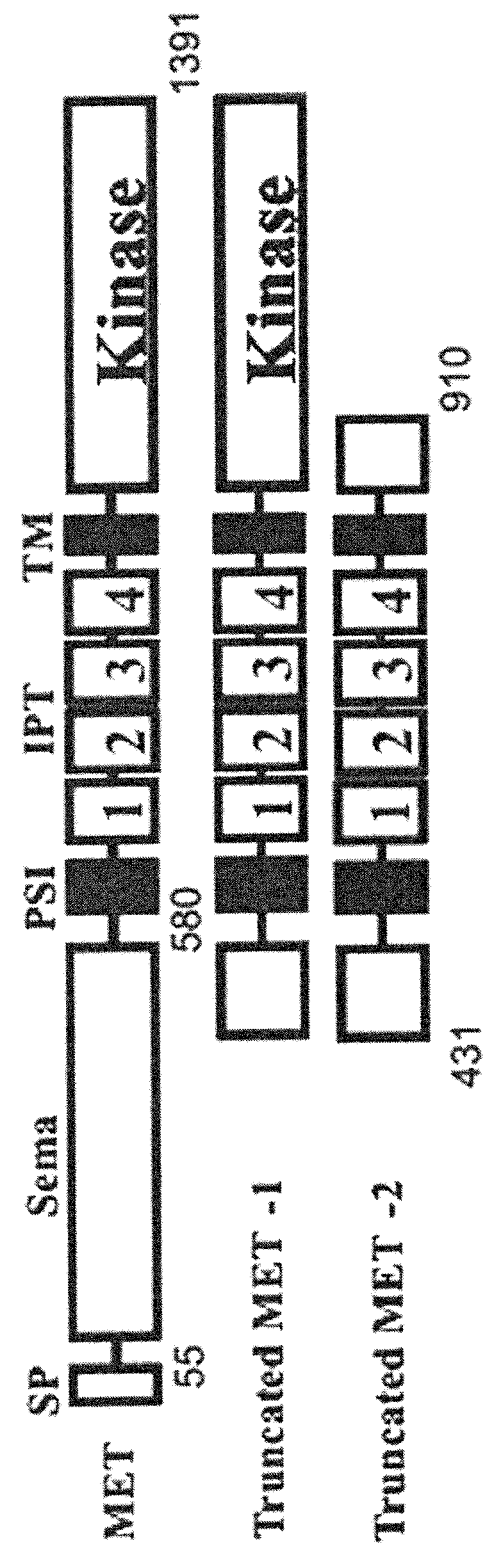
FIG. 15 shows the truncated MET protein encoded by L1-MET. (A) The functional domains of MET include the signal peptide (SP), sema domain at the N-terminus, the PSI domain, IPT repeats, the transmembrane domain (TM), and the kinase domain at the C-terminus. The structure of truncated MET proteins 1 and 2 are shown, encoded by transcripts derived from placenta (GenBank accession no. BX334980) and a bladder carcinoma cell line (BF208095), respectively. (B) The two E1-MET transcripts, truncated L1-MET-1 (T-MET-1) and truncated L1-MET-2 (T-MET-2), were cloned into a pMEV expression vector with 2 HA tags fused at the N-terminal. Hela cells were transfected with either the empty pMEV vector, pMEV T-MET-1, or pMEV T-MET-2 and protein was extracted after 48 hours. The expression of truncated MET-1 (90 kDa) and truncated MET-2 (60 kDa) was detected by western blot using an HA antibody. (C) Results of 5'RACE reveal the start site for L1-MET within the L1 element. The transcriptional start site of L1-MET was confirmed by 5'RACE in the T24 cell line which expressed L1-MET. The underlined sequence is located inside of the LINE-1. (D) RT-PCR analysis of reactivation of L1-MET by 1 or 3 μM of 5-Aza-CdR treatment for 24 hours (day 3 after treatment). β-actin expression level was used as a control. Found at: doi: 10.1371/journal.pgen. 1000917.s002 (1.22 MB TIF)
Figure 15B:
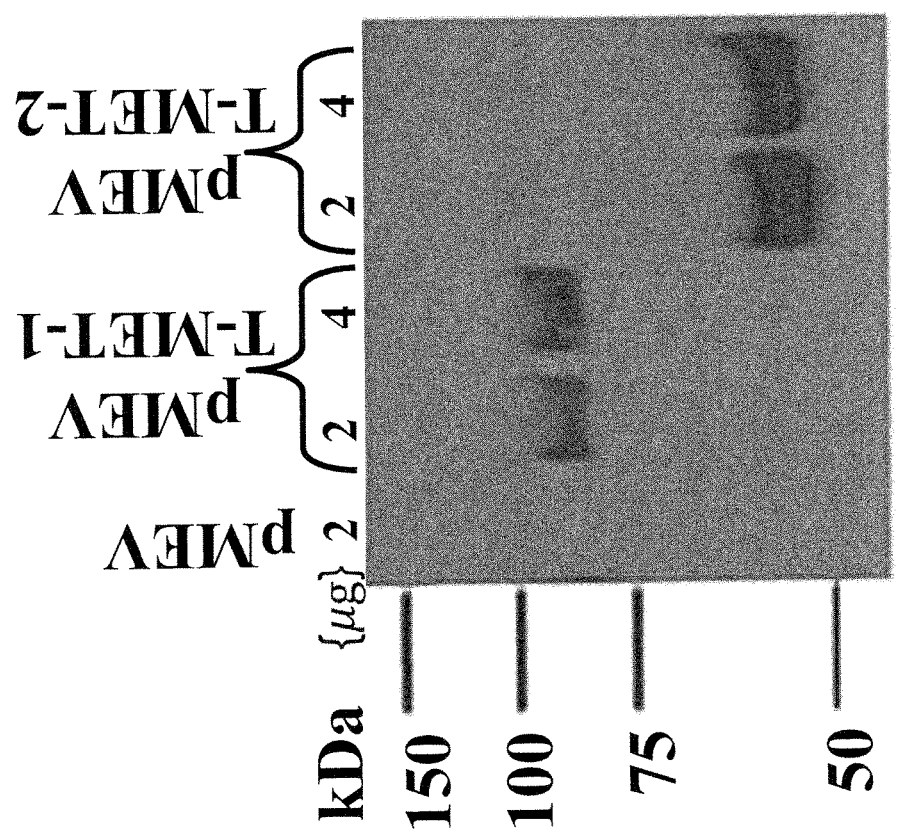

Results Include:

Hypomethylation of specific L1s correlates with expression of alternate gene transcripts. To elucidate the mechanism of transcriptional activation of repetitive elements we used the sequence of the functional promoter of L1s to identify specific promoters potentially capable of expressing alternate transcripts of host genes. FIG. 14 contains the genomic locations of the L1s, all of which are in an antisense orientation to the host gene allowing for transcripts in sense orientation to the gene's coding sequence. Interestingly, most these ESTs are from tumor cells. One such L1 is located within the MET oncogene (L1-MET) [8]. Since MET is known to be overexpressed in bladder cancer [16-18], we characterized two L1-MET transcripts by sequencing EST clones obtained from a bladder carcinoma cell line (GenBank accession no. BF208095) and placenta (BX334980). Both transcripts have start sites located in the L1 promoter, share the same reading frame as MET (FIG. 15A), and when transiently transfected into Hela cells result in expression of truncated MET proteins (FIG. 15B). Several truncated forms of the tyrosine kinase MET, which is the hepatocyte growth factor (HGF) receptor, are constitutively active and promote invasion and migration through activation of a variety of signal transduction pathways in numerous types of carcinomas, including breast, prostate, colorectal, and lung, in musculoskeletal sarcomas, and also in haematopoietic malignancies [19,20]. Therefore hypomethylation of L1-MET could lead to expression of a transcript that encodes a truncated and potentially constitutively active MET protein.

Figure 7A:
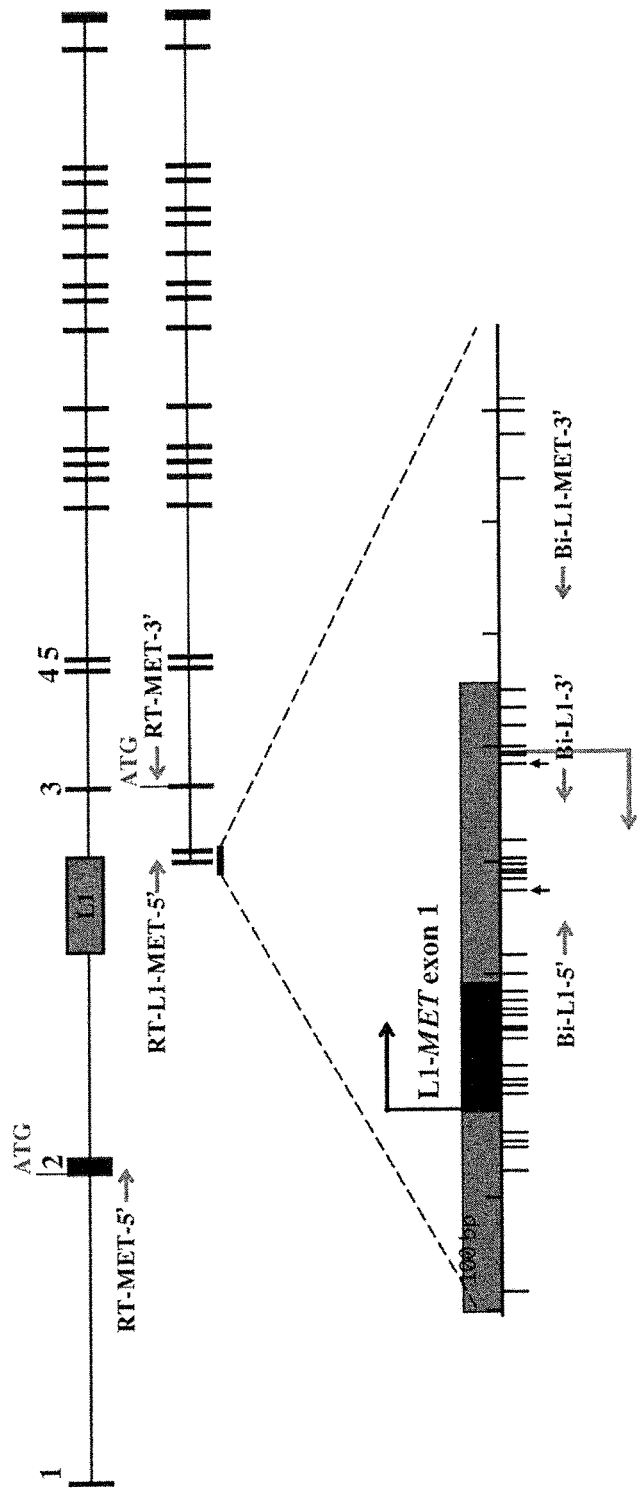
FIG. 7 shows the methylation and expression of L1-MET correlates in cell lines. A. Map of alternate transcript from L1-MET. Exons are represented by black boxes and a red box represents the specific L1. The bent arrows indicate transcriptional start sites and ATGs indicate translational start sites. Horizontal arrows indicate the primers for PCR of bisulfite converted DNA and RT-PCR. The bisulfite-specific primers Bi-L1-5' and Bi-MET-3' were used to amplify L1-MET for methylation analysis and Bi-L1-5' and Bi-L1-3' for global L1 methylation analysis. The RT-PCR primers, RT-L1-MET-5' and RT-MET-3' were used to amplify cDNA of the L1-MET transcript for expression analysis and RT-MET-3' and RT-MET-5' for the full length MET expression analysis. The lower tick marks represent each CpG site. Vertical arrows indicate the CpG sites analyzed by the Ms-SNuPE assay. B. L1-MET methylation (red bars) and L1 methylation (black bars) was analyzed by Ms-SNuPE in 8 normal tissues, one normal bladder fibroblast cell line (LD419), two non-tumorigenic urothelial cell lines (UROtsa and NK2426), and 20 bladder carcinoma cell lines. Values are the average of one CpG site for L1 and an average of two CpG sites for L1-MET from technical triplicates. Error bars represent the standard deviation. C. Expression of L1-MET was measured using real-time RT PCR in one normal bladder fibroblast cell line, two normal urothelial cell lines and 10 bladder carcinoma cell lines. There is clearly a strong correlation between DNA methylation and expression in all 13 cell lines examined. Values are the average from technical duplicates. Red bars indicate the methylation status of L1-MET, which is also represented in B, and green bars represent the level of expression relative to GAPDH.
Figure 7B:
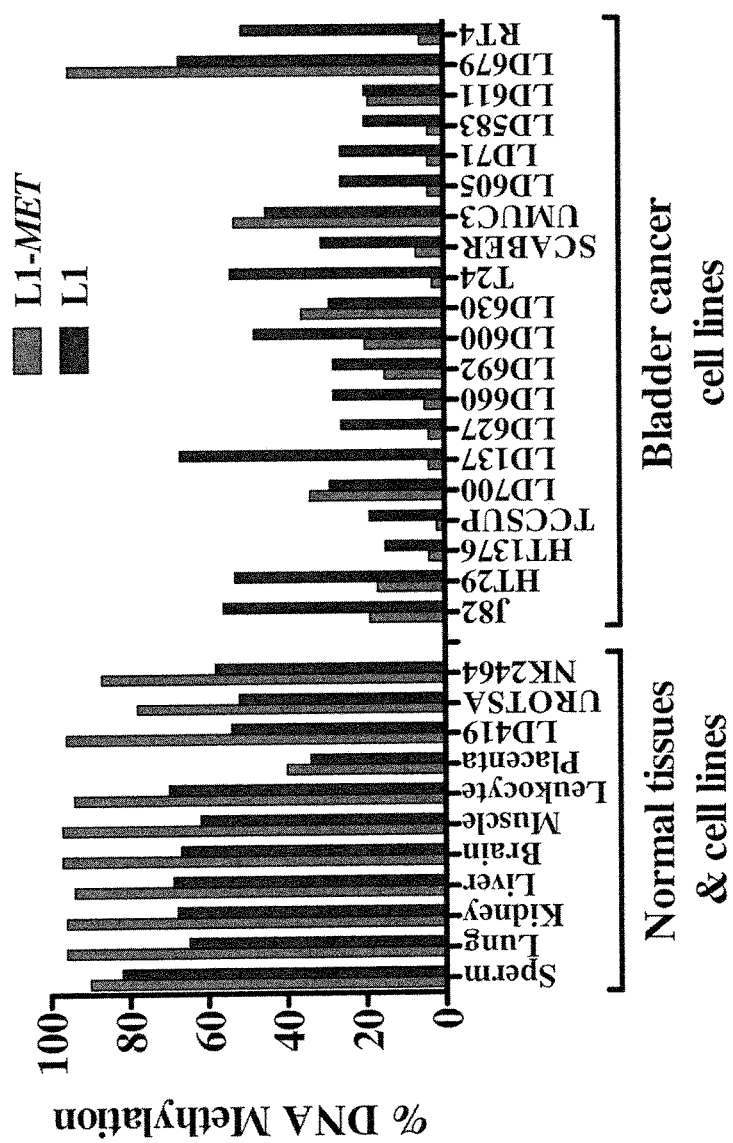

To examine the methylation status at a specific L1 we designed bisulfate-specific PCR primers with one located in the L1 promoter and the other in the surrounding intronic region of the host gene (FIG. 7A). The L1-MET promoter was highly methylated in normal cells and tissues, whereas 18 out of 20 of the bladder carcinoma cell lines showed significant hypomethylation ($p<3.4\times10^{-10}$) (FIG. 7B). We also measured methylation of global L1s using the standard assay with two primers that anneal within the L1 promoter (FIG. 7A). We found that hypomethylation of L1s was significant ($p<6.4\times10^{-5}$) but not as dramatic as L1-MET hypomethylation and that the methylation pattern can be quite different between global L1s and a specific L1, such as in the cell lines LD137, T24, and RT4 (FIG. 7B). This result clearly shows that global L1 status does not represent the status at specific L1s.

Figure 7C:
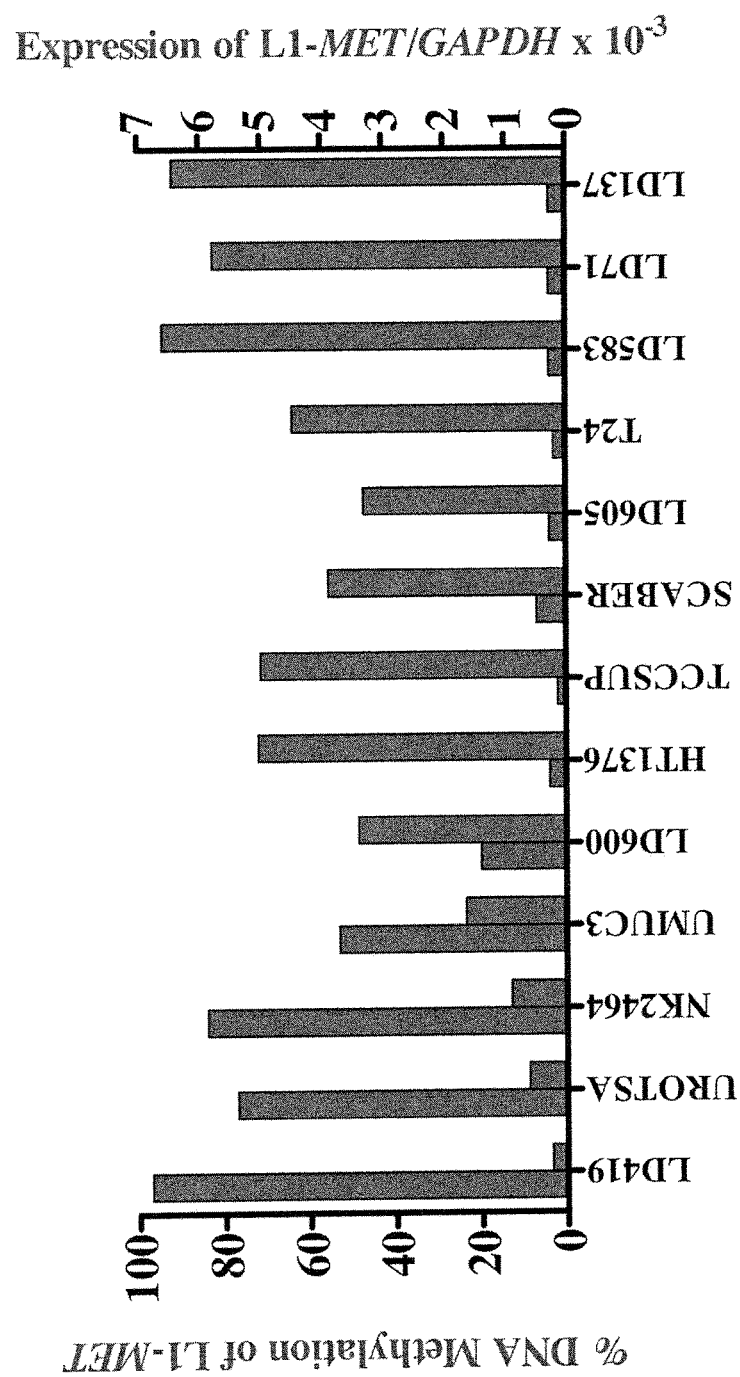
Figure 15D:
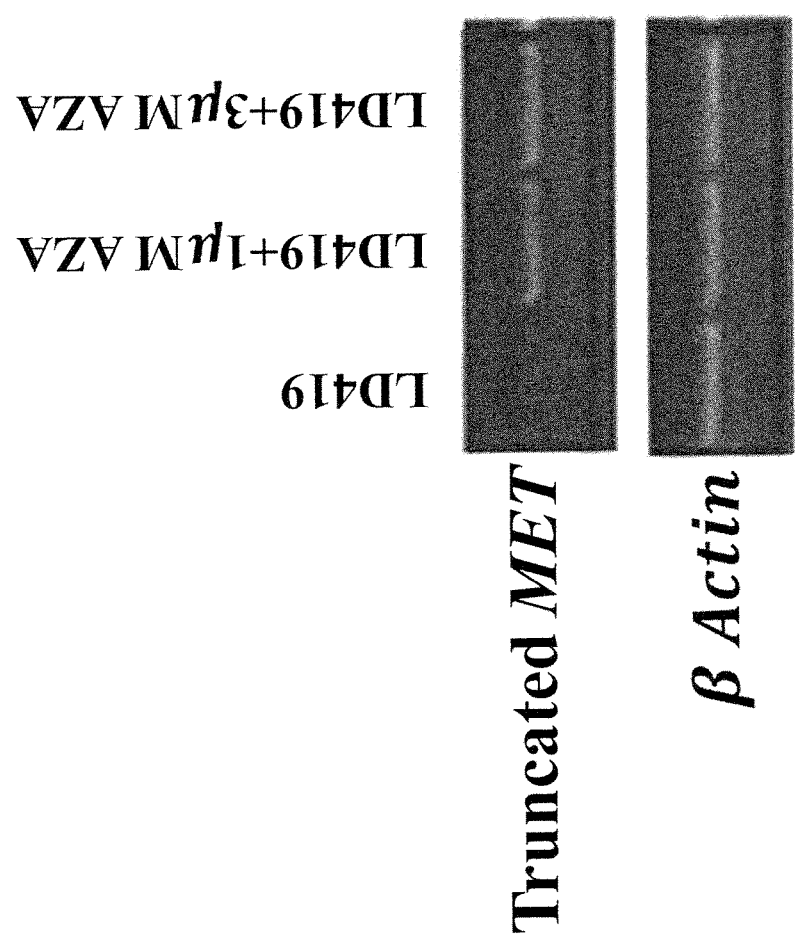
Figure 16A:
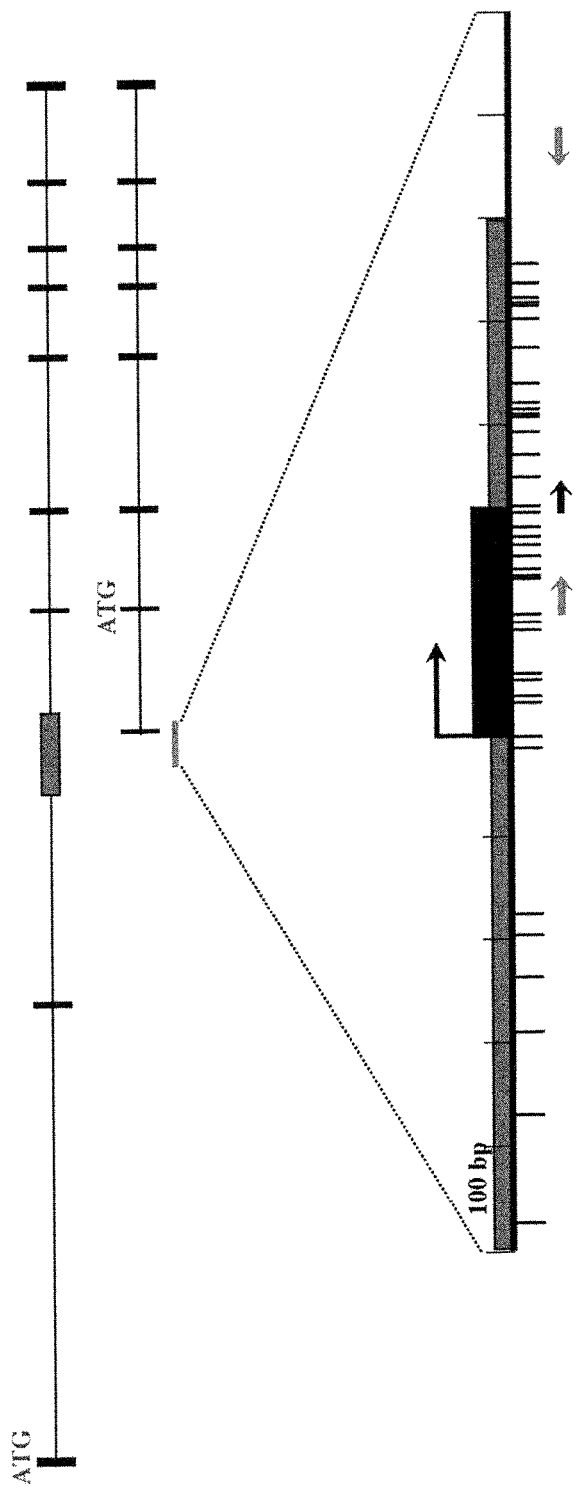
FIG. 16 shows the methylation and expression of L1-ACVRIC correlates in cell lines. (A) Map of alternate transcripts from L1-ACVRIC. Exons are represented by black boxes while the specific L1s are represented by red boxes. The lower tick marks represent each CpG site. The left bent arrow indicates transcriptional start sites and ATGs indicate translational start sites. Green arrows indicate the primers used to amplify the pyrosequencing product and the black arrow in between indicates the location of the pyrosequencing primer for L1-ACVRIC. (B) L1-ACVRlc methylation (red bars) and L1 methylation (black bars) was analyzed by pyrosequencing in 6 normal tissues, one normal bladder fibroblast cell line (LD419), one non-tumorigenic urothelial cell lines (UROtsa), and 10 bladder carcinoma cell lines. Values are the average of one CpG site for L1 and an average of two CpG sites for L1-ACVRIC from two technical duplicates. (C) Expression of L1-ACVRIC was measured using real-time RT PCR in one normal bladder fibroblast cell line, one normal urothelial cell line, and 10 bladder carcinoma cell lines. Values are also the average from two technical duplicates. Red bars indicate the methylation status of L1-ACVRIC, which is also represented in (B), and green bars represent the level of expression relative to GAPDH. Found at: doi:10.1371/journal.pgen. 1000917.s003 (0.86 MB TIF)
Figure 16B:
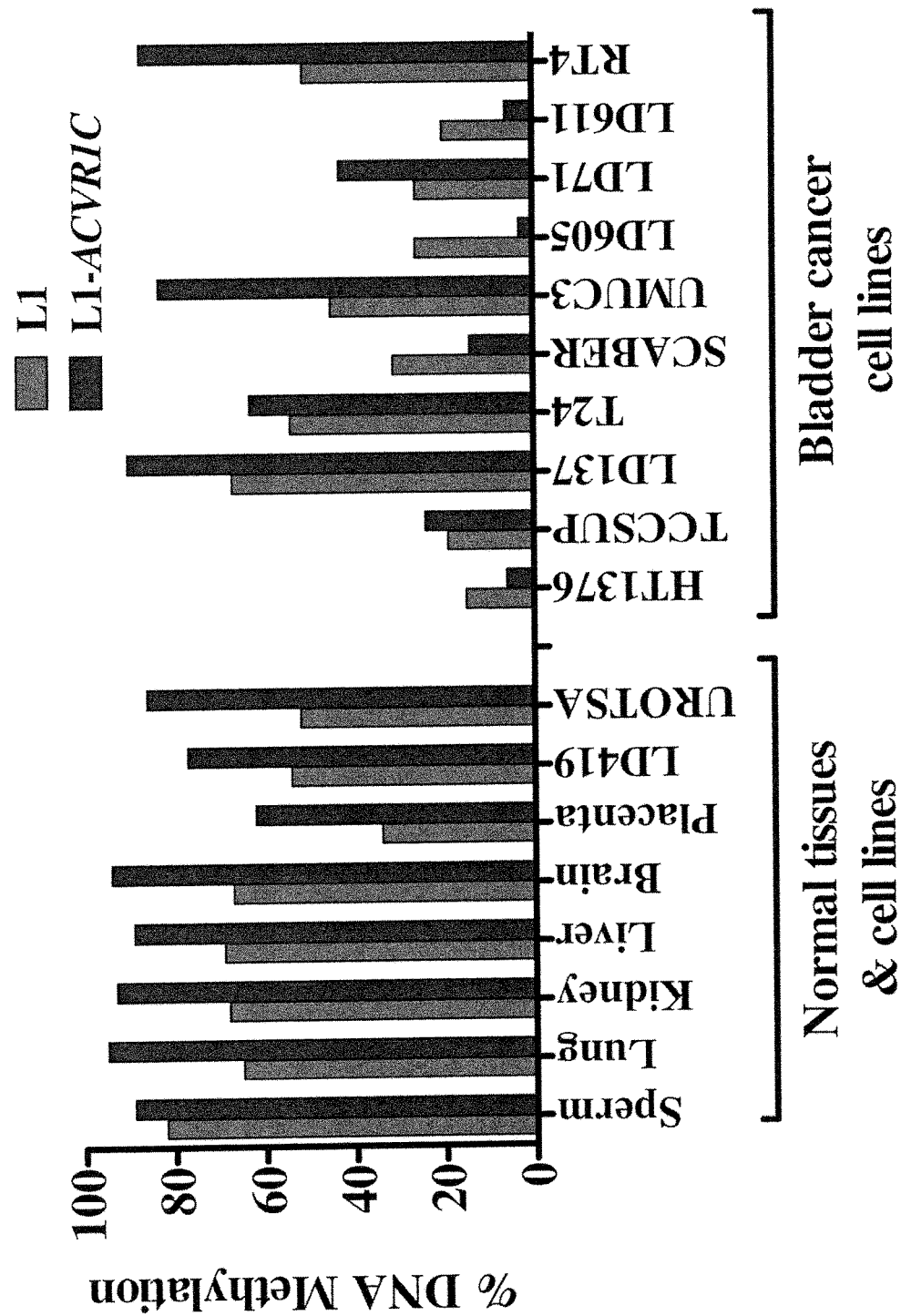
Figure 16C:
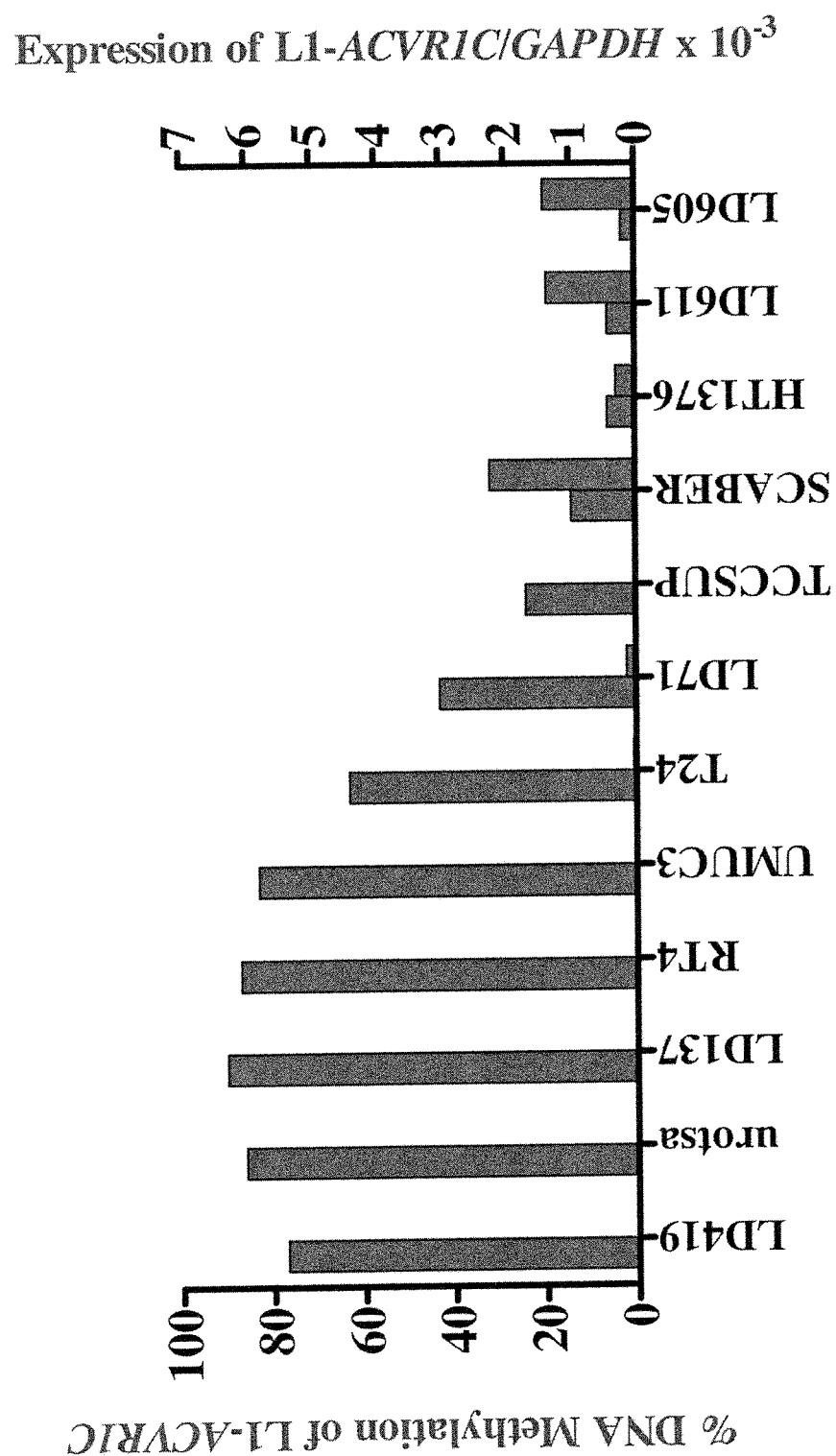
Figure 17A:
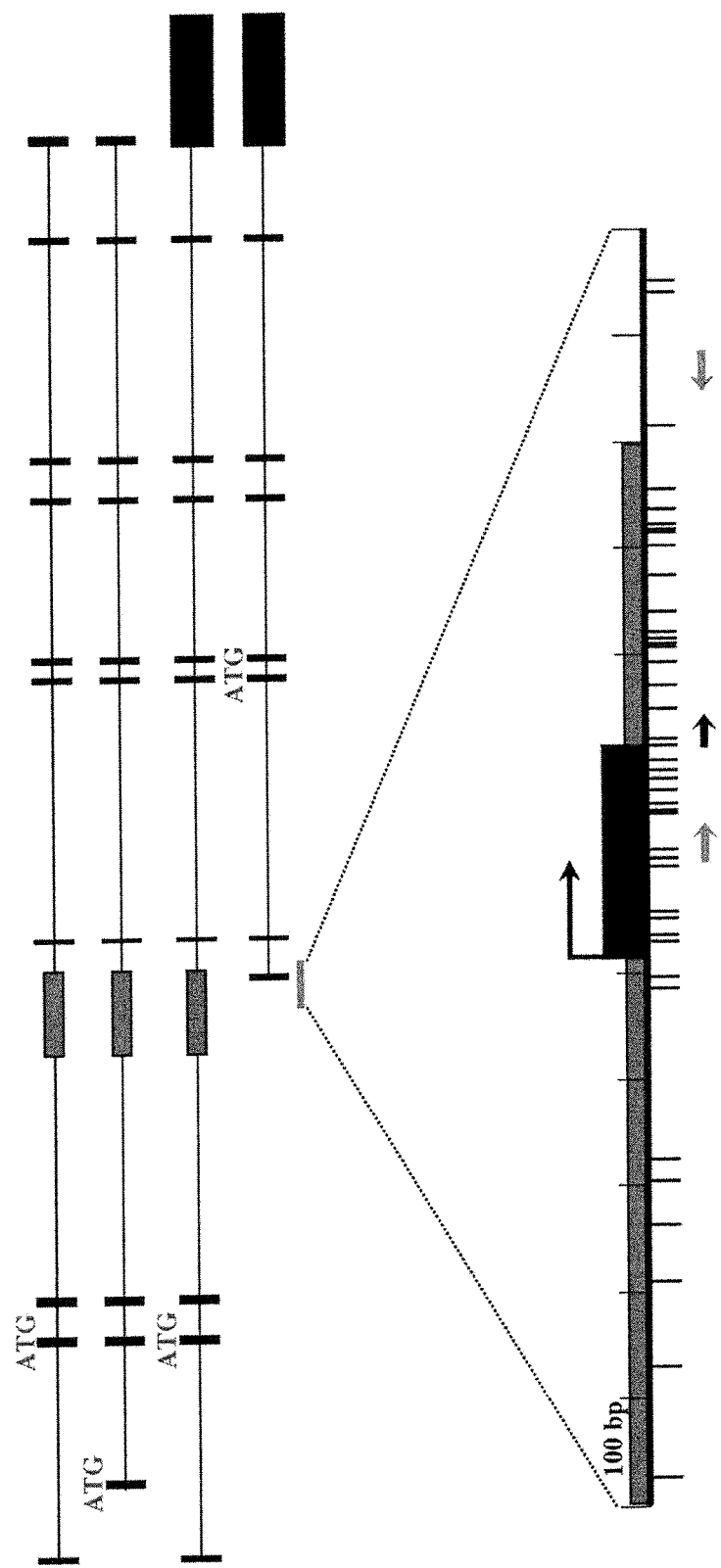
FIG. 17 shows the methylation and expression of L1-RAB3IP correlates in cell lines. (A) Map of alternate transcripts from L1-RAB3IP. Exons are represented by black boxes while the specific L1s are represented by red boxes. The lower tick marks represent each CpG site. The left bent arrow indicates transcriptional start sites and ATGs indicate translational start sites. Green arrows indicate the primers used to amplify the pyrosequencing product and the black arrow in between indicates the location of the pyrosequencing primer for L1-RAB3IP. (B) L1-RAB3IP methylation (red bars) and L1 methylation (black bars) was analyzed by pyrosequencing in 6 normal tissues, one normal bladder fibroblast cell line (LD419), one non-tumorigenic urothelial cell lines (UROtsa), and 10 bladder carcinoma cell lines. Values are the average of one CpG site for L1 and an average of two CpG sites for L1-RAB31F from two technical duplicates. (C) Expression of L1-RAB3IP was measured using real-time RT-PCR in one normal bladder fibroblast cell line, one normal urothelial cell line, and 10 bladder carcinoma cell lines. Values are also the average from two technical duplicates. Red bars indicate the methylation status of L1-RAB3IP, which is also represented in (B), and green bars represent the level of expression relative to GAPDH. Found at: doi:10.1371/journal.pgen.1000917.s004 (0.88 MB TIF)
Figure 17B:
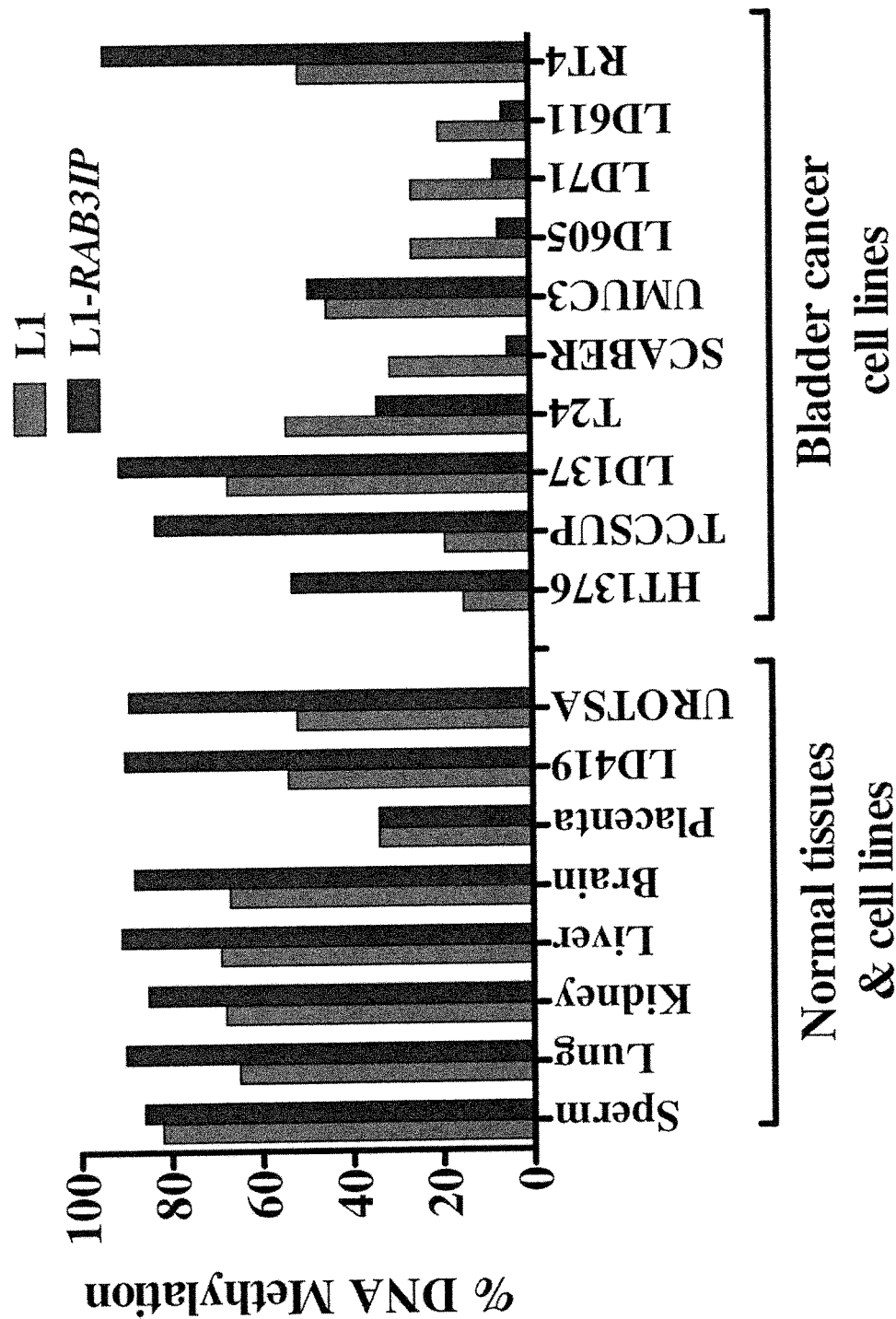
Figure 17C:
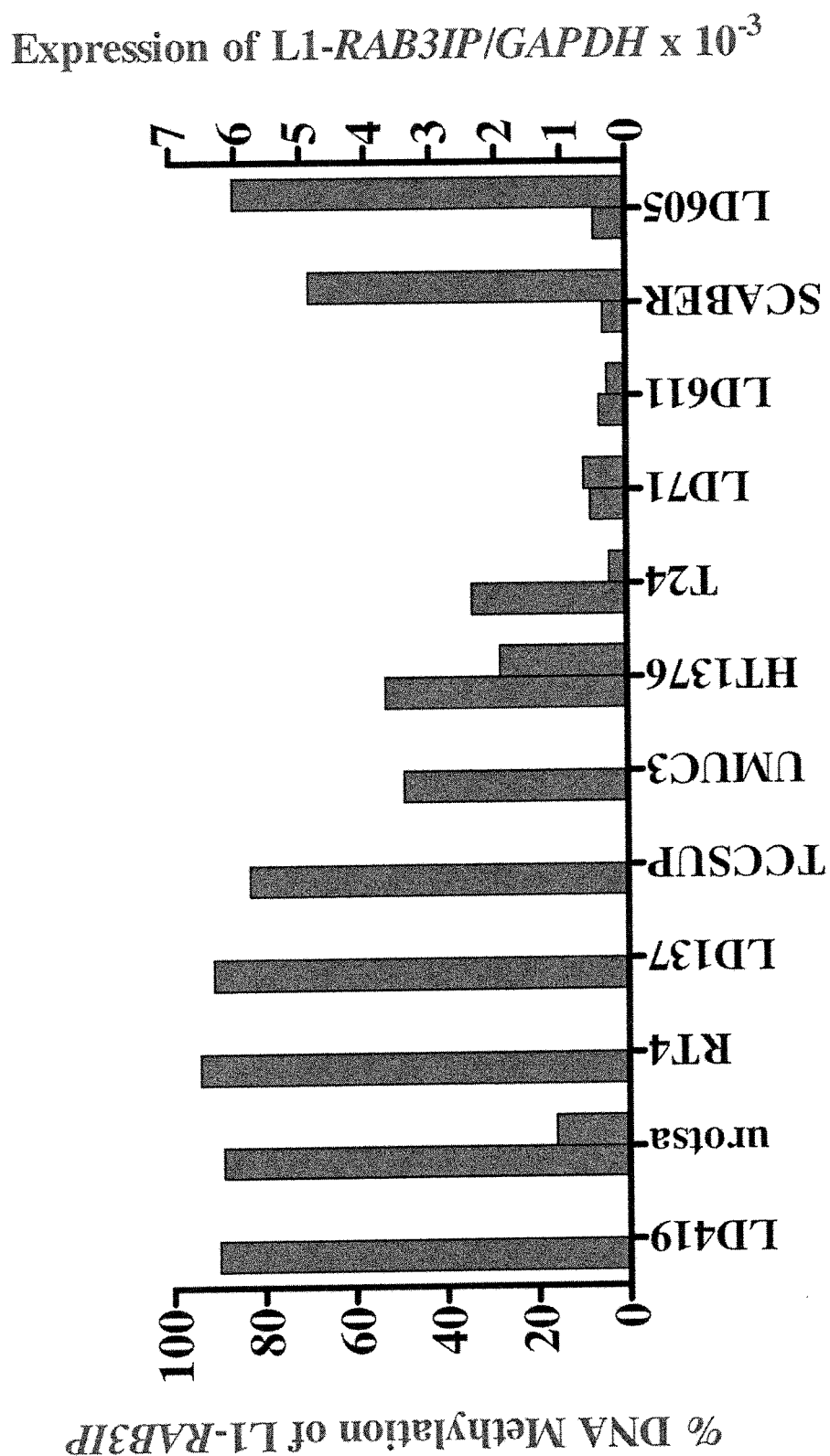

The transcript from the L1-MET anti-sense promoter contains its own exons 1 and 2, referred to as L1-MET exon 1 and L1-MET exon 2 (FIG. 7A). We designed RT-PCR primers with one primer located in either the MET exon 2 or the L1-MET exon 1 and one primer located in the shared exon 3 to examine the expression of the host gene MET and the alternate transcript from L1-MET, respectively (FIG. 7A). We confirmed the transcription start site of L1-MET by 5'RACE in the T24 bladder carcinoma cell line (FIG. 15C) in which the L1-MET promoter is completely unmethylated. The L1-MET transcript was lowly expressed in one bladder fibroblast cell line (LD419) and two non-tumorigenic urothelial cell lines, UROtsa [21] and NK2426 [22], and highly expressed in most bladder carcinoma cell lines (FIG. 7C). L1-MET was also not expressed in normal tissues except for placenta (data not shown). Therefore L1-MET hypomethylation correlated with the expression of the alternate transcript (FIG. 7C). Treatment of LD419 with the demethylating agent 5-aza-deoxycytidine lead to expression of L1-MET, suggesting that L1-MET is silenced by DNA methylation (FIG. 15D). We also designed bisulfite-specific PCR primers and RT-PCR primers for two additional specific L1s from the list shown in FIG. 14, which were randomly selected. One L1 was located within ACVR1c, a member of the TGF-Beta family able to induce apoptosis [23], and the other located in RAB3IP, and a protein whose exact function is unknown (FIGS. 16&17). Hypomethylation of these specific L1s also correlated with expression of their associated alternate transcripts, suggesting that DNA methylation plays a role in transcriptional silencing of functional L1 promoters in general (FIGS. 16&17).

Figure 9A:
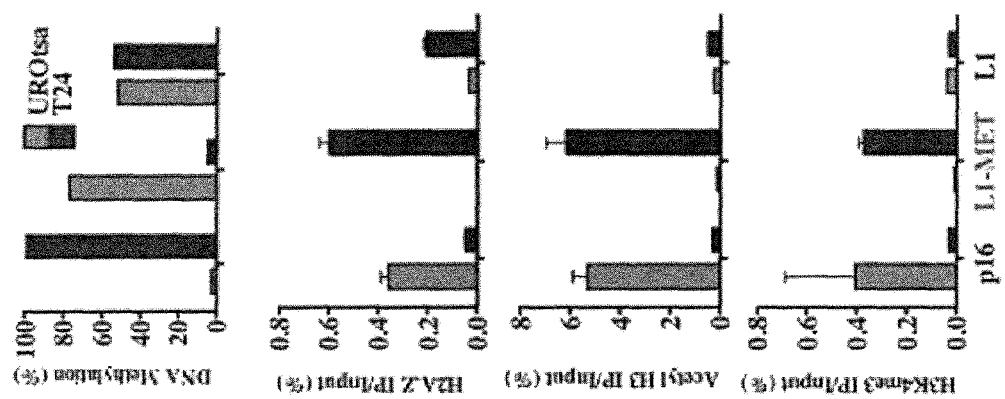
FIG. 9 shows that chromatin remodeling occurs at an active L1-MET promoter. A. DNA methylation at L1-MET and global L1s was determined by pyrosequencing in the immortalized urothelial cell line UROtsa and bladder carcinoma cell line T24. Chromatin immunoprecipitation was performed using antibodies for H3K4me3, acetylated H3, and H2A.Z. The values of the ChIP assay are the average of three experiments with technical duplicates. Error bars represent the standard deviation, and p16 represents a single copy gene control. The presence of active histone marks was associated with absence of DNA methylation at L1-MET in the cancer cell line. Methylase dependent single promoter analysis (MSPA) with M. CviPI, a GpC methyltransferase, of the B. endogenously methylated L1-MET promoter (ch7: 116364020-116364664) in the UROtsa immortalized urothelial cell line and the C. endogenously unmethylated L1-MET promoter in T24 bladder carcinoma cells. D. DNA methylation at L1-MET and global L1s was determined by pyrosequencing in the colon cancer cell line HCT116 and HCT116 DKO cells (DNMT1 hypomorph/DNMT3B knockout) [31,32]. Chromatin immunoprecipitation was performed using antibodies for H2A.Z. The presence of active histone marks was associated with absence of DNA methylation at L1-MET in the DKO cell line. Methylase dependent single promoter analysis (MSPA) with M. CviPI, a GpC methyltransferase, of the E. endogenously methylated L1-MET promoter in HCT116 colon cancer cells, and F. endogenously unmethylated L1-MET promoter in HCT116 DKO cells. White circles indicate unmethylated sites and black circles indicate methylated sites. Orange bars indicate areas of protection consistent with the presence of a nucleosome.
Figure 18A:
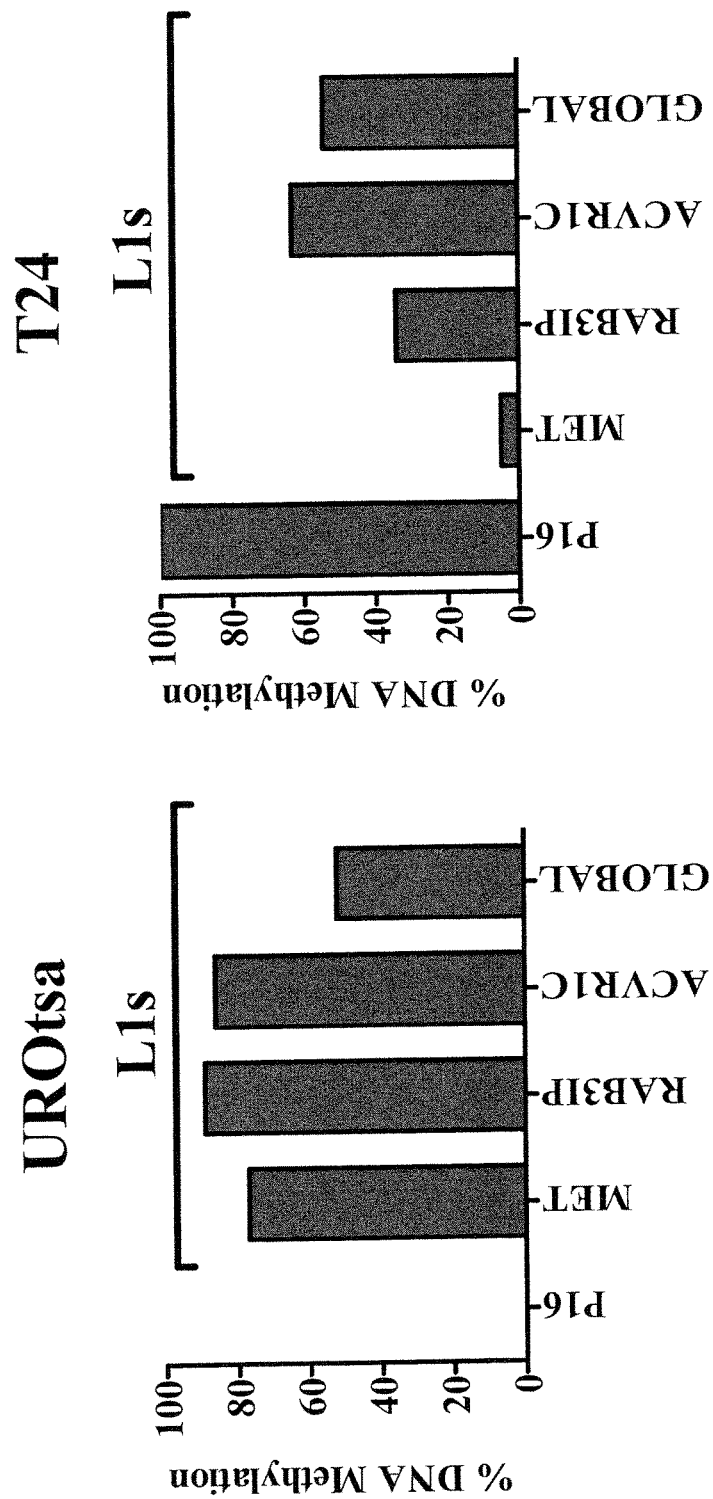
FIG. 18 shows that chromatin remodeling occurs at active L1 promoters. (A) DNA methylation at specific and global L1s (with p16 as a control) was determined by pyrosequencing in the immortalized urothelial cell line UROtsa and bladder carcinoma cell line T24. The specific L1s had less methylation in the cancer cell line. Chromatin immunoprecipitation was performed using antibodies for (B) H3K4me3; (C) acetylated H3; and (D) H2A.Z. The values of the ChIP assay are the average of three experiments with technical duplicates. Error bars represent the standard deviation. The presence of active histone marks was associated with absence of DNA methylation at the specific Ms in the cancer cell line. Found at: doi:10.1371/journal.pgen.1000917.s005 (0.67 MB TIF)
Figure 18B:
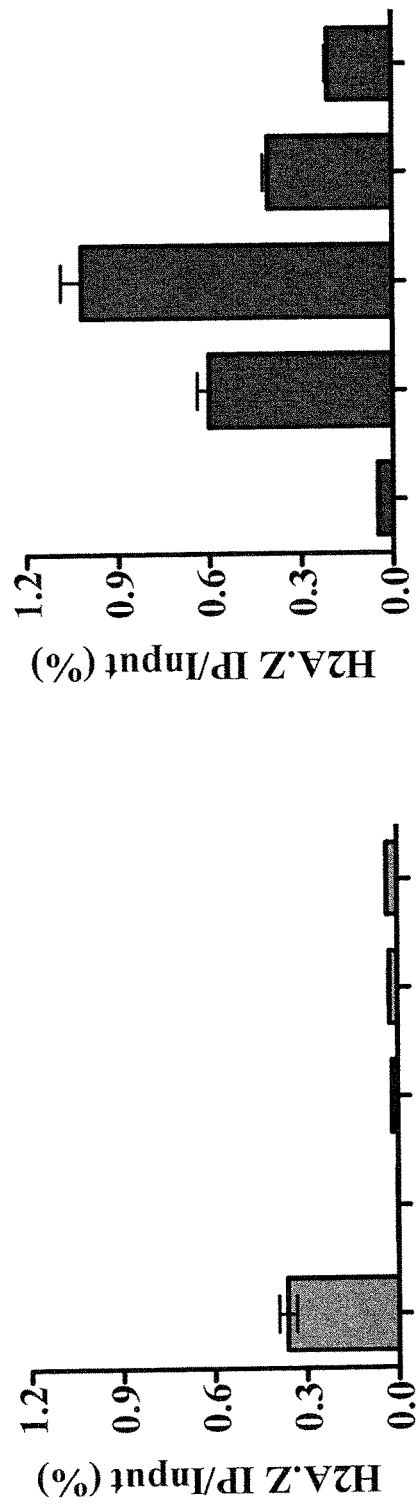

DNA methylation, silences the L1-MET promoter. The data presented thus far represents an association between hypomethylation of an L1 promoter and ectopic expression of an alternate transcript. To directly demonstrate that DNA methylation represses transcription of the bidirectional L1 promoter we utilized a luciferase promoter activity assay with a pCpGL luciferase reporter construct that has been modified to not contain any CpG sites [24]. Therefore, after insertion of the promoter sequence of interest the plasmid can be treated with the CpG methyltransferase M. SssI and the methyl donor S-adenosyl-methionine (SAM), allowing the promoter to be methylated without affecting the plasmid backbone. We created two plasmids, differing only the orientation of the L1-MET promoter, allowing us to measure either the L1 transcriptional activity or the L1-MET activity transcriptional activity (FIG. 8A). Activity in both directions was inhibited in the methylated plasmid (FIG. 8B). To our knowledge these data show for the first time that DNA methylation directly suppresses transcription from L1 promoter in both directions, indicating that the ectopic transcripts from Ms found in cancer [7] are a result of L1 hypomethylation. The relative activity between the two different promoters indicates that the L1-MET promoter is much weaker than the L1 promoter, Chromatin remodeling accompanies transcriptional activation of L1 promoters. In addition to DNA methylation, epigenetic regulation of gene transcription also involves chromatin structure, specifically covalent modifications of histones, incorporation of histone variants, and nucleosome occupancy. In mice the chromatin structure of global L1s has been studied, but not in the promoter region [25]. Very few studies have addressed the chromatin structure at repetitive elements in humans. We took advantage of our ability to examine specific Ms to analyze the chromatin remodeling that occurs between the promoters of inactive and active repetitive elements in humans. Using chromatin immunoprecipitation (ChIP) we found that the level of DNA methylation at each specific L1 is inversely proportional to the level of enrichment of active histone marks (FIG. 9A & FIG. 18), and the chromatin structure at global L1s did not correlate with the specific Ms. Comparing the structure of the unmethylated L1-MET promoter in T24 bladder carcinoma cells to the methylated L1-MET promoter in UROtsa urothelial cells revealed a gain of the active marks H3K4me3 and acetylated H3 and the histone variant H2A.Z (FIG. 9A). Therefore transcriptional activation of a repetitive element results in a similar pattern of chromatin remodeling found in active single copy genes such as p16 (FIG. 9A) [12,26,27].

A switch from a tetranucleosome to dinucleosome structure accompanies transcriptional activation of the L1-MET promoter. Methylase-sensitive Single Promoter Analysis (M-SPA) has previously been used to obtain single molecule resolution of nucleosome positioning at unmethylated CpG island promoters [28]. Briefly, nuclei are isolated and treated with the CpG methyltransferase M. SssI, followed by DNA extraction, bisulfate conversion, and genomic sequencing of individual clones. The resulting pattern of applied DNA methylation reveals patches of protection, indicating the location of nucleosomes on individual molecules. Previously, the main limitation of the M-SPA method was that it could not be used to assess nucleosome positioning in an endogenously methylated region. However, the enzyme M. CviPI, which methylates GpC sites [29], can be used to avoid this problem since endogenous GpC sites are not methylated in humans except in the context of a GpCpG. Therefore, by modifying our M-SPA method by using a GpC methyltransferase we have conducted the first single molecule analysis of nucleosome positioning at a methylated promoter and, in combination with our ability to study specific L1s, have shown the nucleosome occupancy at a single repetitive element in both an active and inactive state.

Figure 9B:
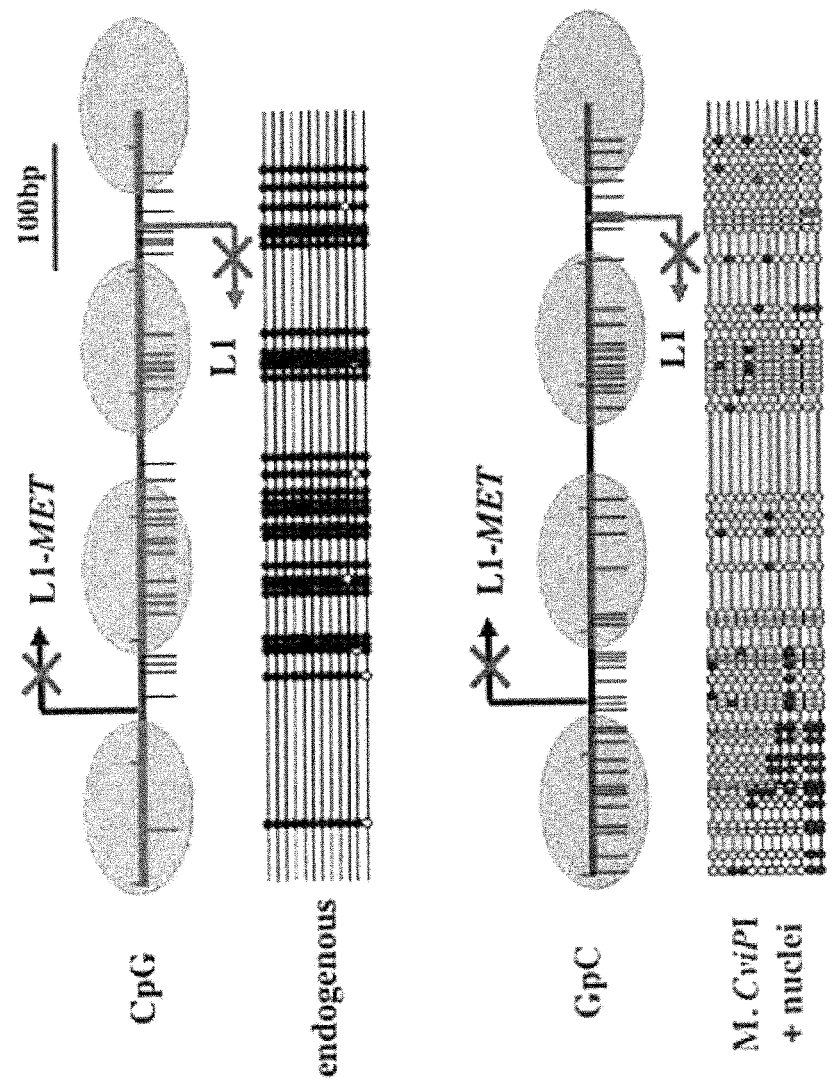
Figure 9C:
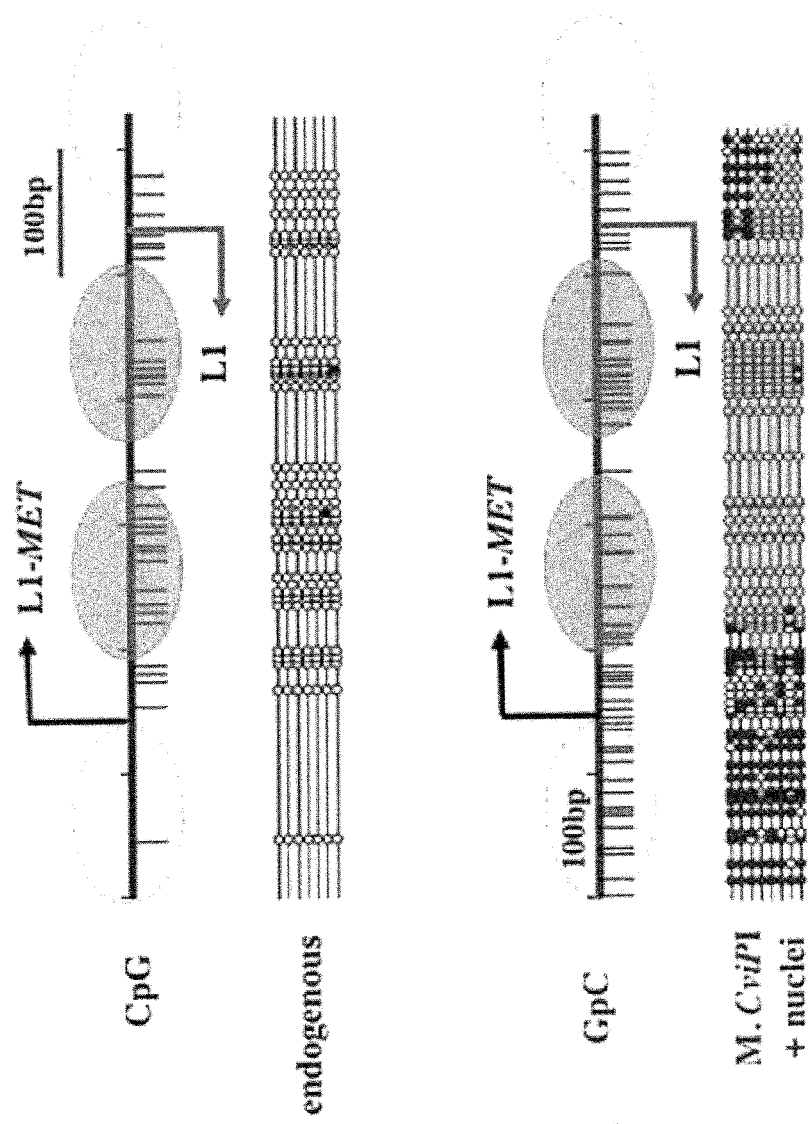
Figure 19:
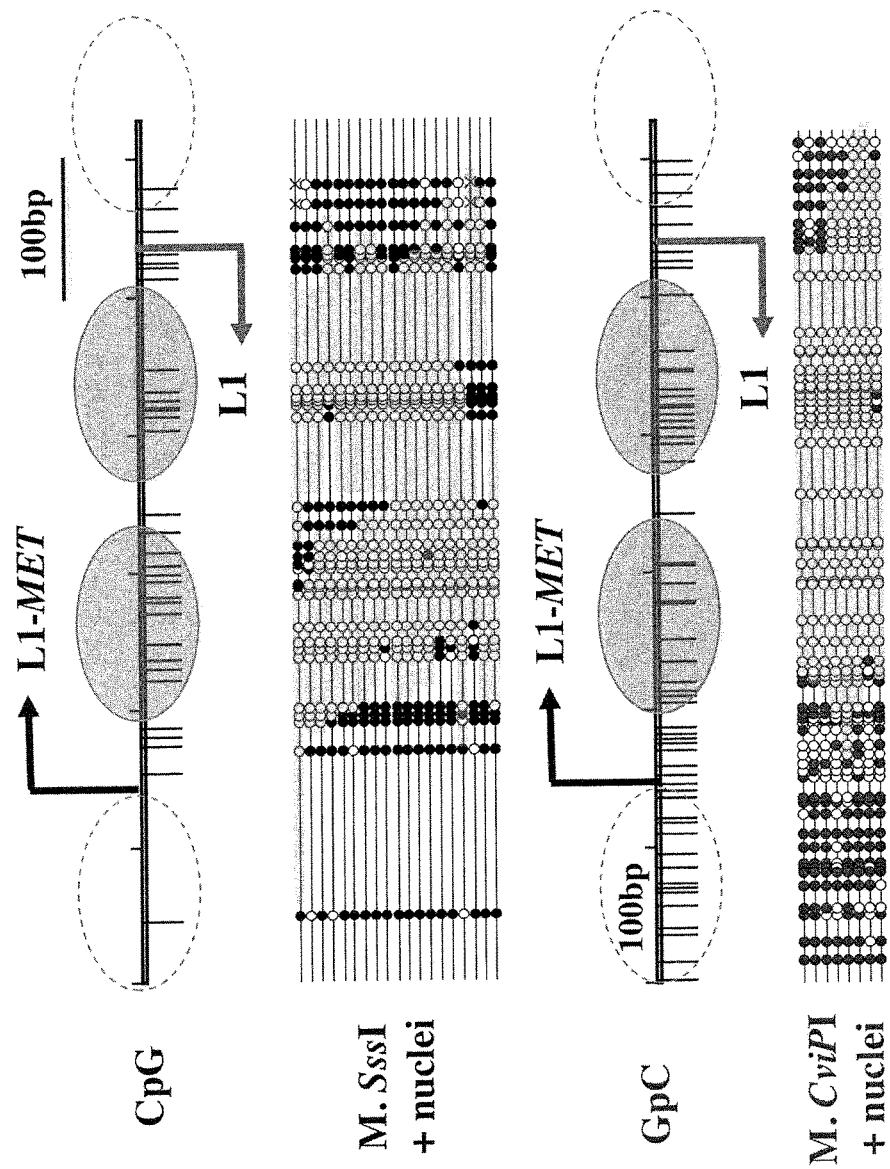
FIG. 19 shows that chromatin remodeling occurs an active L1-MET promoter. Nucleosome positioning in an active fully unmethylated L1-MET promoter in T24 bladder carcinoma cells reveals a dinucleosomal structure, as determined by both M. SssI, a CpG methyltransferase and M. CviPI accessibility. Found at: doi:10.1371/journal.pgen. 1000917.s006 (1.29 MB TIF)
Figure 20A:
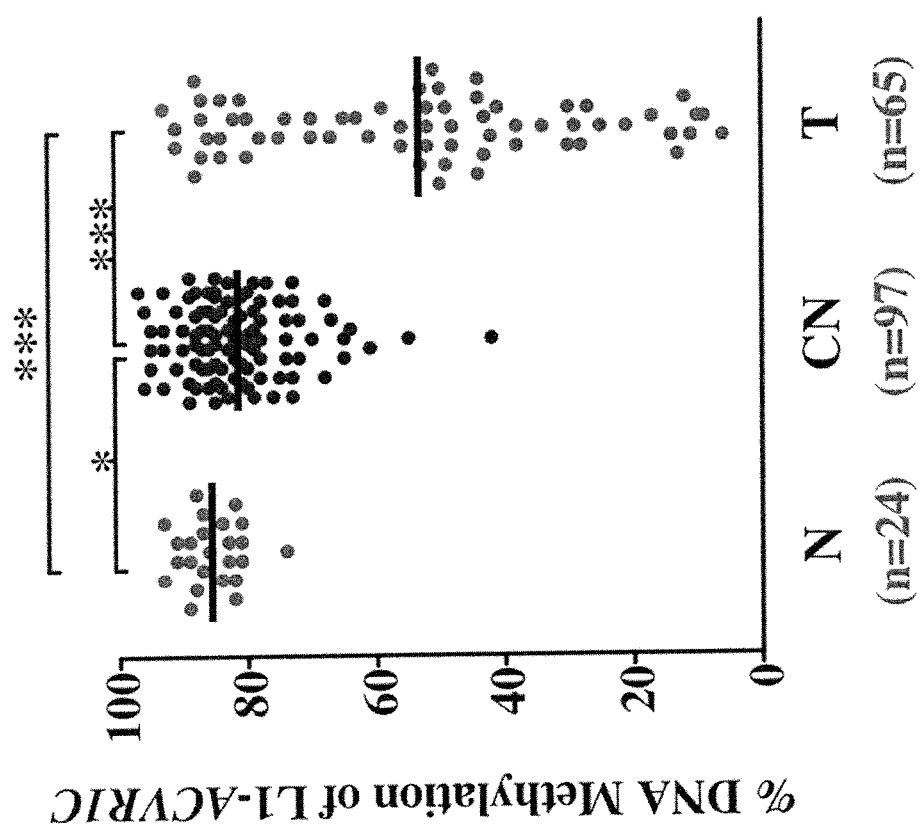
FIG. 20 shows that methylation and expression status of specific L is correlates in bladder tissues. Horizontal lines represent the mean. (A) Methylation status of L1-ACVRIC was analyzed by pyrosequencing in normal tissues (N), corresponding normal tissues (CN), and bladder tumors (T). Values are an average of two CpG sites. (B) Expression of the alternate transcript from L1-ACVR1c and (C) the host gene ACVRIC, and the control gene GAPDH was measured by real-time RT-PCR. * represents p<0.001,  represents p<0.01, and * represents p<0.05. (D) Methylation status of L1-RABSIP was analyzed by pyrosequencing in normal tissues (N), corresponding normal tissues (CN), and bladder tumors (T). Values are an average of two CpG sites. (E) Expression of the alternate transcript from L1-RAB31P and F. the host gene RAB31P, and the control gene GAPDH was measured by real-time RT-PCR. * represents p<0.001,  represents p<0.01, and * represents p<0.05 as determined by the Mann-Whitney test. While there are no error bars for the clinical sample analysis due to the extremely limited amount of sample DNA. the results show a consistent trend. Found at: doi:10.1371/journal.pgen.1000917.s007 (0.58 MB TIF)
Figure 20B:
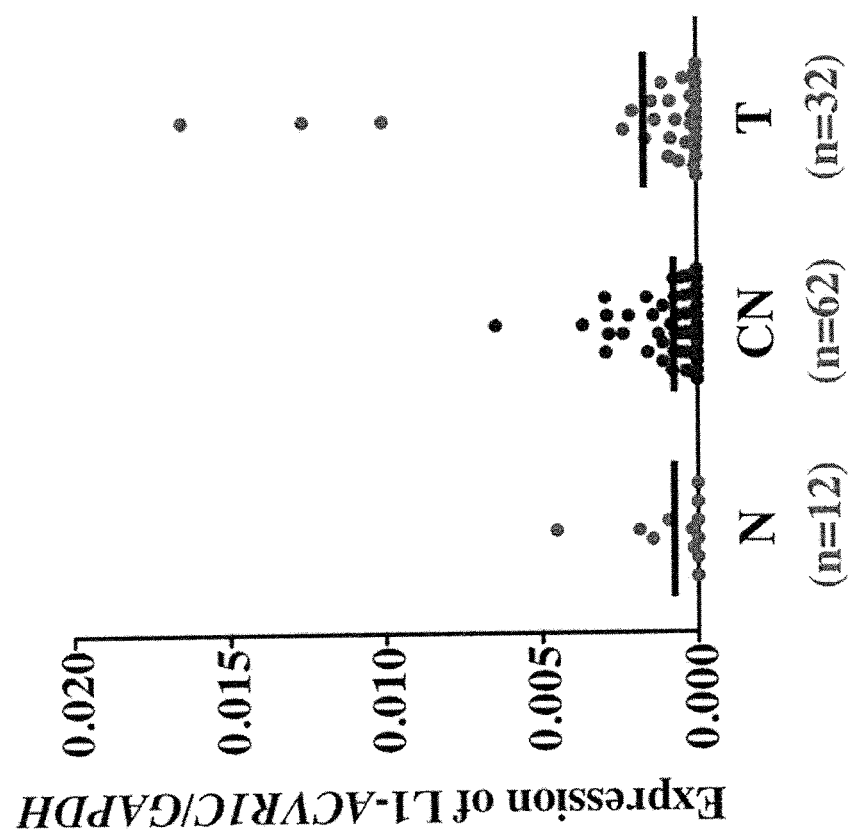
Figure 20C:
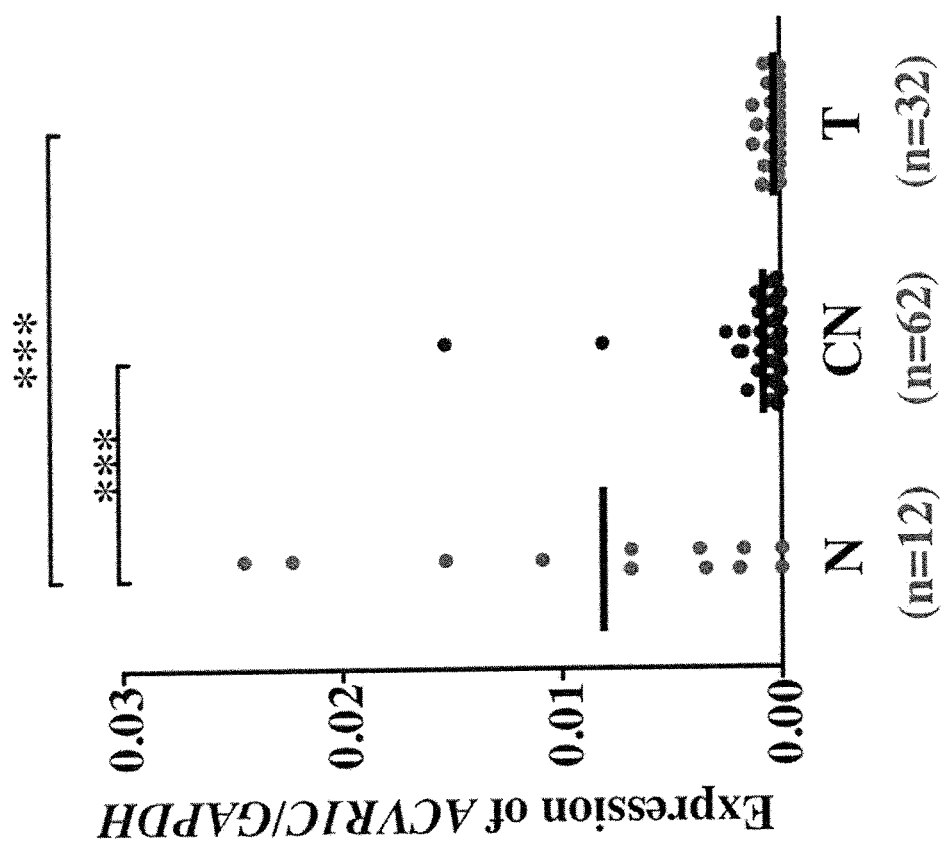
Figure 20D:
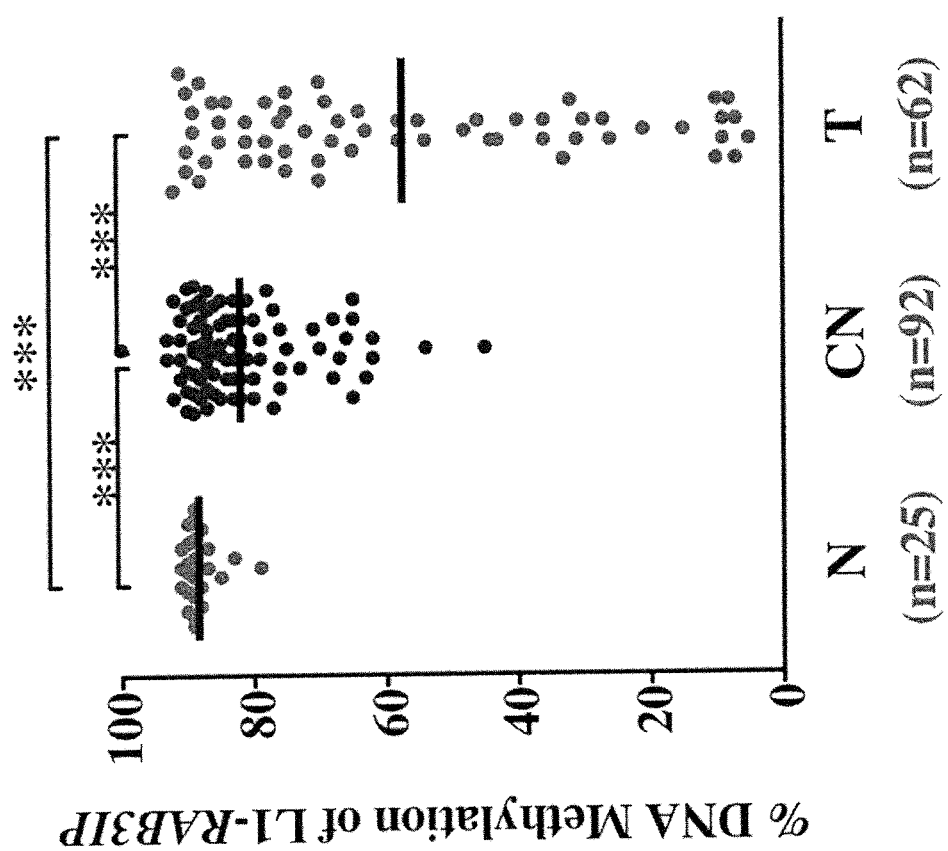
Figure 20E:
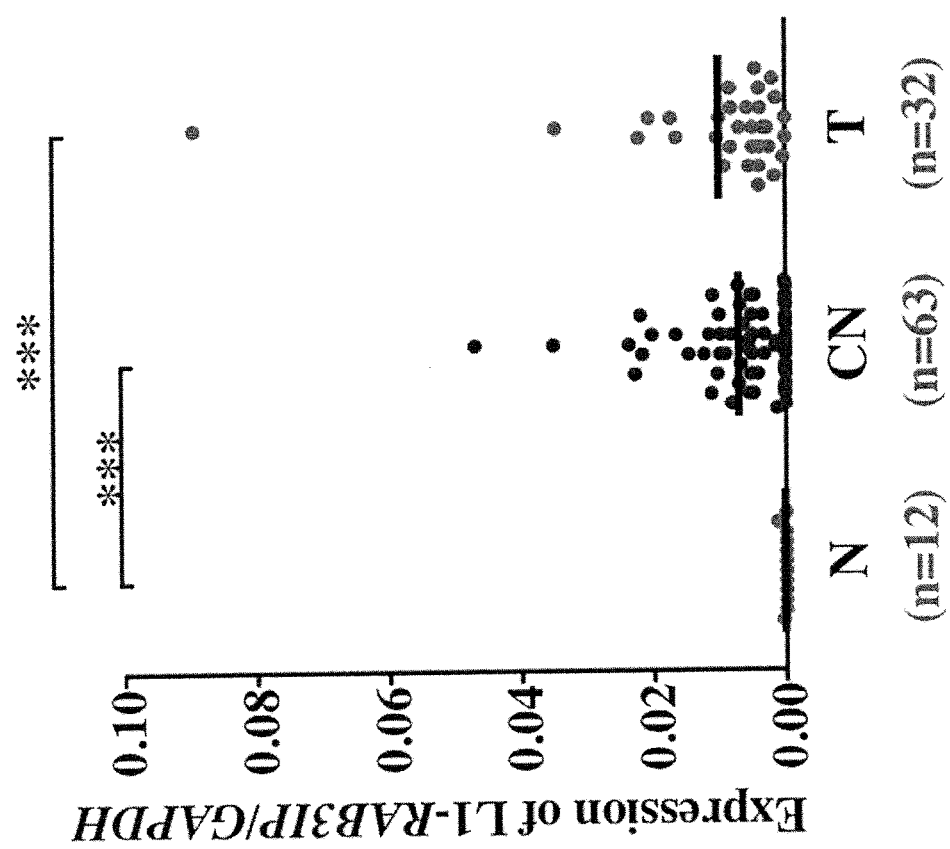
Figure 20F:
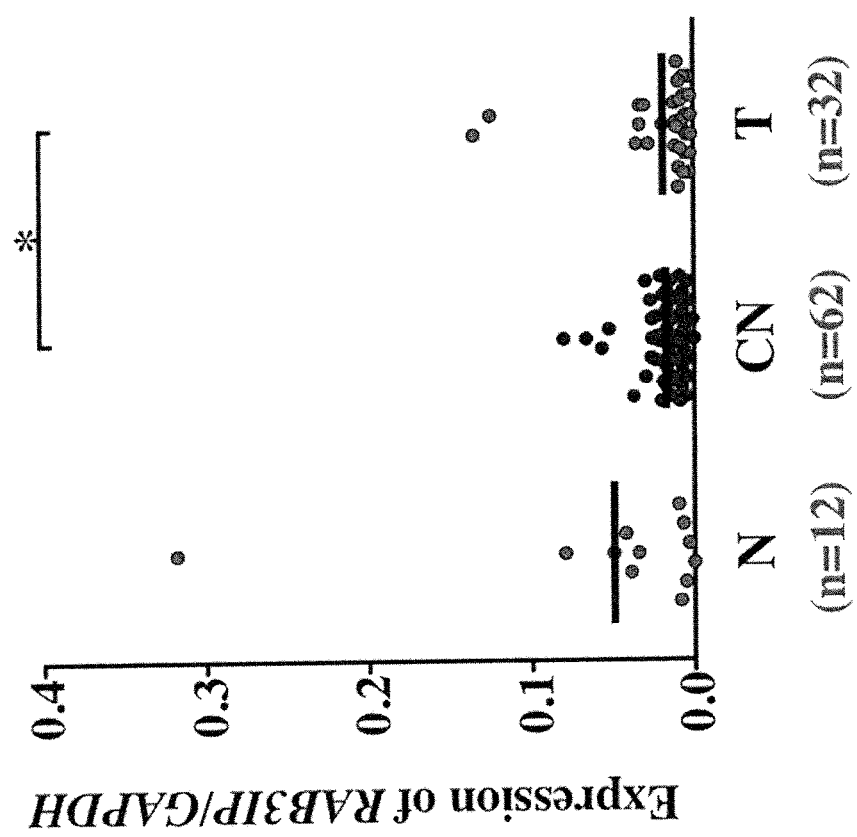

The endogenously methylated L1-MET promoter in the UROtsa immortalized urothelial cell line was completely occupied by nucleosomes, revealing that the methylated L1-MET promoter exists in a tetranucleosomal structure (FIG. 9B). GpCpG sites were excluded from analysis since it is not possible to distinguish between endogenous CpG methylation and enzyme-induced GpC methylation at such loci. When we performed the same assay on T24 cells in which L1-MET is unmethylated we found a nucleosome occupying the region downstream of each of the two transcription start sites and no nucleosome upstream of either (FIG. 9C). We were able to confirm the results in T24 cells using the CpG methyltransferase M. SssI, since L1-MET was not endogenously methylated (FIG. 19). However, the number and location of CpG sites limits the resolution of this assay since the region upstream of the L1-MET start site contains only one CpG site. Therefore, the GpC methyltransferase allowed an increased resolution for this method. The unmethylated MLH1 promoter was used as a positive control for both CpG and GpC methyltransferase activity and accessibility (data not shown).

Figure 9D:
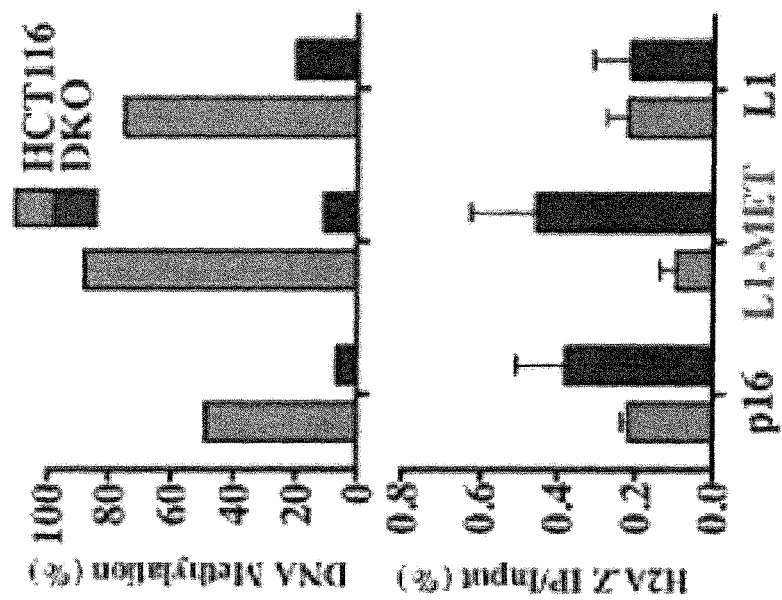
Figure 9E:
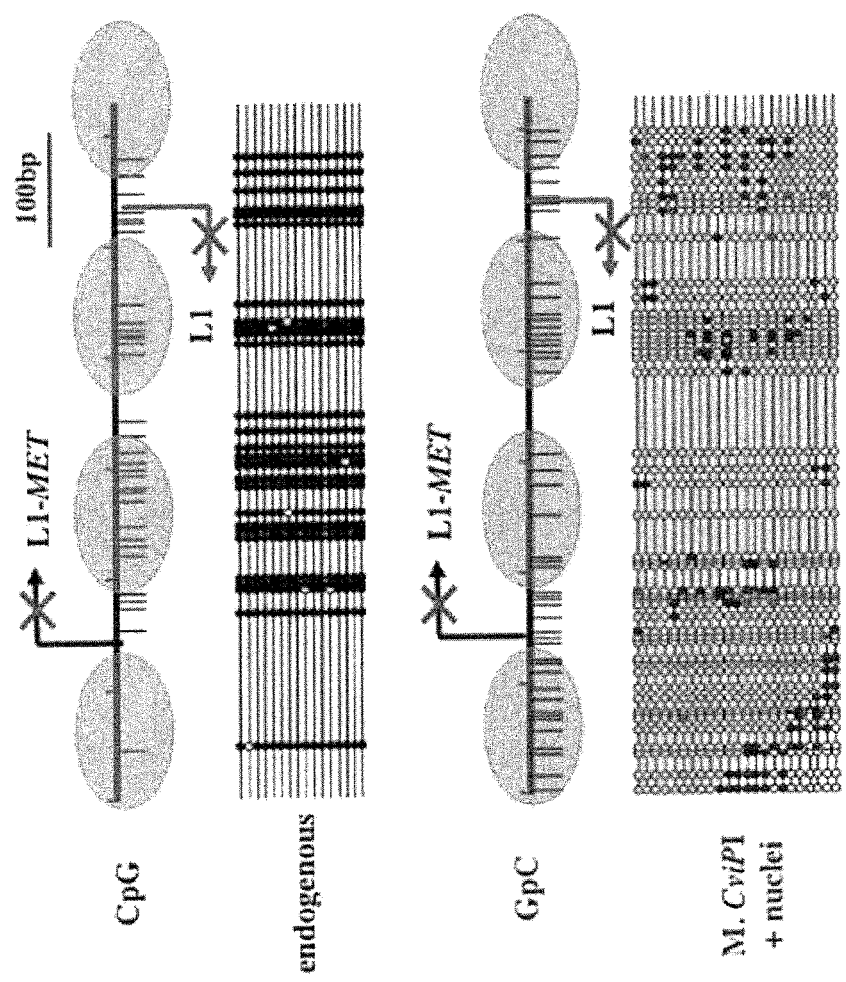
Figure 9F:
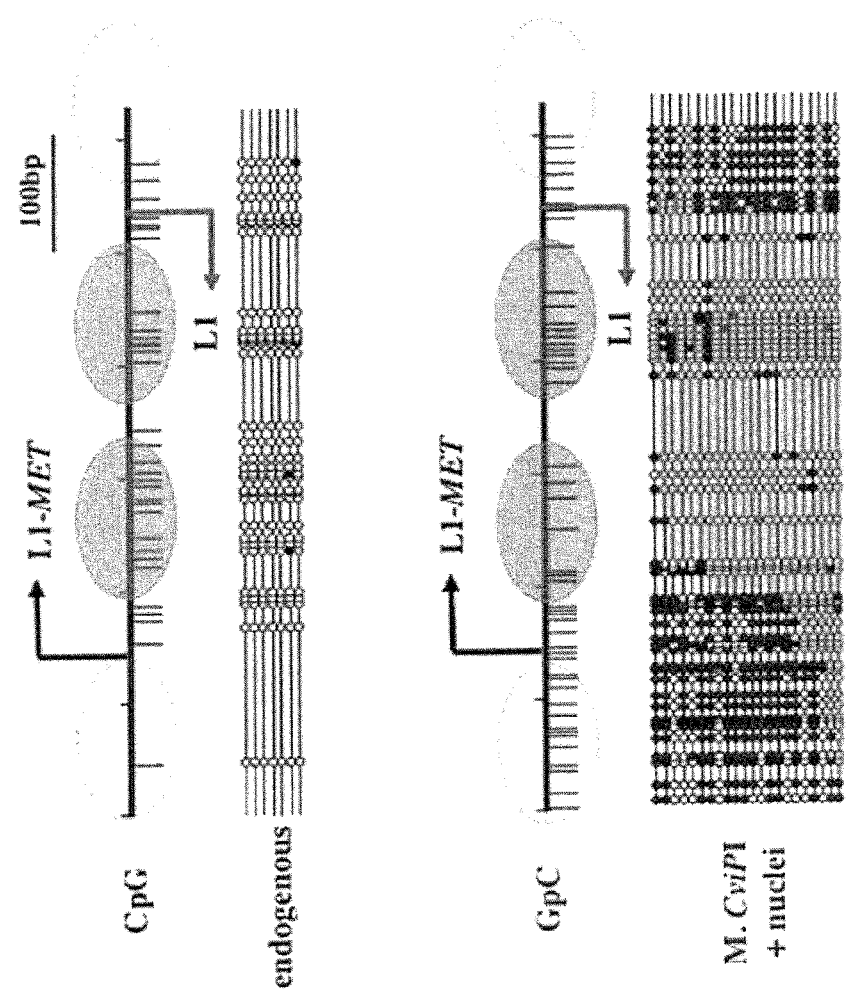

Previous work on the MLH1 bidirectional promoter has demonstrated that while each transcription start site loses the nucleosome directly upstream when active (−1 nucleosome), the nucleosome directly downstream is always maintained (+1 nucleosome) [27,30]. The L1 promoter is a different type of bidirectional promoter that generates partially overlapping sense and antisense transcripts, commonly referred to as an antisense promoter (ASP). The L1 ASP has room for two nucleosomes between the two transcription start sites, therefore each start site has its own +1 nucleosome. These two +1 nucleosomes are maintained while the active promoter loses the −1 nucleosome at both starts sites. Therefore the inactive L1 promoter exists in a tetranucleosomal state (two +1 and two −1 nucleosomes) while the active promoter exists in a dinucleosomal state (two +1 nucleosomes). In addition, when DNA methylation levels are reduced by knocking out expression of 2 of the 3 methyltransferases responsible for maintaining DNA methylation, DNMT1 and DNMT3B [31,32], we see acquisition of H2A.Z at L1-MET and global L1s (FIG. 9D) along with induction of expression of L1-MET (data not shown) and nucleosome eviction at the L1-MET promoter (FIGS. 9E&F), revealing that a switch from an inactive tetranucleosomal structure to an active dinucleosomal structure accompanies hypomethylation.

Figure 10:
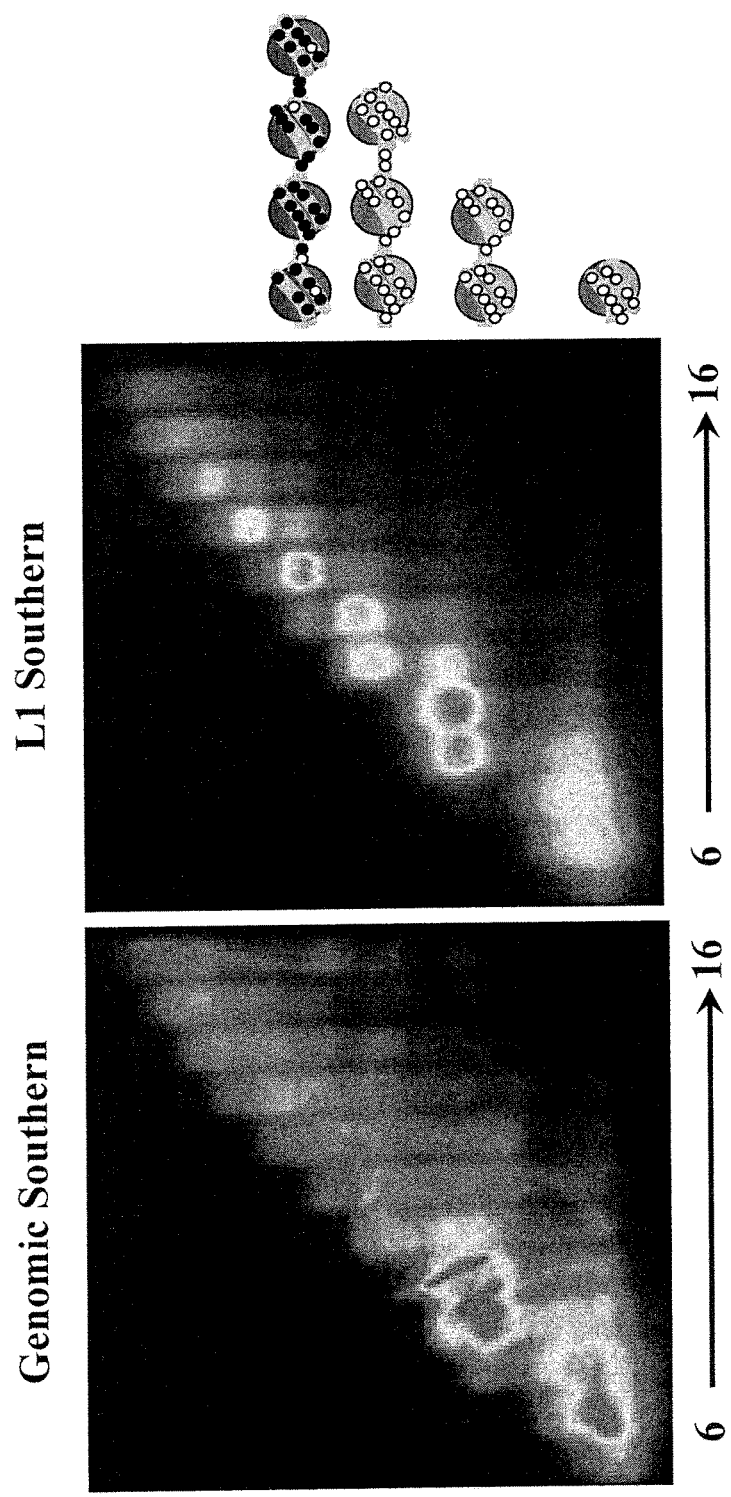
FIG. 10 shows that nucleosome eviction is a frequent occurrence at L1 promoters. Partial MNase digestion of nucleosomes was followed by fractionation by a sucrose density gradient. When a Southern for genomic DNA was performed on the DNA in each fraction (6-16), enrichment in the mono- and dinucleosome fractions was revealed. When a Southern for L1s was performed enrichment of L1s in the di- and tetranucleosome fractions was found. According to our model the L1 promoters with a tetranucleosomal structure should be inactive and methylated.

Many L1 promoters exist in an active chromatin structure. While a single-molecule analysis of the nucleosome occupancy at the L1-MET promoter confirmed that an active L1 promoter switches from a tetranucleosomal structure to a dinucleosomal structure, we cannot generalize that other L1s exist in these states. To do so we took a cancer cell line that has a methylated and inactive L1-MET promoter, the colon cancer cell line HCT116, and performed chromatin fractionation using MNase digestion followed by sucrose gradient ultracentrifugation [33]. The fractions were run on an agarose gel and a genomic Southern using radioactively labeled input DNA was performed. Most of the DNA was present in the mononucleosome and dinucleosome fractions (FIG. 10). When the same blot was probed with the L1 promoter sequence, the distribution of global L1 promoters showed enrichment in both the dinucleosome and tetranucleosome fractions, indicating that other L1s besides L1-MET could exist in an inactive tetranucleosome or active dinucleosome structure (FIG. 10).

Figure 11A:
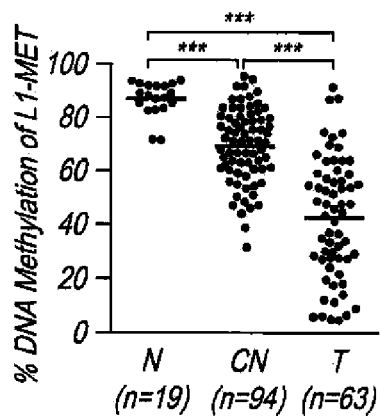
FIG. 11 shows that methylation and expression status of L1-MET correlates in bladder tissues. Horizontal lines represent the mean and n the number of patient samples. A. Methylation status was analyzed by Ms-SNuPE in normal tissues (N, green), corresponding normal tissues (CN, dark blue), and bladder tumors (T, red). Values are an average of two CpG sites. B. Expression of the alternate transcript from L1-MET and C. the host gene MET, and the control gene GAPDH was measured by real-time RT-PCR. * represents $p<0.001$,  represents $p<0.01$, and * represents $p<0.05$ as determined by the Mann-Whitney test. While there are no error bars for the clinical sample analysis due to the extremely limited amount of sample DNA, the results show a consistent trend.
Figure 11B:
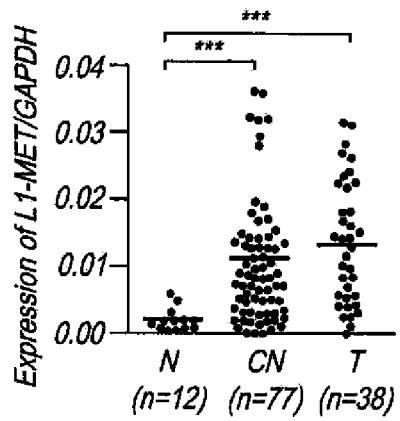
Figure 11C:
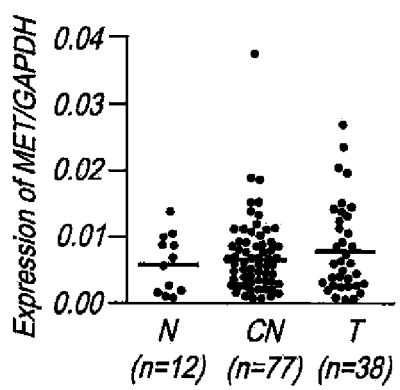

Hypomethylation of and expression from specific L1s occurs in bladder tumors. Since bladder tumors display both hypomethylation of L1s [34] and overexpression of MET [16-18], our next step was to determine whether hypomethylation of the specific L1 promoters and their associated alternate transcripts, including L1-MET, were present in uncultured bladder tumors. We found high levels of methylation at L1-MET and low expression in normal bladder epithelium obtained from age-matched cancer free bladders (FIGS. 11A&B) and significant hypomethylation of, and expression from, L1-MET in bladder tumors (FIGS. 11A&B). We also examined the methylation and expression of two additional specific L1 promoters located within host genes (FIG. 20). Hypomethylation of the L1-ACVR1c and L1-RAB3IP promoters occurred in bladder tumors (FIG. 20). Therefore we have provided the first clinical evidence that hypomethylation of functional L1 promoters results in ectopic gene expression during tumorigenesis.

Figure 21A:
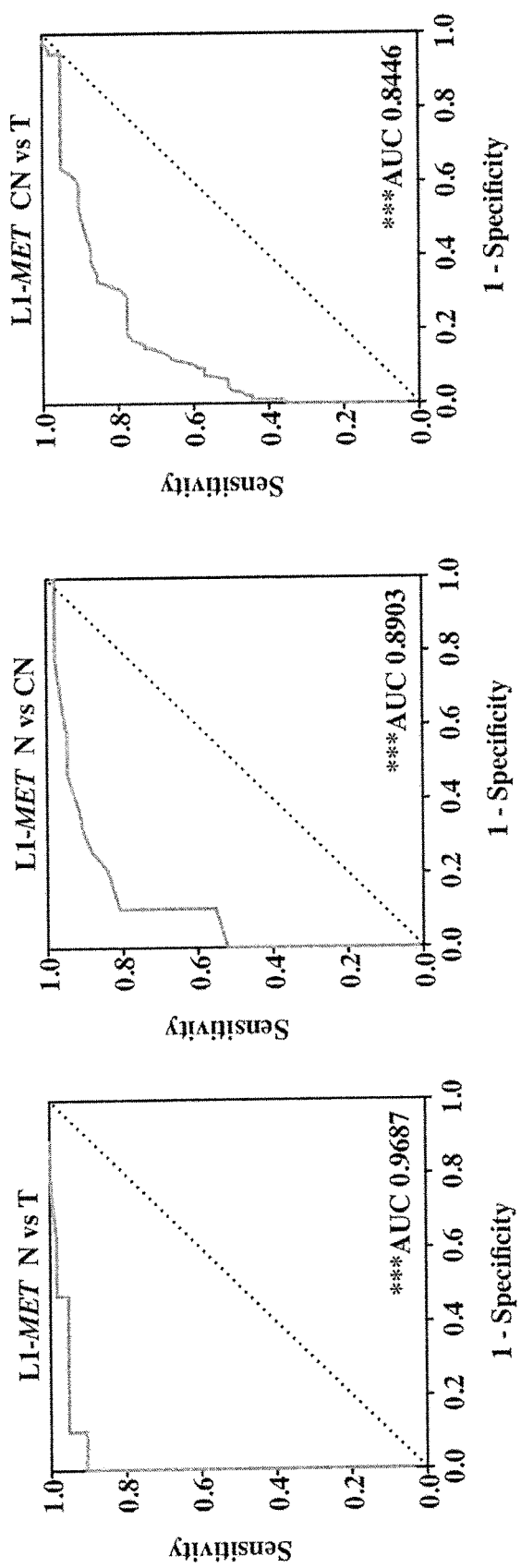
FIG. 21 shows the ROC curves for specific L1s. (A) ROC curves using L1-MET methylation distinguish between normal bladder tissue (N) and corresponding normal bladder tissues (CN), N and bladder tumors (T), and CN and T. (B) ROC curves using L1-ACVRIC methylation, and (C) ROC curves using L1-RAB3IP methylation. *** represents p<0.00I and * represents p<0.05. Found at: doi:10.1371/journal.pgen.1000917.s008 (0.65 MB TIF)
Figure 21B:
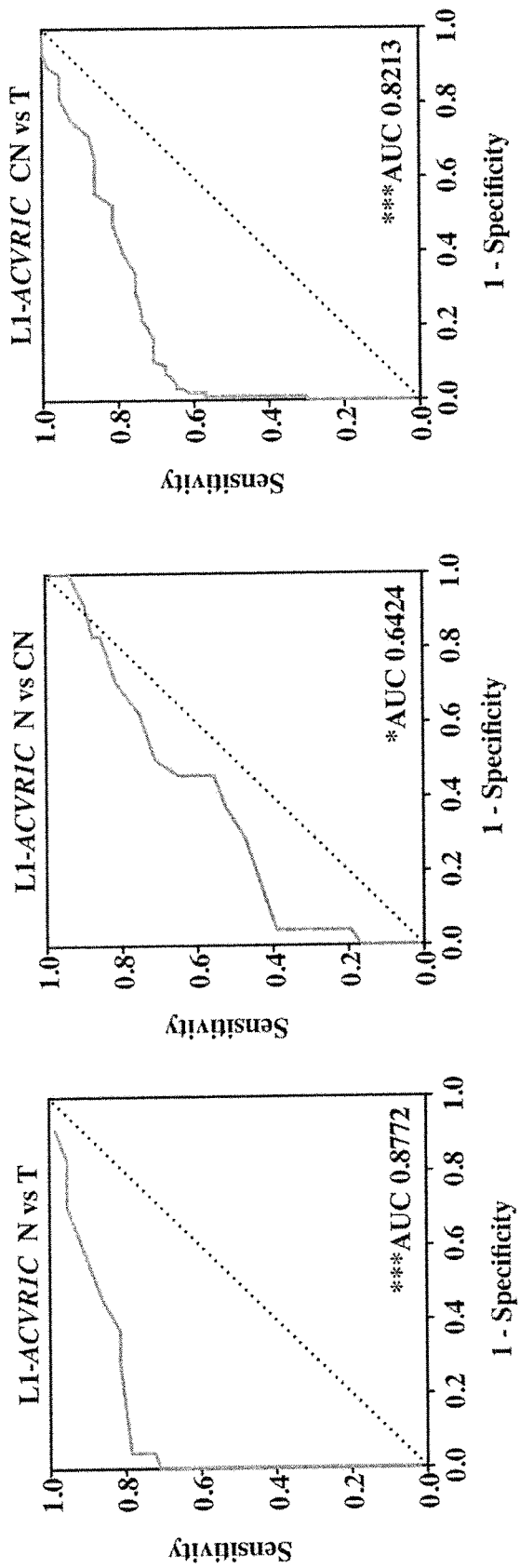
Figure 21C:
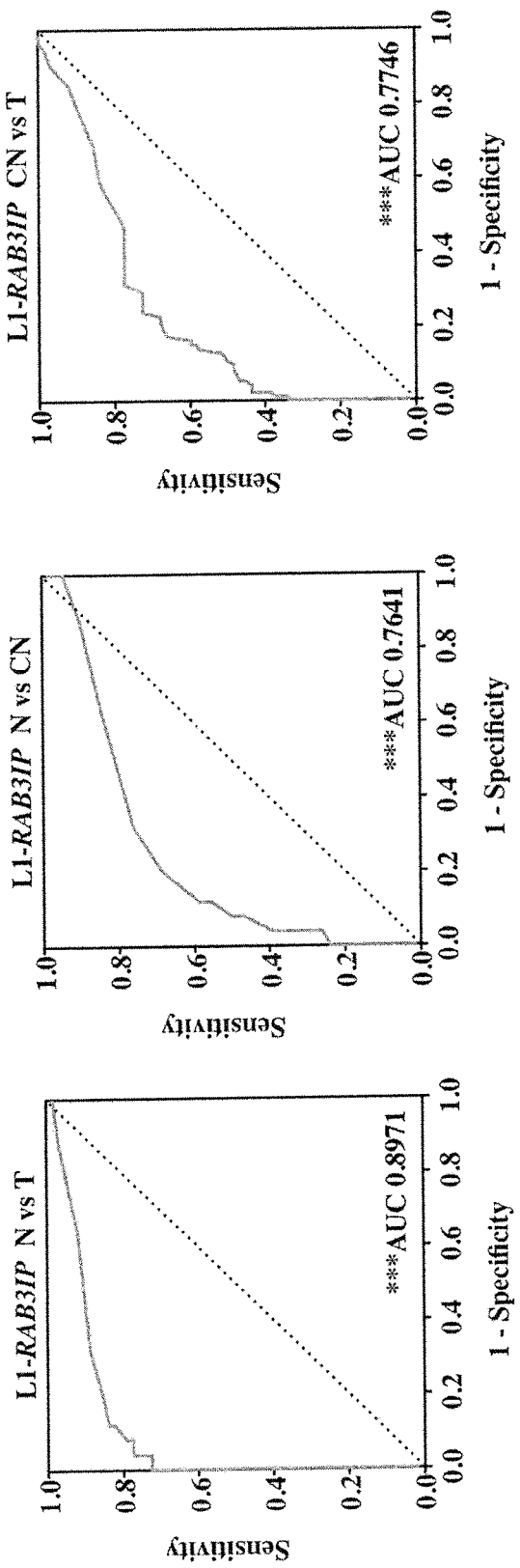

Surprisingly, we also found hypomethylation and associated alternate expression of L1-MET in the corresponding histologically normal tissues from tumor-bearing bladders taken at least 5 cm away from the tumor (p<0.0001) (FIGS. 11A&B). Hypomethylation and expression of L1-MET was more prevalent in the corresponding normal tissues than L1-ACVR1c, L1-RAB3IP (FIG. 20) [35]. Therefore, hypomethylation of L1-MET and activation of alternate transcripts of MET occurs not only during tumorigenesis but also in premalignant tissue. Receiver operating characteristic (ROC) curves for L1-MET revealed an extraordinary degree of both sensitivity and specificity for detecting bladder tumors (AUC of 0.97) and premalignant tissue (AUCs of 0.89) (FIG. 21). Since aberrant methylation in bladder tumors can be detected in urine sediments [36] and we are able to detect hypomethylation of L1-MET in urine sediments of bladder cancer patients (FIG. 22), a noninvasive urine test has the potential to be developed into an assay for tumor detection and prediction of high-risk patients.

As expected, the expression of the host gene MET was not correlated with hypomethylation of the L1-MET promoter, since the expression of MET is regulated by its endogenous promoter and not by the specific L1 promoter (FIGS. 11A&C). It has previously been shown that overexpression of MET is correlated with global L1 hypomethylation in chronic myeloid leukemia (CML) [14]. The biological mechanism behind this correlation is unclear, as MET is expressed from an entirely different promoter than L1-MET and we have shown that global L1 methylation does not correlate with specific L1 methylation. Further, we did not find overexpression of MET in bladder tumors, suggesting that it may be L1-MET that is overexpressed instead since many primers used to detect expression can amplify both products.

Figure 12A:
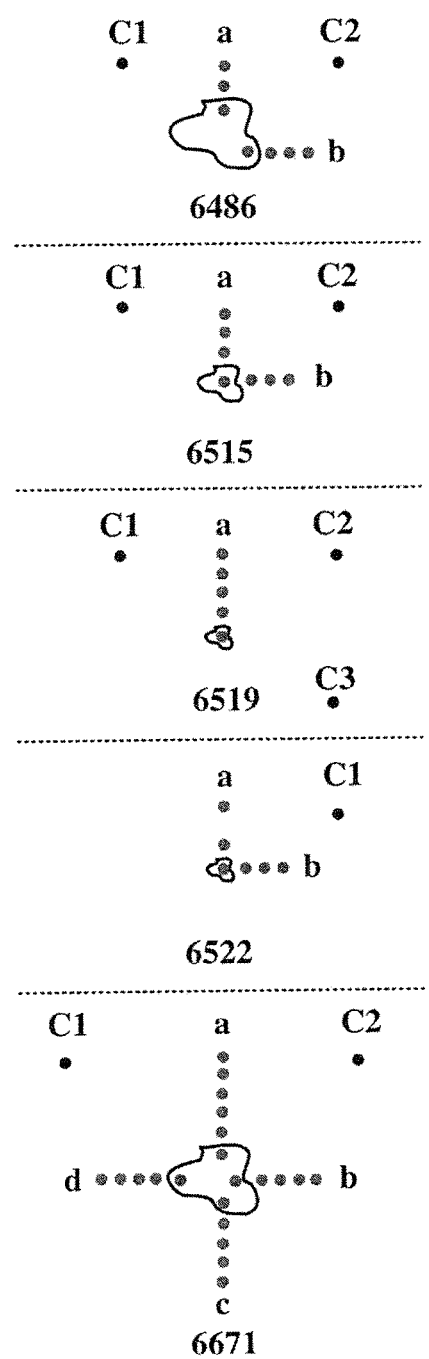
FIG. 12 shows the methylation of L1-MET across the bladder. A. Tissue samples were taken from five patients of their tumors (red, T) and at increasing distances from the tumor (0.5 to 2 cm) in the surrounding normal-appearing tissue in multiple directions (light blue, a to d). Additionally, distant normal-appearing samples were taken at least 5 cm from the tumor (dark blue, C). B. Methylation at L1-MET and C. global L1 was measured by pyrosequencing. The green line represents the mean methylation of normal samples from cancer-free patients. While there are no error bars for the clinical sample analysis due to the extremely limited amount of sample DNA, the results show a consistent trend. D. Bisulfite sequencing of L1-MET was performed on samples from two bladder cancer-free patients (#4987 and #5240) and one bladder cancer patient (#6519). White circles represent unmethylated CpGs and black circles represent methylated CpGs.
Figure 12B:
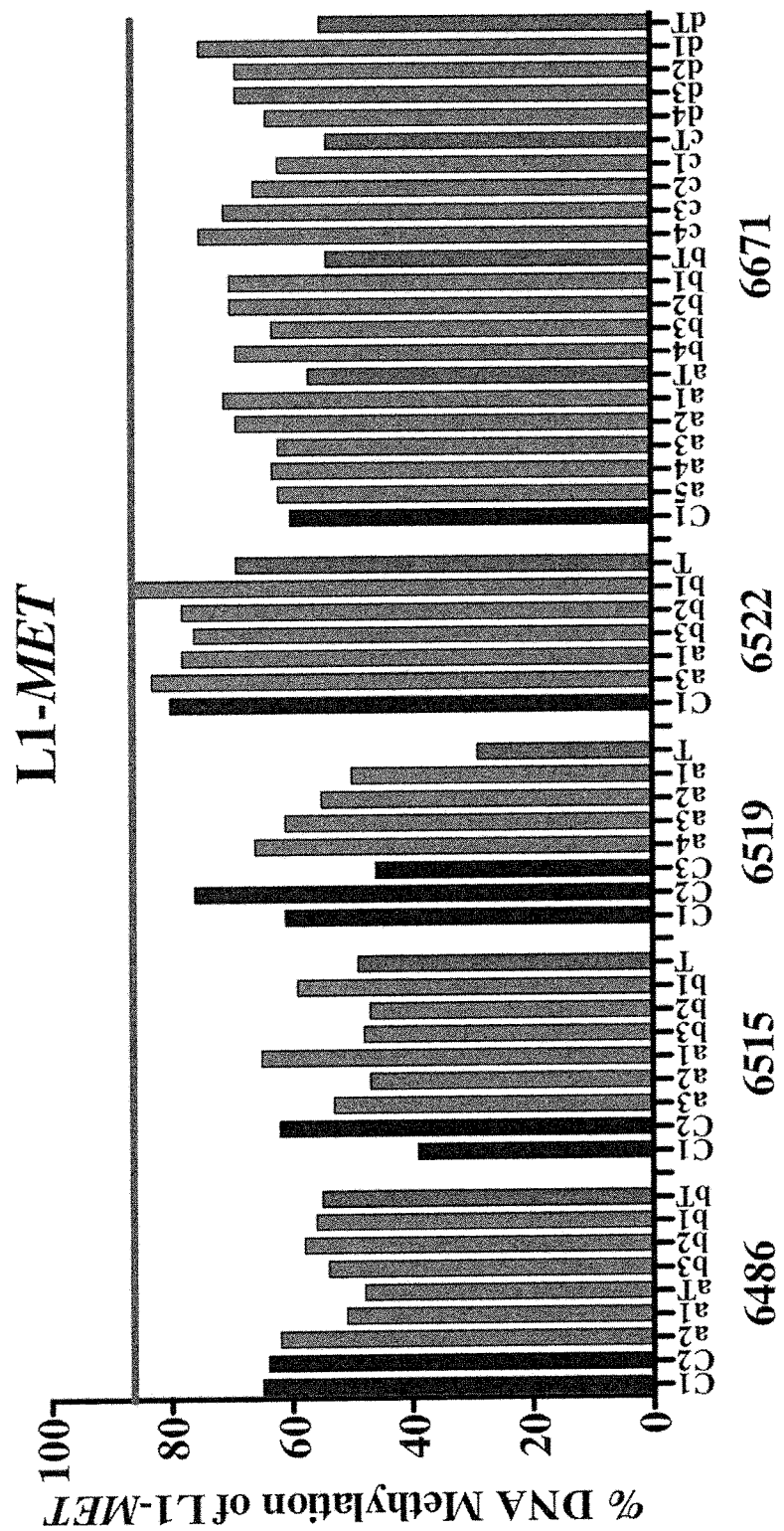
Figure 12C:
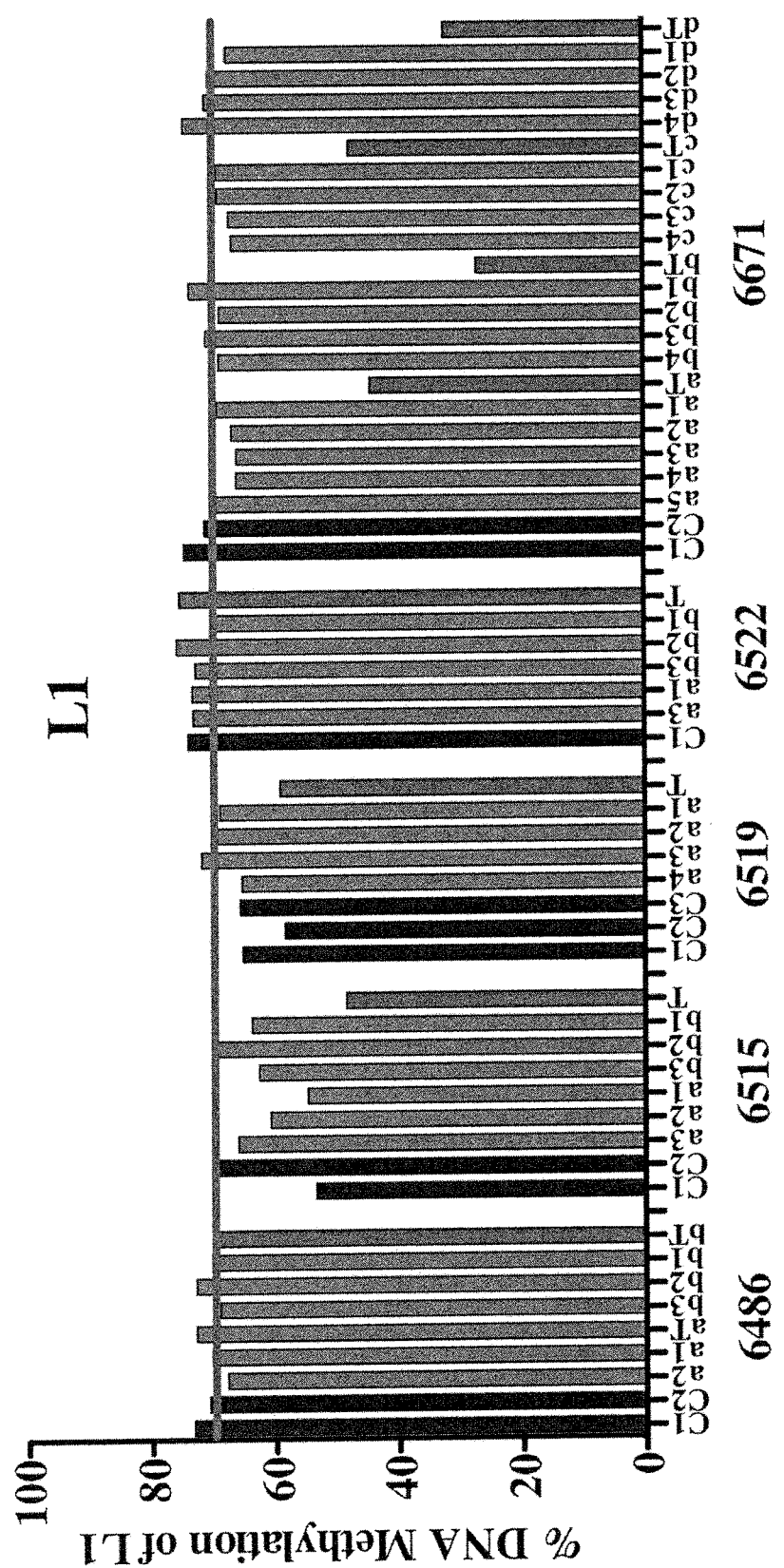
Figure 12D:
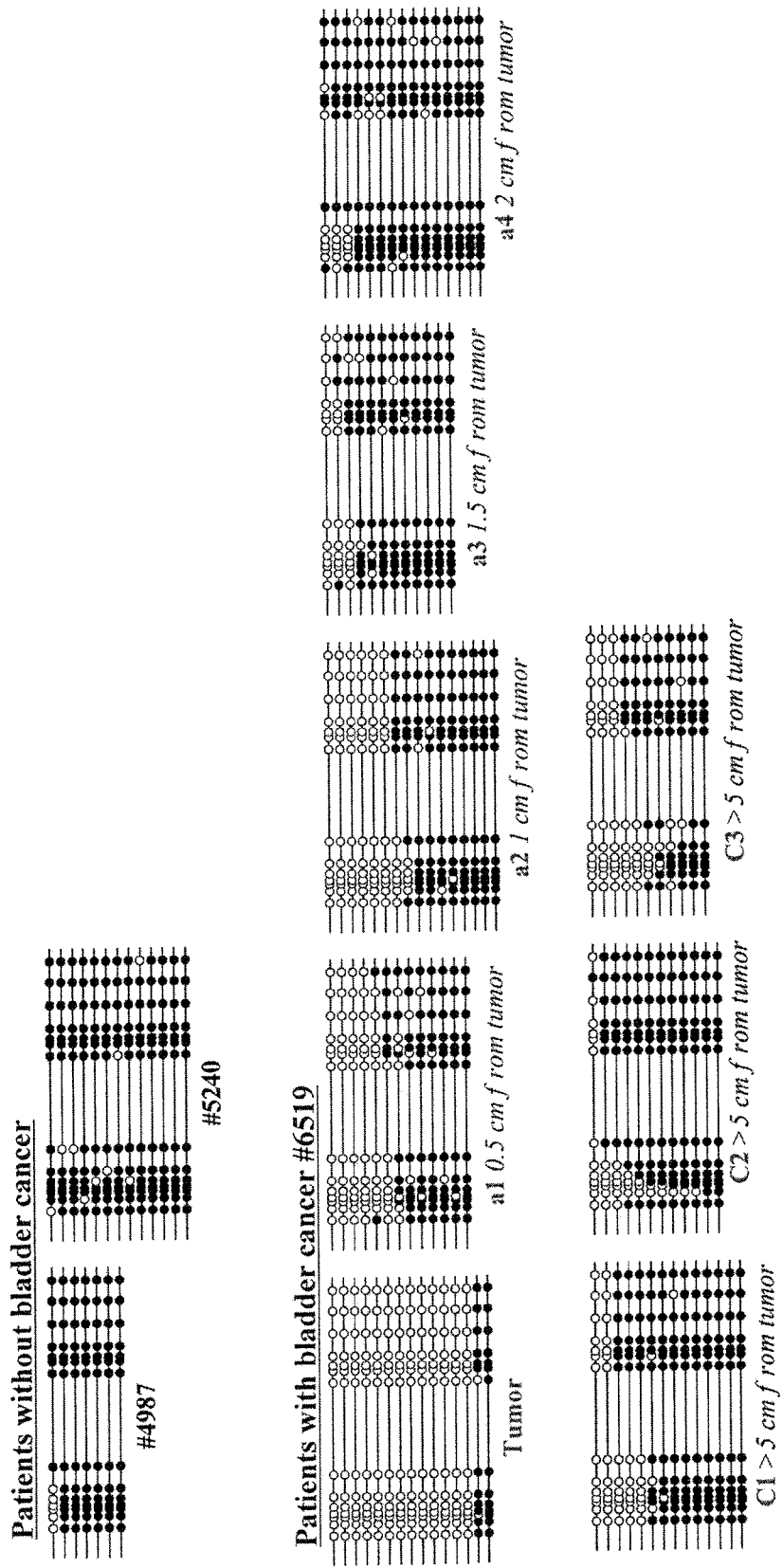
Figure 24A:
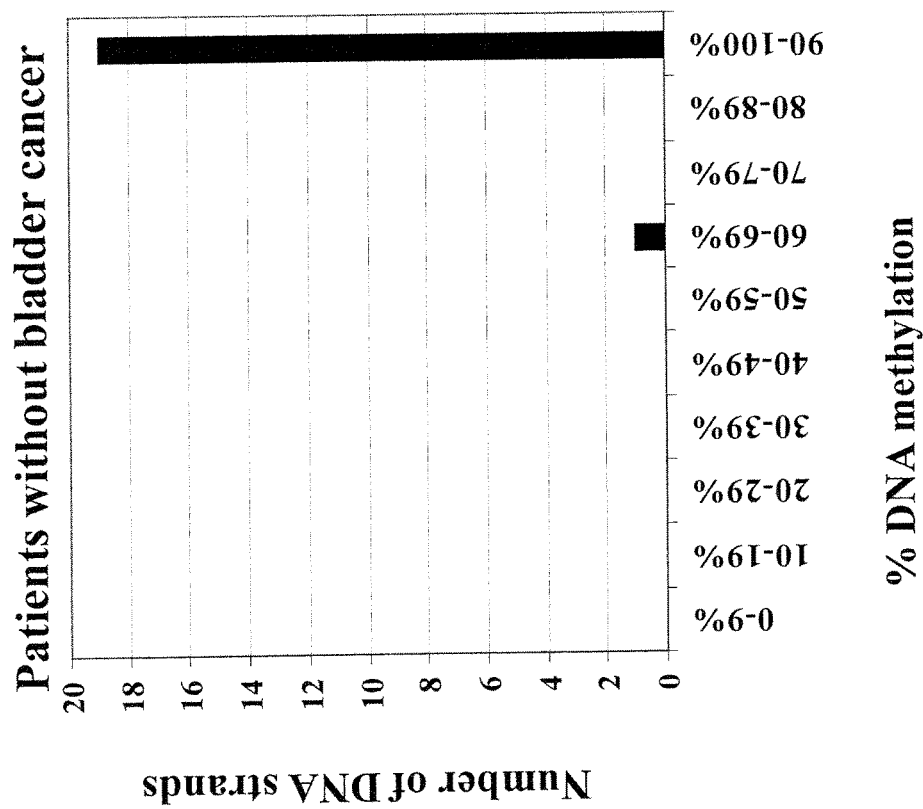
FIG. 24 shows the bisulfite sequencing of L1-MET. Biphasic distribution of L1-MET methylation status in corresponding tissue from a patient with bladder cancer is revealed by plotting the number of DNA strands by the percent of CpG sites methylated. Found at: doi:10.1371/journal.pgen. 1000917.s011(0.18 MB TIF)
Figure 24B:
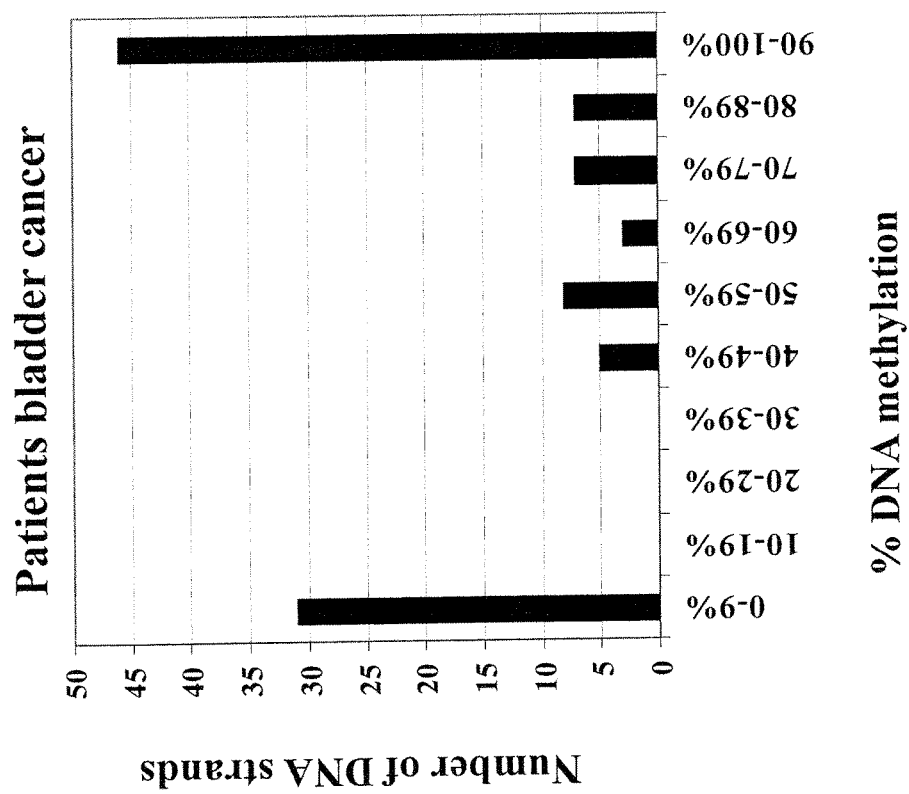

Hypomethylation and expression of L1-MET occurs across the urothelium of tumor-bearing bladders. Since we observed hypomethylation at L1-MET in bladder tissues taken at least 5 cm from tumors we collected histologically normal tissue samples from five tumor-bearing bladders taken at various distances and directions from the tumors to determine whether distance has any effect on the level of hypomethylation (FIG. 12A). When compared to the average level of methylation in normal tissues from cancer-free bladders, L1-MET was dramatically hypomethylated in normal-appearing tissues across each of the tumor-bearing bladders independent of the distance from the site of the tumor (FIG. 12B). However the normal-appearing tissues were not significantly hypomethylated at L1-ACVR1c, L1-RAB3IP, and global L1 (FIG. 23, & FIG. 12C). Bisulfite sequencing of L1-MET in the urothelium of patients without bladder cancer revealed only fully methylated strands while in a patient with bladder cancer fully unmethylated strands were present in the tumor and the corresponding normal urothelial tissue independent of the distance from the tumor (FIG. 12D & FIG. 24). A plot of the distribution of DNA strands versus the percent of methylated sites reveals a biphasic distribution in the patient with bladder cancer, with the majority of strands either fully methylated or fully unmethylated (FIG. 24). Our in vitro results (FIGS. 8&9) suggest that these fully unmethylated strands found in tumor-bearing bladders have undergone chromatin remodeling involving a switch from a tetranucleosome to a dinucleosome structure and are transcriptionally active. To our knowledge this is the first alteration, either epigenetic or genetic, that has been found across an entire tumor-bearing organ.

Materials and Methods

Cell Lines. The non-tumorigenic human urothelial cell lines UROtsa and NK2426 and the normal fibroblast cell line LD419 have been described previously [21, 22, 36]. Human bladder carcinoma cell lines were obtained commercially (T24, J82, HT1376, SCaBER, UM-UC-3, TCCSUP, and RT4; American Type Culture Collection, Manassas, Va.) or derived in our laboratory (prefix LD). Cell culture, DNA and RNA purification were performed as previously described [36]. RNA was reverse-transcribed as previously described [36]. 5'-Rapid Amplification of cDNA Ends (RACE) to determine the 5' end of the primary transcript of L1-MET was performed using the RLM-RACE kit (Ambion) according to the manufacturer's instruction. See Table 1 for primer sequences.

Tissue Collection. Tumor tissue samples were collected from the patients undergoing cystectomy or TURBT for bladder cancer. Normal bladder epithelium was obtained from 12 patients undergoing radical prostatectomy for prostate cancer (aged from 50 to 80) and 7 autopsy patients aged from 34 to 82, 5 of which were from non-cancer related deaths and 2 from deaths due to cancers other than bladder). All of these collections took place at Norris Cancer Hospital in IRB-approved protocols with patients' consent. Hematoxylin and eosin (H&E) sections marked with the location of the adjacent urothelium or tumor were used to guide in microdissection. DNA was bisulfite treated as previously described [44]. RNA extraction was done using a RNAeasy Micro Kit (Qiagen, Crawley, UK).

Figure 25A:
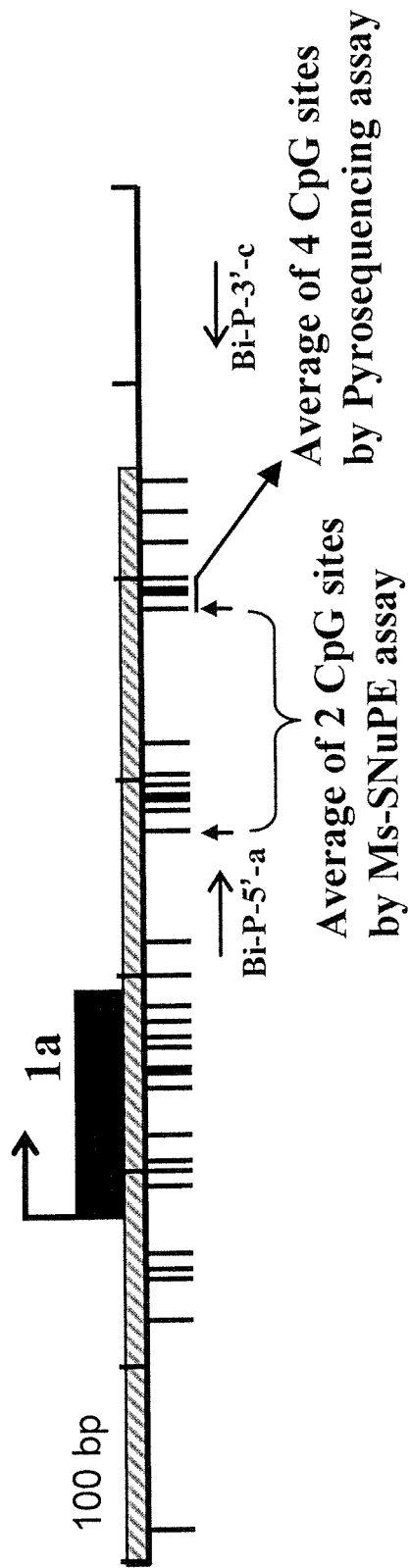
FIG. 25 shows that Ms-SNuPE and pyrosequencing yield similar methylation results. While both Ms-SNuPE and Pyrosequencing are quantitative assays, Pyrosequencing is much more high throughput. Therefore, we developed a Pyrosequenciag assay for the rest studies. (A) We measured 4 CpG sites by Pyrosequencing assay in contrast with the CpG sites by Ms-SNuPE. (B) We randomly chose 66 samples previously analyzed by Ms-SNuPE to perform Pyrosequencing on and the results are very similar from both assays (R=0.91). Found at: doi: 10.1371/journal.pgen. 1000917.s012 (0.42 MB TIE).
Figure 25B:
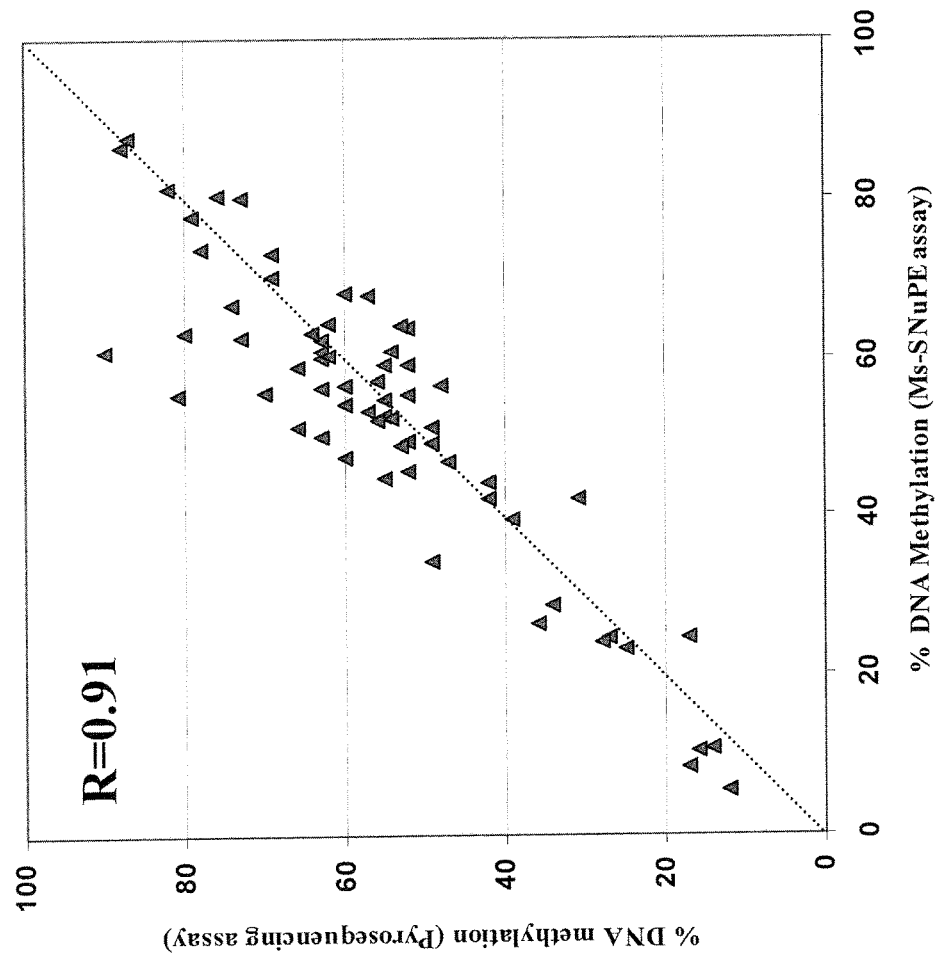
Figure 26:
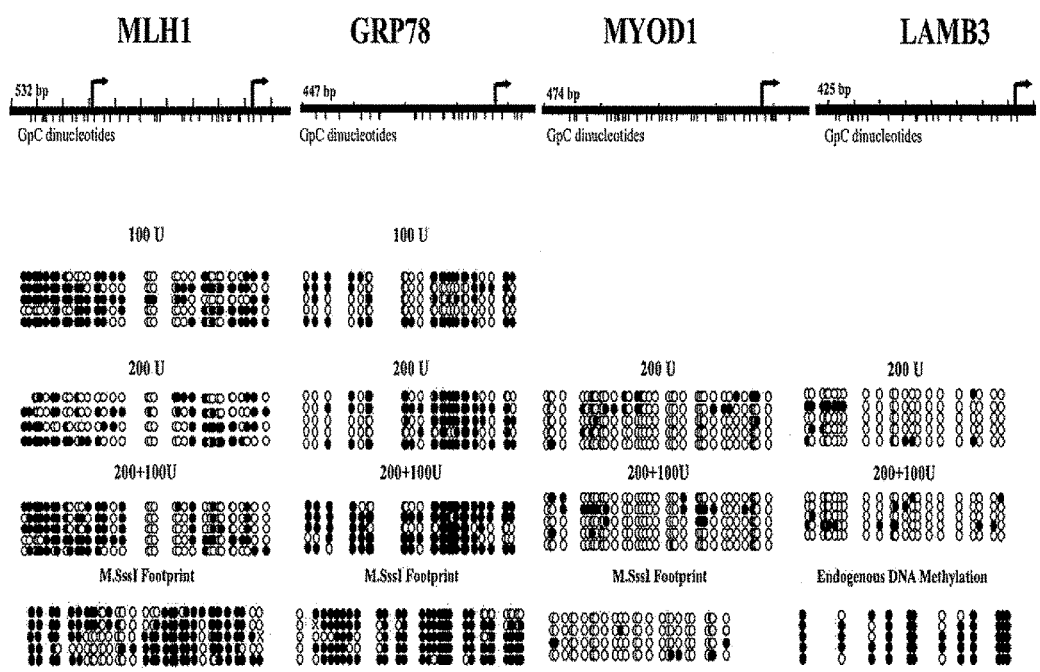
FIG. 26 shows that the methods of the present invention can accurately footprint open chromatin structures, without generating aberrant accessibility in occupied and CpG methylated promoters. I treated nuclei from human fibroblasts with different amounts of M.CviPI. Both GRP78 and MLH1 are expressed (and thus should have a nucleosome after the TSS and a nucleosome depleted region (NDR) before TSS). Accurate footprinting of MLH1 was obtained using 100 U of M.CviPI, however accurate footprinting of the NDR of GRP78 required the 200+100 M.CviPI condition. The 200+100 condition also accurately footprinted the MLH1 promoter. MYOD1 and LAMB3 are not expressed in human fibroblasts and are occupied by nucleosomes. The 200+100 condition did not result in aberrant accessibility at these promoters. Combining these results shows that 200+100 Units of enzyme can accurately footprint accessible promoters without leading to aberrant GpC methylation of inaccessible promoters. Black and white circles represent methylated and unmethylated sites, respectively. M.SssI footprint is shown as a positive control for GRP78, MLH1 and MYOD1 and endogenous methylation is shown for LAMB3.

Quantitation of DNA Methylation. Methylation-sensitive single nucleotide primer extention (MS-SNuPE) was performed as previously described [44]. See Table 1 for primer sequences. In order to allow for a higher throughput in methylation analysis pyrosequencing was also performed as described previously [45]. Testing both methods on the same set of 66 samples yielded a correlation in the methylation levels of R=0.91 (FIG. 25). For pyrosequencing, PCR was performed on bisulfite converted DNA using a biotin-labeled 3' primer to enable purification and denaturation of the product by Streptavidin Sepharose beads and was followed by annealing of a sequencing primer to the single-stranded PCR product. Pyrosequencing was performed using the PSQ HS96 Pyrosequencing System and the degree of methylation was expressed for each DNA locus as percentage methylated cytosines over the sum of methylated and unmethylated cytosines. See Table 1 for primer sequences. To analyze the methylation status of individual DNA molecules, we cloned bisulfite PCR fragments into the pCR2.1 vector using the TOPO-TA cloning kit (Invitrogen, Carlsbad, Calif.). Individual colonies were screened for the insert and the region of interest was sequenced using M13 primers. See Table 1 for primer sequences.

Quantitative RT-PCR. Expression was determined by quantitative RT-PCR as described previously [27]. See Table 1 for primer sequences.

Luciferase assay. The L1-MET and L1 promoters were cloned into the pCpGL luciferase vector [24]. The portion of the L1-MET promoter cloned was 555 bp, with 535 bp within the L1 and 20 bp within the MET gene (ch7: 116364010-564). These experiments were performed as described previously [24].

Chromatin immunoprecipitation. ChIP was performed as described previously [27]. Briefly, chromatin was isolated from cells and crosslinked with formaldehyde. The chromatin was then sonicated to less than 500 bp in length and immunoprecipitated with an antibody to the histone modification of interest. Enrichment was determined by RT-PCR of the pulled down DNA. See Table 1 for primer sequences.

Methylation-dependent single promoter analysis. M-SPA was performed as described previously [28]. Briefly, chromatin was isolated from 250,000 cells and treated for 15 minutes with 50 U of M. SssI. DNA was isolated, bisulfite converted, and PCR fragments were cloned for sequencing of individual molecules. In order to examine endogenously methylated promoters and increase the resolution of this method, chromatin from 250,000 cells was treated with the enzyme M. CviPI, which methylates GpC sites [29], for 15 minutes with 100 U.

MNase digestion and Southern blot. MNase digestion and sucrose density gradient centrifugation were performed as described previously [33]. See Table 1 for primer sequences for the LINE-1 promoter probe.

Statistical Analyses. Significant differences in methylation and expression levels in normal, corresponding normal, and tumor tissues were determined using a Mann-Whitney test.

Dr. Michael Rehli provided the pCpGL plasmid vector.

REFERENCES

1. Lipsanen V, Leinonen P, Alhonen L, Janne J (1988) Hypomethylation of ornithine decarboxylase gene and erb-A1 oncogene in human chronic lymphatic leukemia. Blood 72: 2042-2044.
2. Hanada M, Delia D, Aiello A, Stadtmauer E, Reed J C (1993) bcl-2 gene hypomethylation and high-level expression in B-cell chronic lymphocytic leukemia. Blood 82: 1820-1828.

3. Baylin S B, Herman J G, Graff J R, Vertino P M, Issa JP (1998) Alterations in DNA methylation: a fundamental aspect of neoplasia. Adv Cancer Res 72: 141-196.
4. Ovchinnikov I, Rubin A, Swergold G D (2002) Tracing the LINEs of human evolution. Proc Natl Acad Sci USA 99: 10522-10527.
5. Eden A, Gaudet F, Waghmare A, Jaenisch R (2003) Chromosomal instability and tumors promoted by DNA hypomethylation. Science 300: 455.
6. Waterland R A, Jirtle R L (2003) Transposable elements: targets for early nutritional effects on epigenetic gene regulation. Mol Cell Biol 23: 5293-5300.
7. Faulkner G J, Kimura Y, Daub C O, Wani S, Plessy C, et al. (2009) The regulated retrotransposon transcriptome of mammalian cells. Nat Genet. 41: 563-571.
8. Matlik K, Redik K, Speek M (2006) L1 antisense promoter drives tissue-specific transcription of human genes. J Biomed Biotechnol 2006: 71753.
9. Nigumann P, Redik K, Matlik K, Speek M (2002) Many human genes are transcribed from the antisense promoter of L1 retrotransposon. Genomics 79: 628-634.
10. Speek M (2001) Antisense promoter of human L1 retrotransposon drives transcription of adjacent cellular genes. Mol Cell Biol 21: 1973-1985.
11. Jones P A, Baylin SB (2002) The fundamental role of epigenetic events in cancer. Nat Rev Genet. 3: 415-428.
12. Zilberman D, Coleman-Derr D, Ballinger T, Henikoff S (2008) Histone H2A.Z and DNA methylation are mutually antagonistic chromatin marks. Nature 456: 125-129.
13. Chalitchagorn K, Shuangshoti S, Hourpai N, Kongruttanachok N, Tangkijvanich P, et al. (2004) Distinctive pattern of LINE-1 methylation level in normal tissues and the association with carcinogenesis. Oncogene 23: 8841-8846.
14. Roman-Gomez J, Jimenez-Velasco A, Agirre X, Cervantes F, Sanchez J, et al. (2005) Promoter hypomethylation of the LINE-1 retrotransposable elements activates sense/antisense transcription and marks the progression of chronic myeloid leukemia. Oncogene 24: 7213-7223.
15. Phokaew C, Kowudtitham S, Subbalekha K, Shuangshoti S, Mutirangura A (2008) LINE-1 methylation patterns of different loci in normal and cancerous cells. Nucleic Acids Res 36: 5704-5712.
16. Natali P G, Prat M, Nicotra M R, Bigotti A, Olivero M, et al. (1996) Overexpression of the met/HGF receptor in renal cell carcinomas. Int J Cancer 69: 212-217.
17. Joseph A, Weiss G H, Jin L, Fuchs A, Chowdhury S, et al. (1995) Expression of scatter factor in human bladder carcinoma. J Natl Cancer Inst 87: 372-377.
18. Li B, Kanamaru H, Noriki S, Fukuda M, Okada K (1998) Differential expression of hepatocyte growth factor in papillary and nodular tumors of the bladder. Int J Urol 5: 436-440.
19. Wallenius V, Hisaoka M, Helou K, Levan G, Mandahl N, et al. (2000) Overexpression of the hepatocyte growth factor (HGF) receptor (Met) and presence of a truncated and activated intracellular HGF receptor fragment in locally aggressive/malignant human musculoskeletal tumors. Am J Pathol 156: 821-829.
20. Birchmeier C, Birchmeier W, Gherardi E, Vande Woude G F (2003) Met, metastasis, motility and more. Nat Rev Mol Cell Biol 4: 915-925.
21. Rossi M R, Masters J R, Park S, Todd J H, Garrett S H, et al. (2001) The immortalized UROtsa cell line as a potential cell culture model of human urothelium. Environ Health Perspect 109: 801-808.
22. Chapman E J, Hurst C D, Pitt E, Chambers P, Aveyard J S, et al. (2006) Expression of hTERT immortalises normal human urothelial cells without inactivation of the p16/Rb pathway. Oncogene 25: 5037-5045.
23. Kim B C, van Gelder H, Kim T A, Lee H J, Baik K G, et al. (2004) Activin receptor-like kinase-7 induces apoptosis through activation of MAPKs in a Smad3-dependent mechanism in hepatoma cells. J Biol Chem 279: 28458-28465.
24. Klug M, Rehli M (2006) Functional analysis of promoter CpG methylation using a CpG-free luciferase reporter vector. Epigenetics 1: 127-130.
25. Martens J H, O'Sullivan R J, Braunschweig U, Opravil S, Radolf M, et al. (2005) The profile of repeat-associated histone lysine methylation states in the mouse epigenome. Embo J 24: 800-812.
26. Liang G, Lin J C, Wei V, Yoo C, Cheng J C, et al. (2004) Distinct localization of histone 113 acetylation and H3-K4 methylation to the transcription start sites in the human genome. Proc Natl Acad Sci USA 101: 7357-7362.
27. Lin J C, Jeong S, Liang G, Takai D, Fatemi M, et al. (2007) Role of nucleosomal occupancy in the epigenetic silencing of the MLH1 CpG island. Cancer Cell 12: 432-444.
28. Fatemi M, Pao M M, Jeong S, Gal-Yam E N, Egger G, et al. (2005) Footprinting of mammalian promoters: use of a CpG DNA methyltransferase revealing nucleosome positions at a single molecule level. Nucleic Acids Res 33: e176.
29. Xu M, Kladde M P, Van Etten J L, Simpson R T (1998) Cloning, characterization and expression of the gene coding for a cytosine-5-DNA methyltransferase recognizing GpC. Nucleic Acids Res 26: 3961-3966.
30. Jiang C, Pugh BF (2009) Nucleosome positioning and gene regulation: advances through genomics. Nat Rev Genet. 10: 161-172.
31. Rhee I, Bachman K E, Park B H, Jair K W, Yen R W, et al. (2002) DNMT1 and DNMT3b cooperate to silence genes in human cancer cells. Nature 416: 552-556.
32. Egger G, Jeong 5, Escobar S G, Cortez C C, Li T W, et al. (2006) Identification of DNMT1 (DNA methyltransferase 1) hypomorphs in somatic knockouts suggests an essential role for DNMT1 in cell survival. Proc Natl Acad Sci USA 103: 14080-14085.
33. Jeong S, Liang G, Sharma S, Lin J C, Choi S H, et al. (2009) Selective Anchoring of DNA Methyltransferases 3A/3B to Nucleosomes Containing Methylated DNA. Mol Cell Biol.
34. Florl A R, Lower R, Schmitz-Drager B J, Schulz W A (1999) DNA methylation and expression of LINE-1 and HERV-K provirus sequences in urothelial and renal cell carcinomas. Br J Cancer 80: 1312-1321.
35. Choi S H, Worswick S, Byun H M, Shear T, Soussa J C, et al. (2009) Changes in DNA methylation of tandem DNA repeats are different from interspersed repeats in cancer. Int J Cancer 125: 723-729.
36. Friedrich M G, Weisenberger D J, Cheng J C, Chandrasoma S, Siegmund K D, et al. (2004) Detection of methylated apoptosis-associated genes in urine sediments of bladder cancer patients. Clin Cancer Res 10: 7457-7465.
37. Schalch T, Duda S, Sargent D F, Richmond T J (2005) X-ray structure of a tetranucleosome and its implications for the chromatin fibre. Nature 436: 138-141.

38. Yan P S, Venkataramu C, Ibrahim A, Liu J C, Shen R Z, et al. (2006) Mapping geographic zones of cancer risk with epigenetic biomarkers in normal breast tissue. Clin Cancer Res 12: 6626-6636.
39. Eads C A, Lord R V, Kurumboor S K, Wickramasinghe K, Skinner M L, et al. (2000) Fields of aberrant CpG island hypermethylation in Barrett's esophagus and associated adenocarcinoma. Cancer Res 60: 5021-5026.
40. Shen L, Kondo Y, Rosner G L, Xiao L, Hernandez N S, et al. (2005) MGMT promoter methylation and field defect in sporadic colorectal cancer. J Natl Cancer Inst 97: 1330-1338.
41. Suter C M, Martin D I, Ward R L (2004) Hypomethylation of L1 retrotransposons in colorectal cancer and adjacent normal tissue. Int J Colorectal Dis 19: 95-101.
42. Jones T D, Wang M, Eble J N, MacLennan G T, Lopez-Beltran A, et al. (2005) Molecular evidence supporting field effect in urothelial carcinogenesis. Clin Cancer Res 11: 6512-6519.
43. Moore L E, Pfeiffer R M, Poscablo C, Real F X, Kogevinas M, et al. (2008) Genomic DNA hypomethylation as a biomarker for bladder cancer susceptibility in the Spanish Bladder Cancer Study: a case-control study. Lancet Oncol 9: 359-366.
44. Gonzalgo M L, Liang G (2007) Methylation-sensitive single-nucleotide primer extension (Ms-SNuPE) for quantitative measurement of DNA methylation. Nat Protoc 2: 1931-1936.
45. Bollati V, Baccarelli A, Hon L, Bonzini M, Fustinoni S, et al. (2007) Changes in DNA methylation patterns in subjects exposed to low-dose benzene. Cancer Res 67: 876-880.

Example IV

The Methods of the Present Invention can Accurately Footprint Open Chromatin Structures without Generating Aberrant Accessibility in Occupied and Methylated Sequences The methods and kits of the present invention can be used to identify distinct chromatin configurations associated with specific histone modifications and promoter types. We examined specific promoter classifications as determined by Hawkins et al (Hawkins, 2010). Consistent with their active status, H3K4me3 marked promoters are unmethylated, show a distinct Nucleosome Depleted Region (NDR) upstream of the Transcription Start Site (TSS) and at least four well-positioned nucleosomes downstream of the TSS (FIG. 3). In contrast H3K27me3 marked promoters are unmethylated but nucleosome occupied, as indicated by inaccessibility to M.CviPI. DNA methylated promoters are nucleosome occupied. We next investigated the chromatin configurations of CpG island and non-CpG island promoters (FIG. 3B,C). In general, CpG island promoters are unmethylated, show a distinct NDR upstream of the TSS and wellpositioned nucleosomes downstream of the TSS. Separating CpG island promoters into those that are methylated and unmethylated reveals that the CpG island promoter pattern is largely driven by unmethylated CpG island promoters (11,165 promoters) and the few CpG island promoters that are methylated (781 promoters) do not show an NDR. In general, non-CpG island promoters are endogenously methylated and nucleosome occupied. Separating non-CpG island promoters into those that are methylated and unmethylated reveals that unmethylated non-CpG island promoters also have an NDR upstream of the TSS and a nucleosome immediately downstream of the TSS while methylated non-CpG island promoters do not show an NDR. Methylated non-CpG island promoters show a relative decrease in endogenous methylation immediately upstream of the TSS which can also be seen in the overall pattern for non-CpG island promoters.

We next examined the correlation between chromatin configurations determined by GNOMe-seq and transcription level (Supplemental FIG. 1). We divided promoters into quartiles based on their expression level {Hawkins, 2010}. GNOMe-seq shows that promoters in the lowest bin (0-25%) are nucleosome occupied with intermediate DNA methylation levels, likely reflecting that inactive promoters can be silenced through DNA dependent and independent mechanisms. With increasing expression quartiles the NDR upstream of the promoter and the positioning of the nucleosomes after the TSS become more apparent. Interestingly, there is a relative increase in DNA methylation immediately upstream of the TSS in the 50% most expressed genes.

Figure 27:
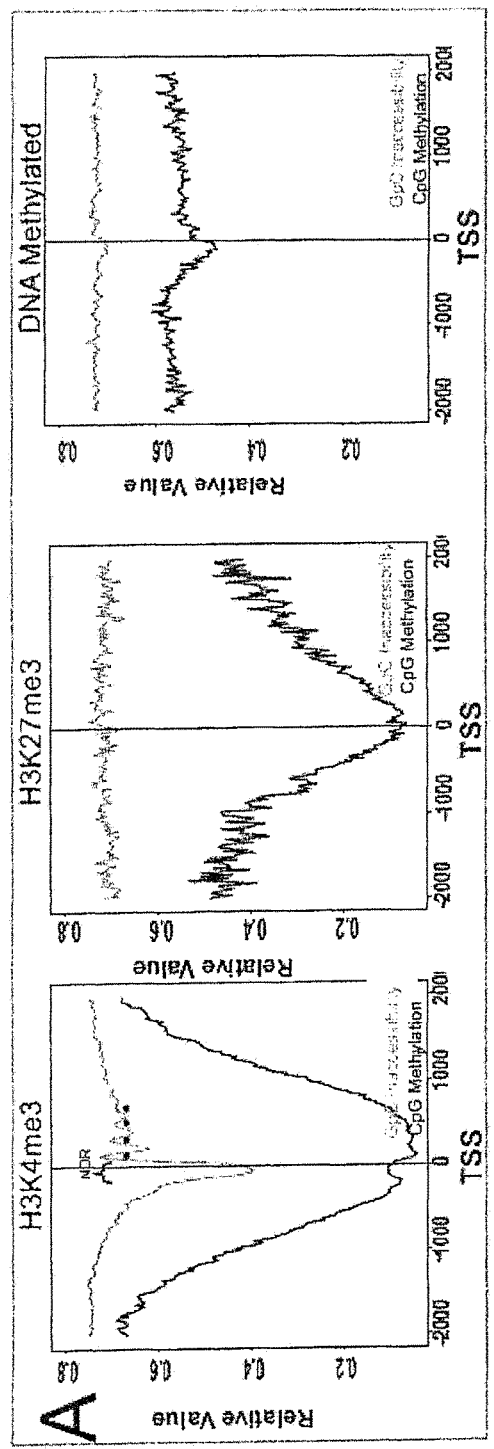
FIG. 27 shows that the method of the present invention are able to identify distinct chromatin configurations associated with specific histone modifications and promoter types. (A) GNOMe-seq demonstrates that H3K4me3 marked promoters are unmethylated and contain an NDR upstream and well positioned nucleosomes after the TSS. H3K27me3 marked promoters are unmethylated and nucleosome occupied as indicated by M.CviPI inaccessibility. Methylated promoters are nucleosome occupied. (B) CpG island promoters are characterized by a lack of CpG methylation, an upstream NDR and well positioned nucleosomes after the TSS. The majority of CpG island promoters are unmethylated (11,165) and display the same pattern, while methylated CpG island promoters (781) are nucleosome occupied and inaccessible to M.CviPI. (C) Non-CpG island promoters are generally characterized by CpG methylation and inaccessibility to M.CviPI, indicating nucleosome occupancy.
Figure 27:
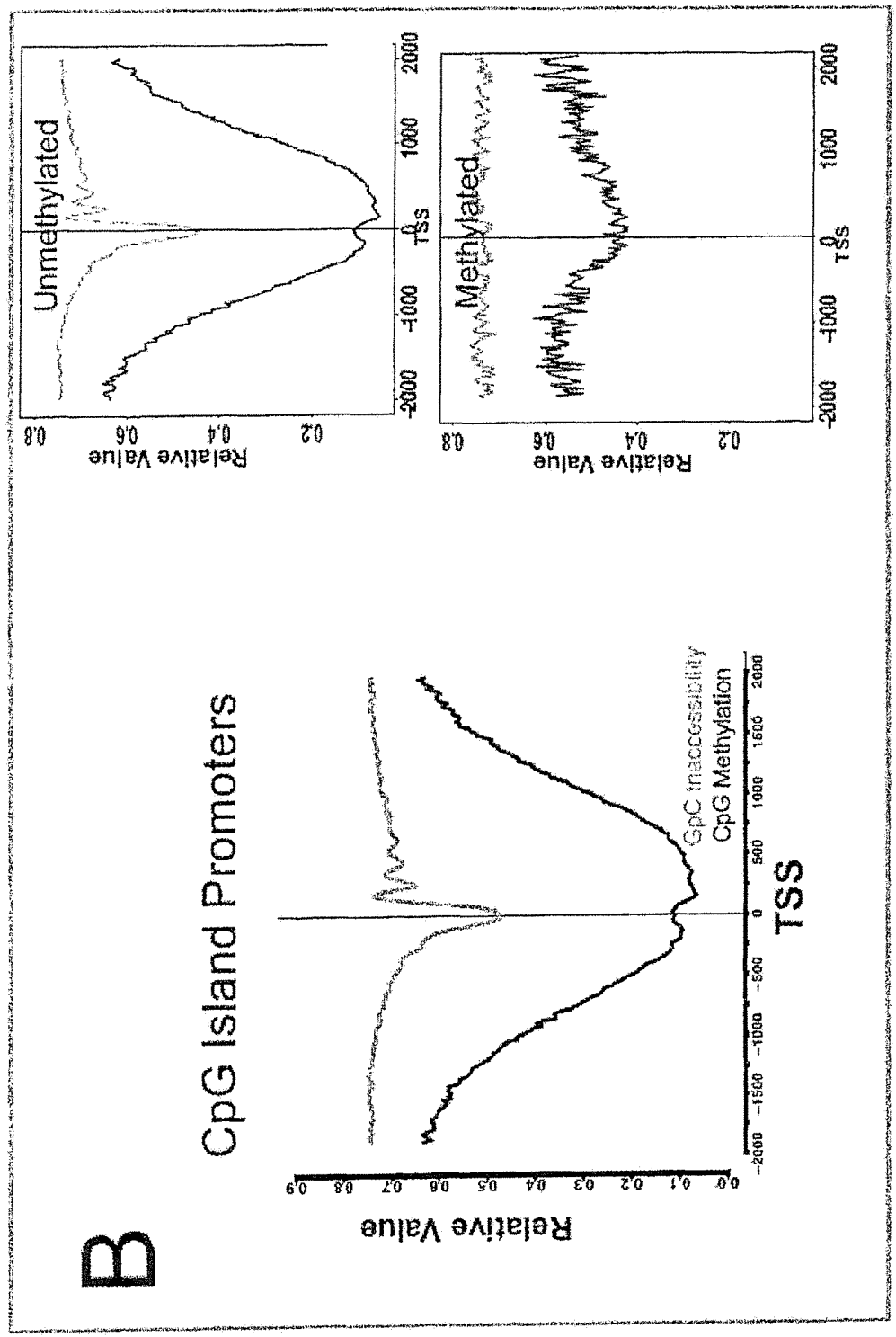
Figure 27:
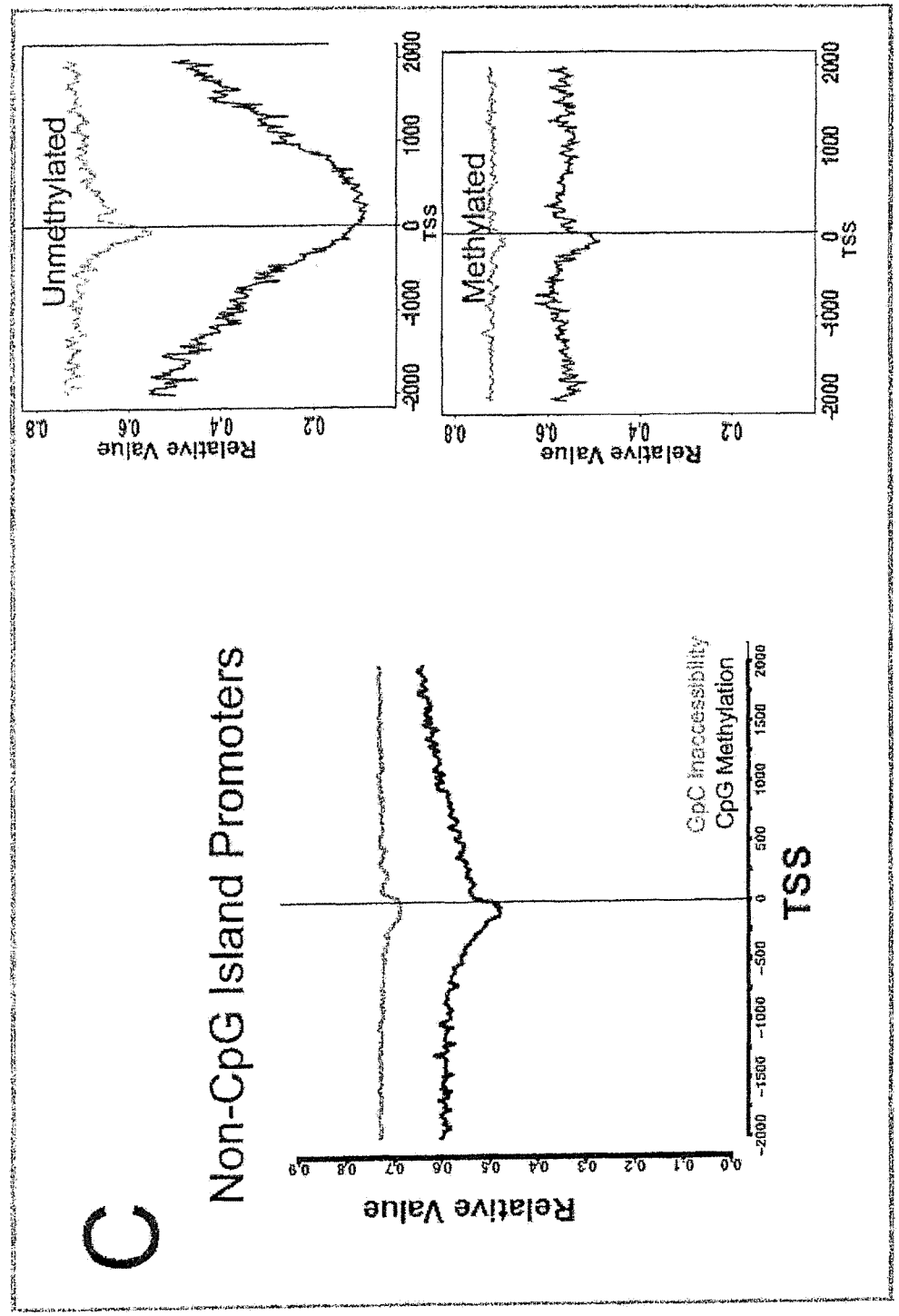

As shown in FIG. 27, the methods and kits of the present invention are able to reveal distinct chromatin configurations associated with specific histone modifications and promoter types. (A) GNOMe-seq demonstrates that H3K4me3 marked promoters are unmethylated and contain an NDR upstream and well positioned nucleosomes after the TSS. H3K27me3 marked promoters are unmethylated and nucleosome occupied as indicated by M.CviPI inaccessibility. Methylated promoters are nucleosome occupied. (B) CpG island promoters are characterized by a lack of CpG methylation, an upstream NDR and well positioned nucleosomes after the TSS. The majority of CpG island promoters are unmethylated (11,165) and display the same pattern, while methylated CpG island promoters (781) are nucleosome occupied and inaccessible to M.CviPI. (C) Non-CpG island promoters are generally characterized by CpG methylation and inaccessibility to M.CviPI, indicating nucleosome occupancy. The few unmethylated non-CpG island promoters (1397) are depleted of nucleosomes upstream of the TSS, while the majority of non-CpG island promoters (4668) are nucleosome occupied and inaccessible to M.CviPI. M.CviPI inaccessibility is plotted (1-GCH) in teal and CpG methylation (CGH) in black.

Figure 28:
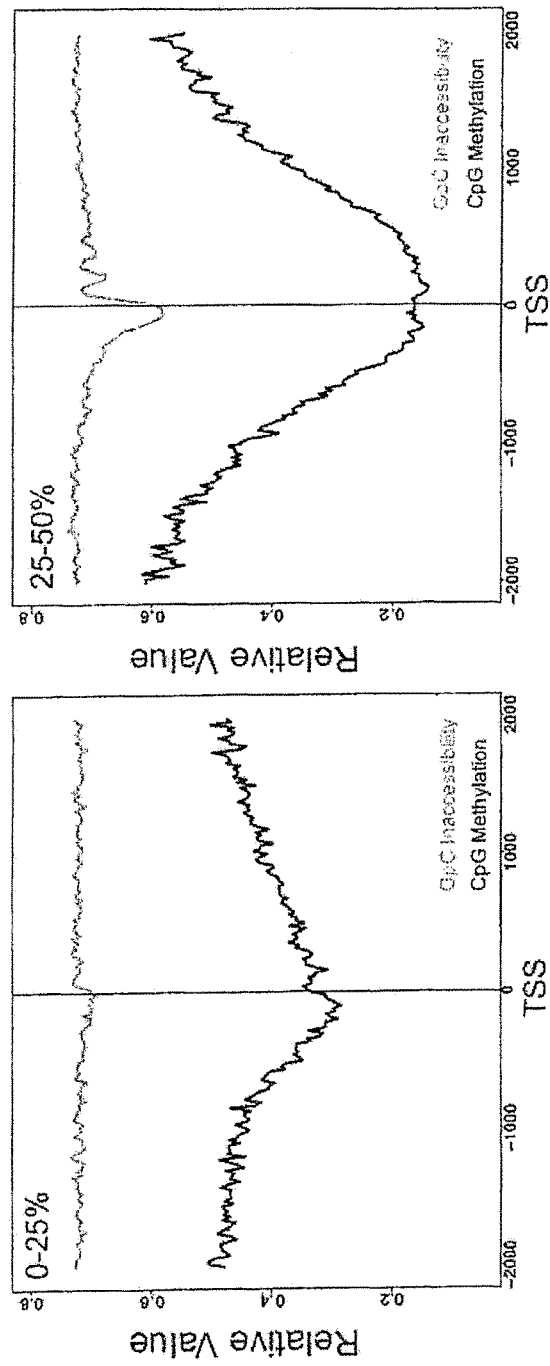
FIG. 28 shows that the methods of the present invention are able to identify differences in chromatin configurations based on gene expression level. Gene promoters were divided into quartiles based on transcription level and the corresponding M.CviPI inaccessibility (1-GCH, gray line) and DNA methylation (CGH, black line) is plotted.
Figure 28:
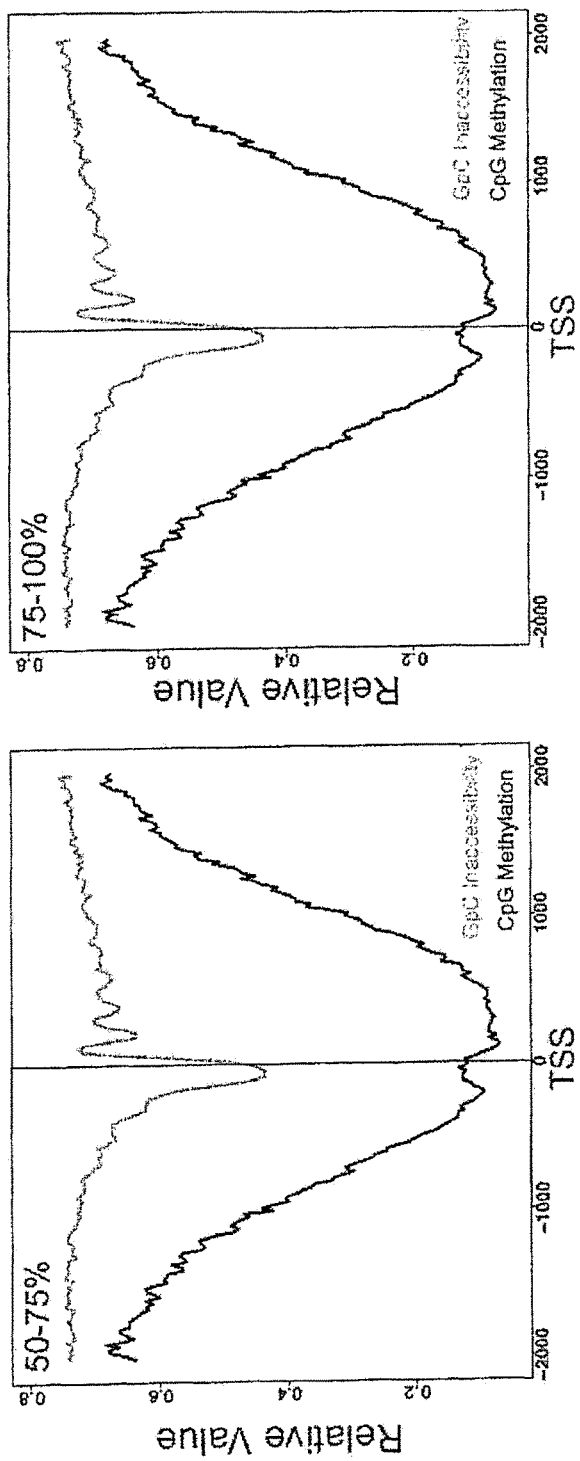
Figure 29:
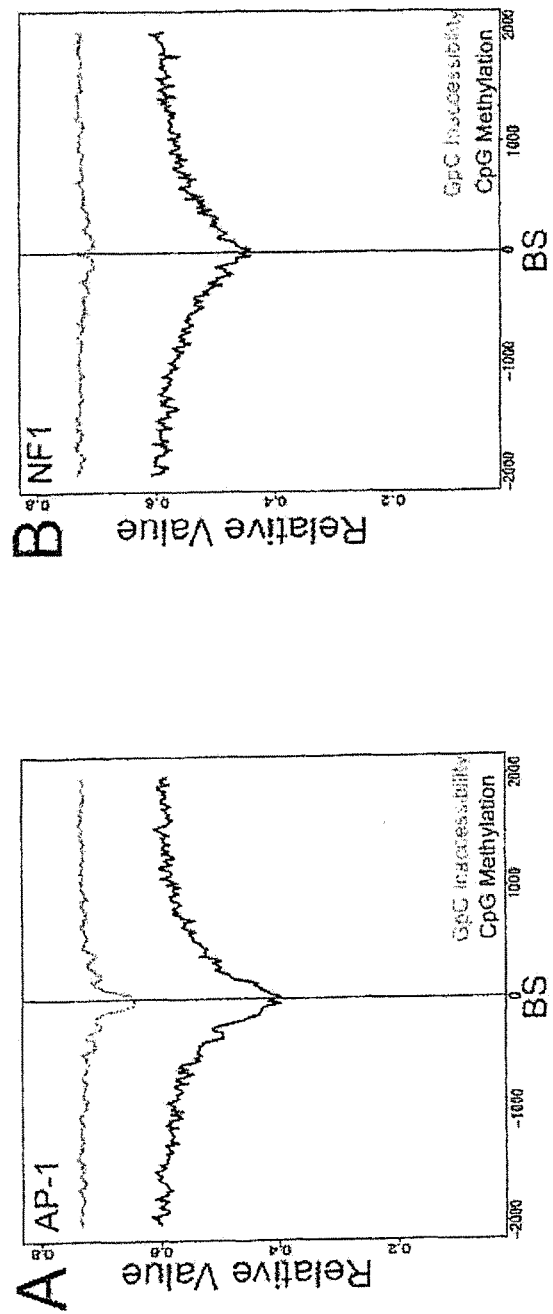
FIG. 29 shows that GNOMe-seq was also able to footprint nucleosomes surrounding transcription factor binding sites (FIG. 29A-D). (A-D) GNOME-seq displays different chromatin configurations surrounding various transcription factor binding sites. Reads were aligned to the center of transcription factor binding consensus sequences. Data is plotted as M. CviPI inaccessibility (1-GCH, gray line) and DNA methylation (CGH, black line)
Figure 29:
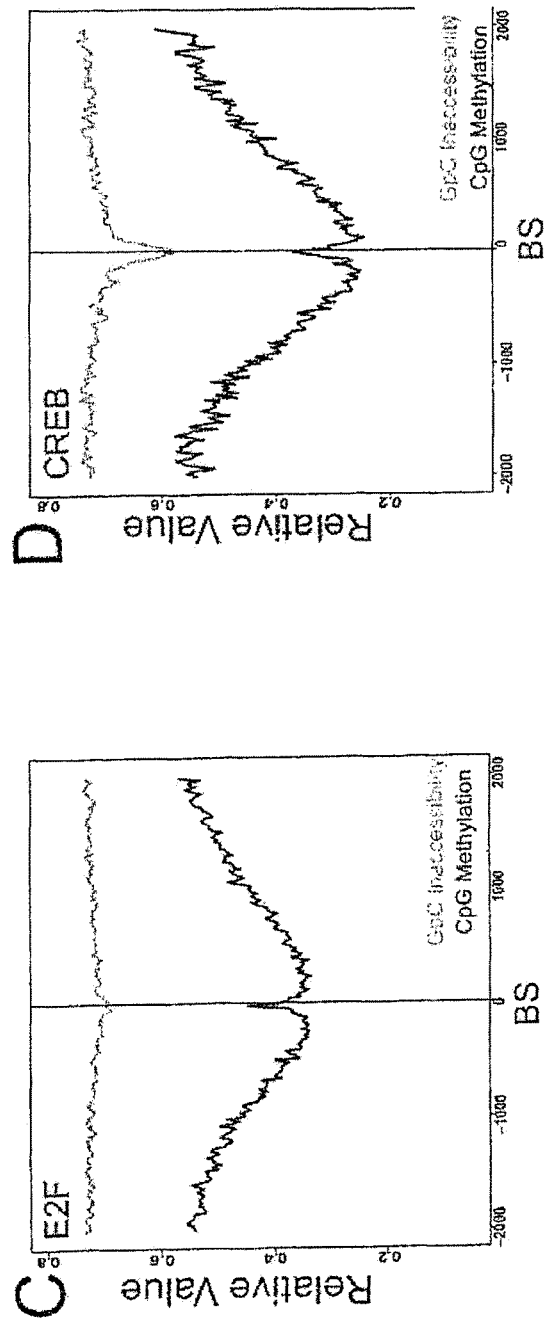

The methods and kits of the present invention are able to identify differences in chromatin configurations based on gene expression level as shown in FIG. 28. Gene promoters were divided into quartiles based on transcription level and the corresponding M.CviPI inaccessibility (1-GCH, teal line) and DNA methylation (CGH, black line) is plotted.

The methods and kits of the present invention are also able to footprint nucleosomes surrounding transcription factor binding sites. As shown in FIG. 29A-D, the methods and kits of the present invention are able to identify different chromatin configurations surrounding various transcription factor binding sites. Reads were aligned to the center of transcription factor binding consensus sequences. Data is plotted as M.CviPI inaccessibility (1-GCH, gray line) and DNA methylation (CGH, black line)

We found variable chromatin configurations surrounding specific transcription factor binding sites. (A) At AP-1 binding sites there is low levels of DNA methylation and nucleosome depletion, while at (B) NF1 binding sites there is also a dip in DNA methylation levels but the sites are nucleosome occupied. (B) At E2F binding sites there is a peak in methylation that corresponds to nucleosome occupancy. Interestingly, at CREB binding sites there is a peak in DNA methylation that corresponds to a dip in nucleosome occupancy.

All publications cited herein are expressly incorporated herein by reference in their entirety.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

SEQUENCE LISTING

<110> UNIVERSITY OF SOUTHERN CALIFORNIA
Kelly, Theresa K
Liang, Gangning
Jones, Peter A
<120> METHODS AND KITS FOR GENOME-WIDE METHYLATION OF GpC SITES AND GENOME-WIDE DETERMINATION OF CHROMATIN STRUCTURE
<130> 374634-000247
<140> U.S. Ser. No. 13/169,815
<141> 2011-06-27
<150> U.S. 61/358,767
<151> 2010-06-25
<160> 6
<170> PatentIn version 3.5
<210> 1
<211> 52
<212> DNA
<213> Artificial Sequence
<220>
<223> Synthetic oligonucleotide
<400> 1
gatagacagc tgctgaacca atgggaccaa gcttcacacc gagttcatcg et 52
<210> 2
<211> 52
<212> DNA
<213> Artificial Sequence
<220>
<223> Synthetic oligonucleotide
<400> 2
ctatctgtcg acgacttggt taccctggtt cgaagtgtgg ctcaagtagc ga 52
<210> 3
<211> 52
<212> DNA
<213> Artificial Sequence
<220>
<223> Synthetic oligonucleotide
<400> 3
gatagatagt tgttgaatta atgggattaa gttttatatc gagtttatcg tt 52
<210> 4
<211> 52
<212> DNA
<213> Artificial Sequence
<220>
<223> Synthetic oligonucleotide
<400> 4
ctatctatca acaacttaat taccctaatt caaaatatag ctcaaatagc aa 52
<210> 5
<211> 19
<212> DNA
<213> Artificial Sequence
<220>
<223> Synthetic oligonucleotide
<400> 5
gatagatagt tgttgaatt 19
<210> 6
<211> 123
<212> DNA
<213> Artificial Sequence
<220>
<223> Synthetic oligonucleotide
<400> 6
cagactgctg tgctagcaat cagcgggact ccgtgggcgt aggaccctcc gagccagcaa 60
gggaagcttt tggaagccac ccggtagagc tggaagagaa tttcgaaatc aattcgctca 120
acc 123

SEQUENCE LISTING

<160> NUMBER OF SEQ ID NOS: 6

<210> SEQ ID NO 1
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 1
gatagacagc tgctgaacca atgggaccaa gcttcacacc gagttcatcg ct            52

<210> SEQ ID NO 2
<211> LENGTH: 52
<212> TYPE: DNA
<213> ORGANISM: Artificial Sequence

```
<220> FEATURE:
<223> OTHER INFORMATION: Synthetic oligonucleotide

<400> SEQUENCE: 2
ctatctgtcg acgacttggt taccctggtt cgaagtgtgg ctcaagtagc ga        52

<210> SEQ ID NO 3
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 3
gatagatagt tgttgaatta atgggattaa gttttatatc gagtttatcg tt        52

<210> SEQ ID NO 4
<211> LENGTH: 52
<212> TYPE: DNA
<213> ORGANISM: Artificial Sequence
<220> FEATURE:
<223> OTHER INFORMATION: Synthetic oligonucleotde

<400> SEQUENCE: 4
ctatctatca acaacttaat taccctaatt caaaatatag ctcaaatagc aa        52

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
gatagatagt tgttgaatt                                             19

<210> SEQ ID NO 6
<211> LENGTH: 123
<212> TYPE: DNA
<213> ORGANISM: Artificial Sequence
<220> FEATURE:
<223> OTHER INFORMATION: Synthetic oligonucleotide

<400> SEQUENCE: 6
cagactgctg tgctagcaat cagcgggact ccgtgggcgt aggaccctcc gagccagcaa    60
gggaagcttt tggaagccac ccggtagagc tggaagagaa tttcgaaatc aattcgctca    120
acc                                                                 123
```

What is claimed is:

1. A method for genome-wide methylation-sensitive chromatin structure determination comprising:

providing eukaryotic cells with nuclei comprised of chromatin, wherein the chromatin is comprised of nucleosomes having DNA associated with histones;

extracting the nuclei of the cells;

methylating GpC sites of the chromatin by incubating a combination of the nuclei, sucrose and a GpC methylating reagent comprising an effective amount of a GPC methyltransferase and a methyl transfer agent, wherein the GpC methyltransferase is M. CviPI, wherein the concentration of M. CviPI is between about 50 and 500 U in a volume of about 0.5 mL, wherein the concentration of nuclei is about 250,000 nuclei in a volume of about 0.5 mL wherein the solution comprising M. CviPI and nuclei further comprises about 32 mM of the methyl transfer agent SAM, about 1M sucrose and CviPI buffer, wherein the solution is incubated at about 37° C. for about 15 minutes, and wherein the effective amount of the GpC methyltransferase and the methyl transfer agent is an amount effective to methylate GpC sites of chromatin not associated with nucleosomes without substantially methylating GpC sites of chromatin associated with nucleosomes;

purifying the DNA;

bisulfite converting the DNA;

sequencing the DNA; and determining the endogenous methylation state of the DNA and the GpC sites associated with the nucleosomes.

2. The method of claim 1, wherein the step of extracting the nuclei comprises a step of lysing the cells to lyse the cytoplasmic membrane of the cell.

3. The method of claim 1, wherein the effective amount of the GPC methyltransferase and the methyl transfer agent is an amount effective to methylate at least 90% of the GpC sites of the chromatin not associated with nucleosomes.

4. The method of claim 3, wherein the effective amount of the GPC methyltransferase and the methyl transfer agent is an amount effective to methylate at least 99% of the GpC sites of the chromatin not associated with nucleosomes.

5. The method of claim 3, wherein the effective amount of the GPC methyltransferase and the methyl transfer agent is an amount effective to methylate less than 10% of the GpC sites of the chromatin associated with nucleosomes.

6. The method of claim 1, wherein the amount of the GpC methyltransferase is about 100 U.

7. The method of claim 1, wherein the amount of the GpC methyltransferase is added in more than one aliquot.

8. The method of claim 7, wherein the more than one aliquot comprises a first aliquot of 200 U and a second aliquot of 100 U.

* * * * *